US012735420B2

(12) United States Patent
Laufer et al.

(10) Patent No.: US 12,735,420 B2
(45) Date of Patent: Sep. 15, 2026

(54) IMIDAZO[4,5-C]QUINOLINE COMPOUNDS AND THEIR USE AS ATM KINASE INHIBITORS

(71) Applicant: Universitatsklinikum Tubingen, Tubingen (DE)

(72) Inventors: Stefan Laufer, Heidelberg (DE); Michael Forster, Heidelberg (DE); Teodor Dimitrov, Heidelberg (DE); Lars Zender, Heidelberg (DE); Athina Moschopoulou, Heidelberg (DE)

(73) Assignee: Universitaetsklinikum Tuebingen, Tuebingen (DE)

( * ) Notice: Subject to any disclaimer, the term of this patent is extended or adjusted under 35 U.S.C. 154(b) by 443 days.

(21) Appl. No.: 18/141,656

(22) Filed: May 1, 2023

(65) Prior Publication Data

US 2023/0348462 A1 Nov. 2, 2023

Related U.S. Application Data

(63) Continuation of application No. PCT/EP2021/079965, filed on Oct. 28, 2021.

(30) Foreign Application Priority Data

Nov. 3, 2020 (EP) .................................... 20205316

(51) Int. Cl.

| | |
|---|---|
| ***C07D 471/04*** | (2006.01) |
| ***A61P 35/00*** | (2006.01) |
| ***C07D 519/00*** | (2006.01) |

(52) U.S. Cl.
CPC ............ *C07D 471/04* (2013.01); *A61P 35/00* (2018.01); *C07D 519/00* (2013.01)

(58) Field of Classification Search
CPC ...... C07D 471/04; C07D 519/00; A61P 35/00
See application file for complete search history.

(56) References Cited

FOREIGN PATENT DOCUMENTS

| | | | | |
|---|---|---|---|---|
| WO | 2013053273 | A1 | | 4/2013 |
| WO | 2017046216 | A1 | | 3/2017 |
| WO | WO2017076895 | A1 | * | 5/2017 |
| WO | 2017194632 | A1 | | 11/2017 |
| WO | 2018167203 | A1 | | 9/2018 |

OTHER PUBLICATIONS

Anderson et al. (Chem. Res. Toxicol. 2009; 22: 243-256) (Year: 2009).*
International Search Report for International Application No. PCT/EP2021/079965, mailed Jan. 26, 2022 (4 pages).
Written Opinion of the International Searching Authority for International Application No. PCT/EP2021/079965, mailed Jan. 26, 2022 (7 pages).
International Preliminary Report on Patentability for International Application No. PCT/EP2021/079965, issued May 8, 2023 (8 pages).

* cited by examiner

*Primary Examiner* — Brandon J Fetterolf

(57) ABSTRACT

The present invention relates to imidazo[4,5-c]quinoline compounds and to their use in the inhibition, regulation and/or modulation of signal transduction by ATM kinase and, in particular, for the treatment of ATM mediated diseases, especially cancer.

7 Claims, No Drawings

IMIDAZO[4,5-C]QUINOLINE COMPOUNDS AND THEIR USE AS ATM KINASE INHIBITORS

CROSS REFERENCES TO RELATED APPLICATIONS

The present application is a continuation of copending International Patent Application PCT/EP2021/079965 filed on 28 Oct. 2021 and designating the United States of America, which in turn claims priority of European patent application 20205316.1 filed on 3 Nov. 2020, which are both incorporated herein by reference in their entirety.

FIELD OF THE INVENTION

The present invention relates to imidazo[4,5-c]quinoline compounds and to their use in the inhibition, regulation and/or modulation of signal transduction by ATM kinase and, in particular, for the treatment of ATM mediated diseases, especially cancer.

BACKGROUND OF THE INVENTION

ATM kinase is a serine threonine kinase which was originally identified as the product of the gene mutated in ataxia telangiectasia. ATM kinase belongs to the PIKK family of kinases having domains with homology to phosphoinositide kinases. These kinases are involved in a plurality of key cellular functions, such as cell growth, cell proliferation, migration, differentiation, survival and cell adhesion. ATM kinase responds to direct double strand breaks caused by common anti-cancer treatments such as ionizing radiation and topoisomerase-II inhibitors but also to topoisomerase-I inhibitors. ATM kinase inhibitors can potentiate the activity of these agents and are therefore expected to be useful in the treatment of cancer.

Imidazo[4,5-c]quinolin-2-one compounds and their use as ATM kinase inhibitors in treating cancer is, for example, disclosed in WO 2015/073804 and WO 2015/170081. Compounds having the same basic skeleton are disclosed in WO 2017/046216, WO2017/076895, WO2017/076898, WO 2017/153578, WO 2017/174446, WO 2017/194632, WO2018/167203, WO 2016/155884, WO 2012/097039, WO 2006/122806, WO 2007/075468, WO 2012/007926, WO2016/141296, WO 2019/201283, CN102399218A, and CN 102372711A.

SUMMARY OF THE INVENTION

The problem underlying the invention is to provide compounds that are effective in inhibiting, regulating and/or modulating ATM kinase, in particular compounds that have an inhibitory effect against ATM. A further problem is to provide compounds that are effective in the treatment of cancer. A further problem is to provide compounds that are more effective in inhibiting, regulating and/or modulating ATM kinase, in particular compounds that have an increased inhibitory effect against ATM. A further problem is to provide compounds that are more effective in the treatment of cancer.

Surprisingly, the problem has been achieved by providing the compounds of formula (I) as shown below.

Thus, the invention relates to the following embodiments:

1. A compound having formula (I)

(I)

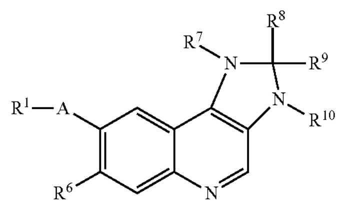

and the pharmaceutically acceptable salts, prodrugs, biologically active metabolites, solvates and stereoisomers thereof, wherein the variables in formula (I) have the meanings as follows:

A is a group of the formula

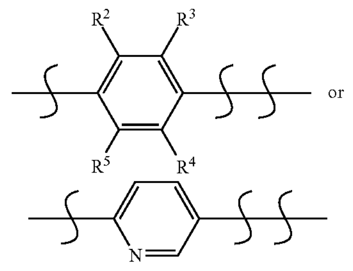

or wherein ∫ denotes the attachment to $R^1$ and ∫∫ denotes the attachment to the quinoline group;

$R^1$ is X—C(═O)—$NR^{11}$— or $R^{18}R^{19}$N-alkyl-O— or a group of the formula

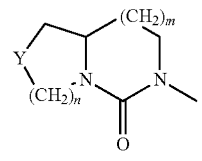

wherein m is 0 or 1;

n is 0, 1 or 2; and

Y is $CH_2$, $CHNR^{12}R^{13}$ or $NR^{11}$;

X is selected from

—$NR^{11}R^{16}$, wherein $R^{16}$ is a 4-, 5- or 6-membered heterocyclic ring which optionally comprises an additional nitrogen or oxygen heteroatom and is attached with a carbon atom to —$NR^{11}$ and which ring is optionally substituted with alkyl or —(O═C)$OR^{17}$;

—$NR^{11}$-alkyl, wherein the alkyl group is optionally substituted with —$NR^{18}R^{19}$; and —$NR^{14}R^{15}$, wherein $R^{14}$ and $R^{15}$ together with the nitrogen atom to which they are attached form a 4-, 5- or 6-membered monocyclic or 6-, 7- or 8-membered bicyclic heterocyclic ring which ring optionally contains a second nitrogen heteroatom and is optionally substituted with a substituent selected from alkyl, —$NR^{12}R^{13}$, and —$NR^{11}$(C═O)$OR^{10}$;

$R^2$, $R^3$, $R^4$ and $R^5$, which may be the same or different, are H, alkyl, alkoxy or halogen;

$R^6$ is H, alkyl or halogen;

$R^7$ is alkoxyalkyl, a 4-, 5-, 6-, or 7-membered heterocyclic group containing one or two oxygen atoms, alkyl, alkyl substituted with —$NR^{18}R^{19}$, alkyl(C═O)—, alkyl-$NR^{11}$(C═O)alkyl-, alkyl-(C═O)$NR^{11}$alkyl-, cycloalkyl; with the proviso that $R^7$ is alkoxyalkyl, alkyl substituted with —$NR^{18}R^{19}$, alkyl(C═O)—, alkyl-$NR^{11}$(C═O)alkyl-, or alkyl-(C═O)$NR^{11}$alkyl-, if $R^1$ is $R^{18}R^{19}$N-alkyl-O— and $R^8$ and $R^9$ together with the carbon atom to which they are attached form a carbonyl group;

$R^8$ and $R^9$ together with the carbon atom to which they are attached form a carbonyl group and $R^{10}$ is H or alkyl;

or $R^9$ and $R^{10}$ together form a bond such that there is a double bond between the carbon and nitrogen atom to which they are attached and $R^8$ is H, aryl, alkyl, or a 5- or 6-membered heteroaryl containing one or two heteroatoms independently selected from O and N;

$R^{11}$ is H or alkyl;

$R^{12}$ and $R^{13}$, which may be the same or different, are H or alkyl;

$R^{17}$ is H or alkyl;

$R^{18}$ and $R^{19}$, which may be the same or different, are H or alkyl or $R^{18}$ and $R^{19}$ together with the nitrogen atom to which they are attached form a 4-, 5- or 6-membered heterocyclic ring which is optionally substituted with one or two substituents which are independently selected from F or Cl.

2. A compound of embodiment 1, wherein $R^1$ is X—C(═O)—$NR^{11}$; and the pharmaceutically acceptable salts, prodrugs, biologically active metabolites, solvates and stereoisomers thereof.

3. A compound of embodiment 1 or 2, wherein $R^8$ and $R^9$ together with the carbon atom to which they are attached form a carbonyl group; and the pharmaceutically acceptable salts, prodrugs, biologically active metabolites, solvates and stereoisomers thereof.

4. A compound of any one of embodiments 1 to 3, wherein A is a group of the formula

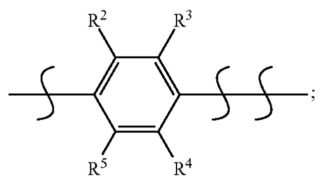

and the pharmaceutically acceptable salts, prodrugs, biologically active metabolites, solvates and stereoisomers thereof.

5. A compound of any one of embodiments 1 to 4, wherein $R^2$, $R^3$, $R^4$ and $R^5$, which may be the same or different, are H, alkyl, or halogen; and the pharmaceutically acceptable salts, prodrugs, biologically active metabolites, solvates and stereoisomers thereof.

6. A compound of any one of embodiments 1 to 5, wherein $R^2$, $R^3$, $R^4$ and $R^5$ are H; and the pharmaceutically acceptable salts, prodrugs, biologically active metabolites, solvates and stereoisomers thereof.

7. A compound of any one of embodiments 1 to 5, wherein $R^2$ is halogen, in particular fluoro or chloro, and $R^3$, $R^4$ and $R^5$ are H; and the pharmaceutically acceptable salts, prodrugs, biologically active metabolites, solvates and stereoisomers thereof.

8. A compound of any one of embodiments 1 to 5, wherein $R^4$ is halogen, in particular fluoro or chloro, or alkyl, in particular methyl, and $R^2$, $R^3$ and $R^5$ are H; and the pharmaceutically acceptable salts, prodrugs, biologically active metabolites, solvates and stereoisomers thereof.

9. A compound of any one of embodiments 1 to 5, wherein $R^3$ and $R^4$, which may be the same or different, are halogen, in particular fluoro or chloro, and $R^2$ and $R^5$ are H; and the pharmaceutically acceptable salts, prodrugs, biologically active metabolites, solvates and stereoisomers thereof.

10. A compound of any one of embodiments 1 to 5, wherein $R^4$ and $R^5$, which may be the same or different, are halogen, in particular fluoro or chloro, or alkyl, in particular methyl, and $R^2$ and $R^3$ are H; and the pharmaceutically acceptable salts, prodrugs, biologically active metabolites, solvates and stereoisomers thereof.

11. A compound of any one of embodiments 1 to 4, wherein $R^2$ and $R^4$, which may be the same or different, is halogen, in particular fluoro or chloro, or alkyl, in particular methyl, and $R^3$ and $R^5$ are H; and the pharmaceutically acceptable salts, prodrugs, biologically active metabolites, solvates and stereoisomers thereof.

12. A compound of any one of embodiments 1 to 5, wherein $R^2$ and $R^5$, which may be the same or different, are halogen, in particular fluoro or chloro, and $R^2$ and $R^5$ are H; and the pharmaceutically acceptable salts, prodrugs, biologically active metabolites, solvates and stereoisomers thereof.

13. A compound of any one of the preceding embodiments, wherein $R^6$ is H; and the pharmaceutically acceptable salts, prodrugs, biologically active metabolites, solvates and stereoisomers thereof.

14. A compound of any one of the preceding embodiments, wherein $R^7$ is alkoxyalkyl, a 4-, 5-, 6-, or 7-membered heterocyclic group containing one or two oxygen atoms, alkyl, alkyl substituted with —$NR^{18}R^{19}$, or cycloalkyl; and the pharmaceutically acceptable salts, prodrugs, biologically active metabolites, solvates and stereoisomers thereof.

15. A compound of embodiment 14, wherein $R^7$ is alkoxyalkyl or a 4-, 5-, or 6-membered heterocyclic group containing one oxygen atom; and the pharmaceutically acceptable salts, prodrugs, biologically active metabolites, solvates and stereoisomers thereof.

16. A compound of embodiment 15, wherein $R^7$ is alkoxyalkyl, tetrahydrofuranyl or oxanyl; and the pharmaceutically acceptable salts, prodrugs, biologically active metabolites, solvates and stereoisomers thereof.

17. A compound of embodiment 16, wherein $R^7$ is alkoxyalkyl; and the pharmaceutically acceptable salts, prodrugs, biologically active metabolites, solvates and stereoisomers thereof.

18. A compound of any one of the preceding embodiments, wherein $R^{10}$ is alkyl; and the pharmaceutically acceptable salts, prodrugs, biologically active metabolites, solvates and stereoisomers thereof.

19. A compound of any one of the preceding embodiments, wherein X is —$NR^{11}R^{16}$ and $R^{16}$ is a 4-, 5- or 6-membered heterocyclic ring selected from azetidinyl, pyrrolidinyl, piperidinyl, piperazinyl, and morpholinyl which ring is optionally substituted with alkyl or —(O═C)$OR^{17}$; and the pharmaceutically acceptable salts, prodrugs, biologically active metabolites, solvates and stereoisomers thereof.

20. A compound of embodiment 19, wherein the heterocyclic ring is selected from azetidinyl, pyrrolidinyl, piperidinyl, and piperazinyl, which ring is optionally substituted with alkyl or —(O═C)OR$^{17}$; and the pharmaceutically acceptable salts, prodrugs, biologically active metabolites, solvates and stereoisomers thereof.

21. A compound of embodiments 19 or 20, wherein the heterocyclic ring is unsubstituted or substituted at the N-heteroatom; and the pharmaceutically acceptable salts, prodrugs, biologically active metabolites, solvates and stereoisomers thereof.

22. A compound of any one of embodiments 1 to 18, wherein X is $C_2$-$C_3$-alkyl-NR$^{11}$—, wherein the alkyl group is optionally substituted with —NR$^{18}$R$^{19}$; and the pharmaceutically acceptable salts, prodrugs, biologically active metabolites, solvates and stereoisomers thereof.

23. A compound of embodiment 22, wherein the alkyl group is substituted with —NR$^{18}$R$^{19}$; and the pharmaceutically acceptable salts, prodrugs, biologically active metabolites, solvates and stereoisomers thereof.

24. A compound of embodiment 22 or 23, wherein R$^{18}$ and R$^{19}$ are independently $C_1$-$C_4$-alkyl; and the pharmaceutically acceptable salts, prodrugs, biologically active metabolites, solvates and stereoisomers thereof.

25. A compound of any one of embodiments 1 to 18, wherein X is —NR$^{14}$R$^{15}$, wherein R$^{14}$ and R$^{15}$ together with the nitrogen atom to which they are attached form a heterocyclic ring selected from azetidinyl, pyrrolidinyl, piperidinyl, piperazinyl, morpholinyl and 3,6-diazabicyclo[2.2.1] heptane, which ring is optionally substituted with a substituent selected from alkyl, —NR$^{12}$R$^{13}$, and —NR$^{11}$(C═O)OR$^{10}$; and the pharmaceutically acceptable salts, prodrugs, biologically active metabolites, solvates and stereoisomers thereof.

26. A compound of embodiment 25, wherein the heterocyclic ring is selected from azetidinyl, pyrrolidinyl, piperidinyl, piperazinyl, and 3,6-diazabicyclo[2.2.1]heptane, and is substituted with a substituent selected from alkyl, —NR$^{12}$R$^{13}$, and —NR$^{11}$(C═O)OR$^{10}$; and the pharmaceutically acceptable salts, prodrugs, biologically active metabolites, solvates and stereoisomers thereof.

27. A compound of embodiment 26, wherein the heterocyclic ring is N-alkyl-substituted piperazinyl; and the pharmaceutically acceptable salts, prodrugs, biologically active metabolites, solvates and stereoisomers thereof.

28. A compound of embodiment 1 or 2, wherein

A is a group of the formula

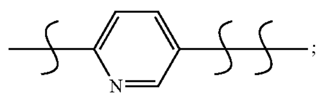

R$^1$ is X—C(═O)—NR$^{11}$;

R$^8$ and R$^9$ together with the carbon atom to which they are attached form a carbonyl group; and the pharmaceutically acceptable salts, prodrugs, biologically active metabolites, solvates and stereoisomers thereof.

29. A compound of embodiment 28, wherein X is —NR$^{11}$-alkyl, wherein the alkyl group is substituted with —NR$^{18}$R$^{19}$; R$^{18}$ and R$^{19}$ are H or alkyl; and the pharmaceutically acceptable salts, prodrugs, biologically active metabolites, solvates and stereoisomers thereof.

30. A compound of embodiment 28, wherein X is-NR$^{14}$R$^{15}$, wherein R$^{14}$ and R$^{15}$ together with the nitrogen atom to which they are attached form a 4-, 5- or 6-membered monocyclic heterocyclic ring which ring optionally contains a second nitrogen heteroatom and is optionally substituted with a substituent selected from alkyl, —NR$^{12}$R$^{13}$, and —NR$^{11}$(C═O)OR$^{10}$; and the pharmaceutically acceptable salts, prodrugs, biologically active metabolites, solvates and stereoisomers thereof.

31. A compound of embodiment 30, wherein X is-NR$^{14}$R$^{15}$, wherein R$^{14}$ and R$^{15}$ together with the nitrogen atom to which they are attached form a 4-, 5- or 6-membered monocyclic heterocyclic ring selected from pyrrolidinyl, piperidinyl, piperazinyl, wherein the piperazinyl is optionally substituted with alkyl or —NR$^{12}$R$^{13}$; and the pharmaceutically acceptable salts, prodrugs, biologically active metabolites, solvates and stereoisomers thereof.

32. A compound of any one of embodiments 28 to 31, wherein R$^7$ is alkoxyalkyl, a 4-, 5-, 6-, or 7-membered heterocyclic group containing one or two oxygen atoms, alkyl, alkyl substituted with —NR$^{18}$R$^{19}$, or cycloalkyl; and the pharmaceutically acceptable salts, prodrugs, biologically active metabolites, solvates and stereoisomers thereof.

33. A compound of embodiment 32, wherein R$^7$ is tetrahydrofuranyl or oxanyl; and the pharmaceutically acceptable salts, prodrugs, biologically active metabolites, solvates and stereoisomers thereof.

34. A compound of embodiment 3, wherein R$^1$ is R$^{18}$R$^{19}$N-alkyl-O—; R$^7$ is alkoxyalkyl; R$^{18}$ and R$^{19}$, which may be the same or different, are H or alkyl; and the pharmaceutically acceptable salts, prodrugs, biologically active metabolites, solvates and stereoisomers thereof.

35. A compound of any one of embodiments 28 to 34, wherein R$^6$ is H; and the pharmaceutically acceptable salts, prodrugs, biologically active metabolites, solvates and stereoisomers thereof.

36. A compound of any one of embodiments 28 to 35, wherein R$^{10}$ is alkyl; and the pharmaceutically acceptable salts, prodrugs, biologically active metabolites, solvates and stereoisomers thereof.

37. A compound of embodiment 1, wherein R$^9$ and R$^{10}$ together form a bond such that there is a double bond between the carbon and nitrogen atom to which they are attached and R$^8$ is H, aryl, alkyl, or a 5- or 6-membered heteroaryl containing one or two heteroatoms independently selected from O and N; and the pharmaceutically acceptable salts, prodrugs, biologically active metabolites, solvates and stereoisomers thereof.

38. A compound of embodiment 37, wherein A is

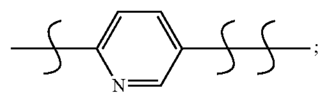

and the pharmaceutically acceptable salts, prodrugs, biologically active metabolites, solvates and stereoisomers thereof.

39. A compound of embodiment 37 or 38, wherein R$^1$ is and the pharmaceutically acceptable salts, prodrugs, biologically active metabolites, solvates and stereoisomers thereof.

40. A compound of embodiment 39, wherein R$^1$ is R$^{18}$R$^{19}$N—$C_2$-$C_4$-alkyl-O—; and the pharmaceutically acceptable salts, prodrugs, biologically active metabolites, solvates and stereoisomers thereof.

41. A compound of embodiment 39 or 40, wherein R$^{18}$ and R$^{19}$, which may be the same or different, are H or alkyl; and the pharmaceutically acceptable salts, prodrugs, biologically active metabolites, solvates and stereoisomers thereof.

42. A compound of any one of embodiments 36 to 41, wherein $R^6$ is H; and the pharmaceutically acceptable salts, prodrugs, biologically active metabolites, solvates and stereoisomers thereof.

43. A compound of any one of embodiments 37 to 42, wherein $R^7$ is alkoxyalkyl, a 4-, 5-, 6-, or 7-membered heterocyclic group containing one or two oxygen atoms, alkyl, alkyl substituted with —$NR^{18}R^{19}$, or cycloalkyl; and the pharmaceutically acceptable salts, prodrugs, biologically active metabolites, solvates and stereoisomers thereof.

44. A compound of embodiment 43, wherein $R^7$ is alkoxyalkyl or a 4-, 5-, or 6-membered heterocyclic group comprising one oxygen atom.

45. A compound of embodiment 43, wherein $R^7$ is tetrahydrofuranyl or oxanyl; and the pharmaceutically acceptable salts, prodrugs, biologically active metabolites, solvates and stereoisomers thereof.

46. A compound of any one of embodiments 37 to 45, wherein $R^8$ is H, aryl, alkyl, furyl, pyrrolyl or pyridinyl; and the pharmaceutically acceptable salts, prodrugs, biologically active metabolites, solvates and stereoisomers thereof.

47. A compound of any one of embodiments 37 to 45, wherein $R^8$ is H, phenyl, or furyl; and the pharmaceutically acceptable salts, prodrugs, biologically active metabolites, solvates and stereoisomers thereof.

48. A compound of any one of embodiments 1, 3 to 6 and 13 to 18, wherein $R^1$ is a group of the formula a) or b)

(a)

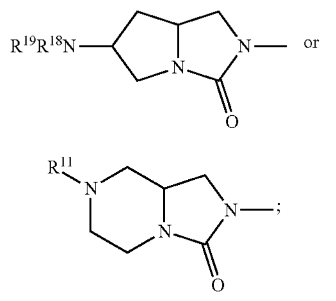

or (b)

and the pharmaceutically acceptable salts, prodrugs, biologically active metabolites, solvates and stereoisomers thereof.

49. A compound of embodiment 48, wherein $R^1$ is of formula (a), wherein $R^{18}$ and $R^{19}$ are independently H or alkyl; and the pharmaceutically acceptable salts, prodrugs, biologically active metabolites, solvates and stereoisomers thereof.

50. A compound of embodiment 48, wherein $R^1$ is of formula (b), wherein $R^{11}$ is alkyl; and the pharmaceutically acceptable salts, prodrugs, biologically active metabolites, solvates and stereoisomers thereof.

51. A compound of embodiment 23, wherein the alkyl group is substituted with —$NR^{18}R^{19}$ and $R^{18}$ and $R^{19}$ together with the nitrogen atom to which they are attached form an azetidinyl group which may be substituted with one or two substituents which are independently selected from F or Cl; and the pharmaceutically acceptable salts, prodrugs, biologically active metabolites, solvates and stereoisomers thereof.

52. A pharmaceutical composition comprising a compound of any one of embodiments 1 to 51 or a pharmaceutically acceptable salt, prodrug, biologically active metabolite, solvate or stereoisomer thereof, optionally together with an inert carrier.

53. A composition of embodiment 52, which additionally comprises one or more other therapeutic agents.

54. A compound of any one of embodiments 1 to 51 or a pharmaceutically acceptable salt, prodrug, biologically active metabolite, solvate or stereoisomer thereof or a composition of embodiment 52 or 53 for use in the treatment of a disease mediated by ATM kinase.

55. A compound of any one of embodiments 1 to 51 or a pharmaceutically acceptable alt, prodrug, biologically active metabolite, solvate or stereoisomer thereof or a composition of embodiment 52 or 53 for use in the treatment of cancer.

56. A compound of any one of embodiments 1 to 51 or a pharmaceutically acceptable salt, prodrug, biologically active metabolite, solvate or stereoisomer thereof or a composition of embodiment 52 or 53 for use in the treatment of colorectal cancer, glioblastoma, gastric cancer, ovarian cancer, diffuse large B-cell lymphoma, chronic lymphotic leukemia, acute myeloid leukemia, head and neck squamous cell carcinoma, breast cancer, hepatocellular carcinoma, small cell lung cancer, or non-small cell lung cancer.

57. A method for treating a disease in which mediation (inhibition, regulation and/or modulation) of ATM kinase is beneficial in a human or a warm-blooded animal in need of such treatment, which comprises administering to said human or warm-blooded animal a therapeutically effective amount of a compound of any one of embodiments 1 to 51 or a pharmaceutically acceptable salt, prodrug, biologically active metabolite, solvate or stereoisomer thereof or a composition of embodiment 52 or 53.

58. A method for treating cancer in a human or a warm-blooded animal in need of such treatment, which comprises administering to said human or warm-blooded animal a therapeutically effective amount of a compound of any one of embodiments 1 to 51 or a pharmaceutically acceptable salt, prodrug, biologically active metabolite, solvate or stereoisomer thereof or a composition of embodiment 52 or 53.

59. A method for treating a disease selected from colorectal cancer, glioblastoma, gastric cancer, ovarian cancer, diffuse large B-cell lymphoma, chronic lymphotic leukemia, acute myeloid leukemia, head and neck squamous cell carcinoma, breast cancer, hepatocellular carcinoma, small cell lung cancer, or non-small cell lung cancer in a human or a warm-blooded animal in need of such treatment, which comprises administering to said human or warm-blooded animal a therapeutically effective amount of a compound of any one of embodiments 1 to 51 or a pharmaceutically acceptable salt, prodrug, biologically active metabolite, solvate or stereoisomer thereof or a composition of embodiment 52 or 53.

60. A method for treating a disease as defined in any one of embodiments 57 to 59 which comprises administering said compound or a pharmaceutically acceptable salt, prodrug, biologically active metabolite, solvate or stereoisomer thereof or a composition of embodiment 51 or 52, in combination with radiotherapy.

61. A method of embodiment 60, wherein the radiotherapy is selected from external radiation therapy, intraoperative radiation therapy, internal radiation therapy, brachytherapy, or systemic therapy.

62. A method of embodiment 60 or 61, wherein said compound or a pharmaceutically acceptable salt, prodrug, biologically active metabolite, solvate or stereoisomer thereof or composition of embodiment 52, in combination with radiotherapy is administered simultaneously, separately or sequentially with radiotherapy.

DETAILED DESCRIPTION OF THE INVENTION

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluoro, chloro, bromo or iodo, in particular fluoro or chloro.

"Alkyl" is a straight-chain or branched alkyl group which is preferably a $C_1$-$C_6$-alkyl group, i.e. an alkyl group having from 1 to 6 carbon atoms, and more preferably a $C_1$-$C_4$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, n-hexyl, and the like.

The definition of alkyl is likewise applicable to any group which includes an alkyl group, such as alkoxy.

"Alkoxyalkyl" is an alkyl group as defined above substituted by an alkoxy group. This is analogously applicable to the meanings alkyl-$NR^{11}$(C=O)alkyl- or alkyl-(C=O)$NR^{11}$alkyl-.

"Cycloalkyl" is a cycloaliphatic radical which is preferably $C_3$-$C_8$-cycloalkyl, i.e. a cycloalkyl group having from 3 to 8 ring carbon atoms. In particular, 3 to 6 carbon atoms form the cyclic structure, such as cyclopropyl, cyclobutyl, cyclopentyl and cyclohexyl.

"Aryl" is preferably phenyl or naphthyl.

"Heteroaryl containing one or two heteroatoms independently selected from O and N" means a 5- or 6-membered monocyclic aromatic group having 1 or 2 O- and/or N-heteroatoms. The heteroaryl group may be bound to the neighboring group via a carbon atom (C-bound) or via a nitrogen heteroatom (N-bound). Heteroaryl groups are for example: furyl, pyrrolyl, pyrazolyl, oxazolyl, isoxazolyl, imidazolyl, pyridinyl or pyrimidinyl. A preferred heteroaryl group is furyl, in particular 2-furyl.

The term "heterocyclic ring" refers to a 4-, 5-, 6- or 7-membered monocyclic ring which is saturated and comprises a N- or O-heteroatom and optionally a further heteroatom selected from N and O. In one instance the heterocyclic ring also means a 6-, 7- or 8-membered saturated bicyclic bridged heterocyclic ring. The heterocyclic ring may be N-bound or C-bound and optionally substituted with alkyl or —(O=C)Oalkyl. Examples for heterocyclic rings are azetidinyl, pyrrolidinyl, piperidinyl, piperazinyl, morpholinyl, oxetanyl, tetrahydrofuryl, oxanyl, hexahydrooxepinyl, diazabicyclo[2.2.1]heptan-yl, diazabicyclo[3.1.1]heptan-yl, azabicyclo[2.2.1]heptan-yl, azabicyclo[3.1.1]heptan-yl, diazabicyclo[2.2.2]octan-yl, and the like.

The term "the compounds of the invention" or "the compounds of formula (I)" includes the pharmaceutically acceptable salts, prodrugs, biologically active metabolites, solvates and stereoisomers thereof.

The pharmaceutically acceptable salts are especially acid addition salts with pharmaceutically acceptable acids. Examples of suitable pharmaceutically acceptable organic and inorganic acids are hydrochloric acid, hydrobromic acid, phosphoric acid, sulfuric acid, sulfamic acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäauser Verlag, Basel and Stuttgart, 1966.

The invention also includes any tautomeric, crystal and polymorphic forms of the compounds and salts and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by ($C_1$-$C_4$)alkyl, ($C_1$-$C_{12}$)alkanoyloxy-methyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, and the like.

The compounds of the invention inhibit, regulate and/or modulate ATM kinase and are therefore useful in therapy, in particular in the treatment of diseases or conditions mediated at least in part by ATM kinase. They are particularly useful in treating cancer including non-metastatic metastatic cancer and including treatment of primary tumors and tumor metastases.

In an embodiment, a compound of the invention is provided for use in therapy.

In another embodiment, a compound of the invention is provided for use in the treatment of a disease mediated by ATM kinase.

In another embodiment, a compound of the invention is provided for use in the treatment of a disease mediated by ATM kinase, where the disease is cancer, in particular colorectal cancer, glioblastoma, gastric cancer, ovarian cancer, diffuse large B-cell lymphoma, chronic lymphotic leukemia, acute myeloid leukemia, head and neck squamous cell carcinoma, breast cancer, hepatocellular carcinoma, small cell lung cancer, or non-small cell lung cancer. The compounds of the invention are also suitable for use in the treatment of Huntington's disease and as neuroprotective agent.

In another embodiment, the invention provides a method for treating a disease in which mediation (inhibition, regulation and/or modulation) of ATM kinase is beneficial in a human or a warm-blooded animal in need of such treatment, which comprises administering to said human or warm-blooded animal a therapeutically effective amount of a compound of the invention. A therapeutically effective amount can reduce the number of cancer or tumor cells, reduce the overall tumor size, inhibit or stop tumor cell infiltration into peripheral organs, inhibit or stop tumor metastasis, inhibit or stop tumor growth, relieve one or more of the symptoms associated with the cancer, reduce morbidity or mortality, improve quality of life, or a combination of such effects.

In another embodiment, the invention provides a method for treating a disease in which mediation (inhibition, regulation and/or modulation) of ATM kinase is beneficial in a human or a warm-blooded animal in need of such treatment, where the disease is cancer, in particular colorectal cancer, glioblastoma, gastric cancer, ovarian cancer, diffuse large B-cell lymphoma, chronic lymphotic leukemia, acute myeloid leukemia, head and neck squamous cell carcinoma, breast cancer, hepatocellular carcinoma, small cell lung cancer, or non-small cell lung cancer which comprises administering to said human or warm-blooded animal a therapeutically effective amount of a compound of the invention.

In another embodiment, any method of treatment of the invention is combined with radiotherapy which is preferably selected from external radiation therapy, intraoperative radiation therapy, internal radiation therapy, brachytherapy, or systemic therapy.

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention will normally be administered at a unit dose within the range of 2.5 to 5000 mg/m2 body area or 0.05 to 100 mg/kg of the human or animal. A unit dose form will usually contain 0.1 to 250 mg of compound of the invention. The daily dose will be necessarily varied depending upon the host treated, the route of administration, any co-therapies and the severity of the illness.

The compounds of the invention may also be suitable for combination with other therapeutic agents. The invention therefore further relates to a combination comprising a compound of the invention with one or more further therapeutic agents, in particular for use in treating cancer or associated diseases. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously or sequentially. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:

a) Antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEEI kinase;

b) antiangiogenic agents, such as those that inhibit the effects of vascular endothelial growth factor, for example the anti-vascular endothelial cell growth factor antibody bevacizumab and for example, a VEGF receptor tyrosine kinase inhibitor such as vandetanib (ZD6474), sorafenib, vatalanib (PTK787), sunitinib (*SUI* 1248), axitinib (AG-013736), pazopanib (GW 786034) and cediranib (AZD2171); compounds such as those disclosed in WO97/22596, WO 97/30035, WO 97/32856 and WO 98/13354; and compounds that work by other mechanisms (for example linomide, inhibitors of integrin czvß3 function and angiostatin), or inhibitors of angiopoietins and their receptors (Tie-I and Tie-2), inhibitors of PLGF, inhibitors of delta-like ligand (DLL-4);

c) other small molecule agents like inhibitors of protein phosphorylation (for example abemaciclib, acalabrutinib, afatinib, alectinib, avapritinib, axitinib, binimetinib, bosutinib, brigatinib, cabozantinib, capmatinib, ceritinib, cobimetinib, crizotinib, dabrafenib, dacomitinib, dasatinib, encorafenib, entrectinib, erdafitinib, erlotinib, everolimus, fedratinib, fostamatinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pemigatinib, pexidartinib, ponatinib, pralsetinib, regorafenib, ribociclib, ripretinib, ruxolitinib, selpercatinib, selumetinib, sirolimus, sorafenib, sunitinib, temsirolimus, trametinib, tucatinib, upadacitinib, vandetanib, vemurafenib, zanubrutinib) or inhibitors of protein-protein interactions (for example venetoclax, navitoclax) or proteasome inhibitors (for example bortezomib, carfilzomib, ixazomib, marizomib, delanzomib, oprozomib)

d) Immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-I (for example BMS-936558 or AMP-514), PD-LI (for example MED14736) and agonist antibodies to CD137 and other immune checkpoint inhibitors; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. antiCD33 antibody Mylotarg); immunotoxins such as moxetumumab pasudotox; agonists of toll-like receptor 7 or toll-like receptor 9; cellular immunotherapies for example CAR-T cell therapy; NK cell therapy, CAR-NK cell therapy, Tumor-inflitrating lymphocytes, recombinant T cells; vaccinations for example anti-tumor peptidvaccines, mRNA vaccines, dendritic cell vaccines.

e) Efficacy enhancers, such as leucovorin.

The compounds of the invention can be prepared by methods analogous to those used in the examples and by methods disclosed, for example, in WO 2009/155527, WO 2007/075468, WO 2015/073804, WO 2015/17008, WO 2017/046216, WO2017/076895, WO 2017/153578, WO 2018/167203, WO 2016/155884, WO 2012/097039, WO 2006/122806, WO 2007/075468, WO 2012/007926, WO2016/141296, WO 2019/201283.

EXAMPLES

The examples illustrate the invention without limiting it.

Abbreviations

AcOH acetic acid
$Ac_2O$ acetic anhydride
DMF dimethylformamide
DCM dichloromethane
THF tetrahydrofurane
EtOAc, EA ethylacetate
BuLi butyl lithium
TLC thin layer chromatography
MeOH methanol
PTsOH toluene sulfonic acid
$tBu_3P$ Pf G3 Mesyl[(tri-t-butylphosphine)-2-(2-aminobiphenyl)]palladium(II)
EtOH ethanol
$Et_2O$ diethylether
KOAc potassium acetate
$Pd(dppf)Cl_2$ 1,1'-bis(diphenylphosphino)ferrocene]dichloropalladium(II) (also as complex with DCM)
$Et_3N$ triethylamine

General

Chemical synthesis was carried out using commonly applied techniques and general procedures. All starting materials and reagents were of commercial quality and were used without further purification unless otherwise stated. Microwave-assisted reactions were performed in a CEM Discover 908005 System in pressure-sealed glass tubes. Thin layer chromatography (TLC) was carried out on Merck 60 F254 and Macherey Nagel ALUGRAM® Xtra SIL G/UV254 silica plates and were visualized under UV light (254 nm and 366 nm) or developed with an appropriate staining reagent. Preparative column chromatography was carried out with an Interchim PuriFlash 430 or PuriFlash XS420 automated flash chromatography system and were unless otherwise stated performed on normal phase silica gel (Grace Davison Davisil LC60A 20-45 micron or Merck Geduran Si60 63-200 micron).

Analytical Methods and Instrumentation:

NMR: $^1H$ and $^{13}C$ spectra were recorded on Bruker Avance 200, Bruker Avance 400 or Bruker Avance III HD instruments. The samples were dissolved in deuterated solvents and chemical shifts are given in relation to tetramethylsilane (TMS). Spectra were calibrated using the residual peaks of the used solvent.

MS: Mass spectra were obtained using a Advion TLC-MS interface with electron spray ionization (ESI) in positive and/or negative mode. Instrument settings as follows: ESI voltage 3.50 kV, capillary voltage 187 V, source voltage 44 V, capillary temperature 250° C., desolvation gas temperature 250° C., gas flow 5 l/min nitrogen.

HPLC: Purity of final compounds was determined using an Agilent 1100 Series LC with Phenomenex Luna C8 columns (150×4.6 mm, 5 μm) and detection was performed with a UV DAD at 254 nm and 230 nm wavelength. Elution was carried out with the following gradient: 0.01 M $KH_2PO_4$, pH 2.30 (solvent A), MeOH (solvent B), 40% B to 85% B in 8 min, 85% B for 5 min, 85% to 40% B in 1 min, 40% B for 2 min, stop time 16 min, flow 1.5 ml/min. All final compounds showed a purity above 95% in the means of area percent at the two different wavelengths.

Experimental Procedures

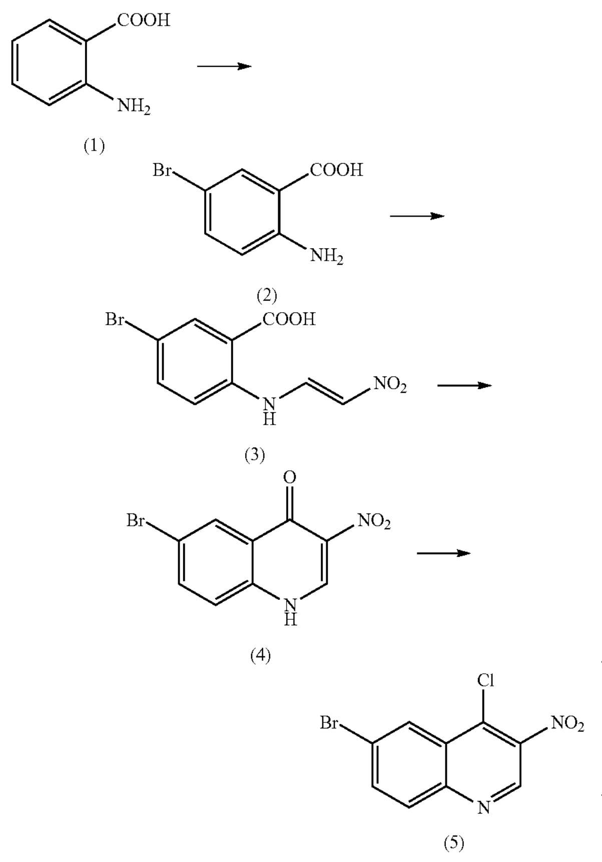

Common intermediate 6-bromo-4-chloro-3-nitroquinoline (2) was synthesized starting from anthranilic acid (1):

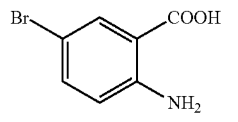

To a suspension of 10.29 g anthranilic acid (75 mmol) and 8.08 g $NH_4Br$ (83 mmol) in 75 ml AcOH were added 9.36 g $H_2O_2$ (83 mmol, 30% wt in $H_2O$) at about 10° C. internal temperature. The cooling bath was removed after complete addition and the reaction was allowed to reach ambient temperature. Upon warming a mild exothermic reaction was observed and most of the solids were dissolved. Later the product precipitated from the reaction mixture and stirring was continued until no formation of heat was observed. At this point HPLC indicated about 95% conversion and formation of smaller amounts of a byproduct (most probably dihalogenated product). The mixture was poured on 400 ml ice water with 4 g $Na_2SO_3$. The precipitate was collected by filtration and the crude product recrystallized from $H_2O$/EtOH to obtain 13.30 g (83%) of the title compound as beige crystalline solid. $^1H$ NMR (200 MHz, DMSO) δ 8.82 (br s, 3H), 7.76 (d, J=2.5 Hz, 1H), 7.33 (dd, J=8.9, 2.5 Hz, 1H), 6.73 (d, J=8.9 Hz, 1H). $^{13}C$ NMR (50 MHz, DMSO) δ 168.4, 150.6, 136.1, 132.9, 118.7, 111.2, 104.6. ESI-MS m/z: 214.8 $[M+H]^+$ HPLC $t_{ret}$=5.87 min.

(E)-5-Bromo-2-((2-nitrovinyl)amino)benzoic acid (3)

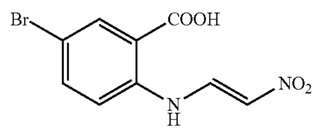 [SMILES: O=C(O)c1cc(Br)ccc1N/C=C/[N+](=O)[O-]]

Nitromethane (60 ml) was added in small portions to stirred aqueous NaOH in a rate that the internal temperature was held between 40-50° C. After complete addition, the mixture was stirred at 45° C. for 15 min until an amber solution was formed. This was added to a mixture of 300 g ice and 300 ml conc. HCl with external cooling in a rate that the temperature did not rise above 10° C. The resulting yellowish suspension of methazonic acid was immediately added to a pre-cooled suspension of 13.30 g (2)(62 mmol) in 500 ml water and 250 ml conc. HCl. The cooling bath was removed and the mixture was allowed to reach ambient temperature. Stirring was continued overnight and the resulting yellow suspension was filtered via a buchner funnel. The wet filter cake was resuspended in 1000 ml $H_2O$ stirred for an hour and filtered again. The solids were again resuspended in water and after 30 min of stirring filtered off and sucked as dry as possible. The filter cake was pre-dried in a convection oven at 45° C. and finally dried over $P_2O_5$ in vacuo. The title compound was obtained as yellow solid (15.90 g, 90%). $^1H$ NMR (200 MHz, DMSO) δ 12.92 (d, J=13.8 Hz, 1H), 8.09-7.91 (m, 2H), 7.80 (dd, J=9.0, 2.2 Hz, 1H), 7.68 (d, J=9.0 Hz, 1H), 6.75 (d, J=6.3 Hz, 1H) (COOH not detected or very broad)$^{13}C$ NMR (50 MHz, DMSO) δ 167.2, 140.3, 137.3, 136.9, 133.7, 118.3, 117.7, 115.0, 114.1. ESI-MS m/z: 241 $[M-CO_2-H]^-$ HPLC $t_{ret}$=5.91 min.

6-Bromo-3-nitroquinolin-4(1H)-one (4)

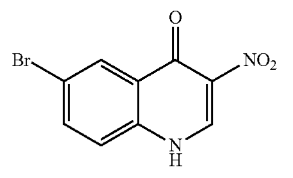 [SMILES: O=c1c([N+](=O)[O-])c[nH]c2ccc(Br)cc12]

A suspension of 15.09 g (3) (53 mmol) in 100 ml $Ac_2O$ was stirred at ambient temperature until a fine, easily stirrable suspension was formed. To this was added 6.19 g KOAc (63 mmol) and the reaction mixture was gradually heated up to 80° C. oil bath temperature. The suspension darkened and after partial dissolution of starting material, precipitation of solids was observed. Stirring was maintained at 80° C. until TLC indicated full consumption of starting material. Then the mixture was first allowed to cool to ambient temperature and was then further cooled with an ice bath. The solids were filtered off, washed sparingly with AcOH and then with water until the filtrate appeared almost colorless. The filter cake was pre-dried in a convection oven at 50° C. and finally dried over $P_2O_5$ in vacuo overnight. The title compound was obtained in sufficient purity as 9.41 g (67%) off-white to beige solid. $^1H$ NMR (200 MHz, DMSO) δ 13.09 (br s, 1H), 9.19 (s, 1H), 8.26 (d, J=2.3 Hz, 1H), 7.90 (dd, J=8.8, 2.3 Hz, 1H), 7.64 (d, J=8.8 Hz, 1H). $^{13}C$ NMR (50 MHz, $CDCl_3$) δ 166.4, 142.7, 137.3, 135.9, 131.1, 129.6, 128.0, 121.9, 118.7. ESI-MS m/z: 267.1 $[M-H]^-$ HPLC $t_{ret}$=4.37 min.

6-Bromo-4-chloro-3-nitroquinoline (5)

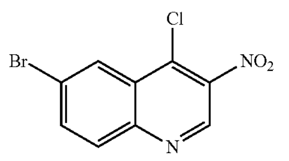 [SMILES: O=[N+]([O-])c1cnc2ccc(Br)cc2c1Cl]

To a suspension of 9.23 g (4) (34 mmol) in 80 ml DMF and was added 7.36 g $POCl_3$ (48 mmol) in small portions at ambient temperature. A mild exotherm was observed and stirring was continued at ambient temperature for about 2 hours. A dark solution formed and TLC indicated complete conversion. The reaction mixture was slowly poured on 500 ml ice water and stirring was continued with external cooling for 15 min. The precipitate was filtered off, washed with water and pre-dried in a convection oven at 50° C. Final drying over $P_2O_5$ in vacuo yielded the title compound as beige solid (9.70 g, 98%). Further purification can be achieved by re-dissolving the crude product in DCM and filtration over celite. Evaporation of the filtrate yields the title compound as beige crystalline solid. $^1H$ NMR (200 MHz, $CDCl_3$) δ 9.23 (s, 1H), 8.55 (d, J=1.9 Hz, 1H), 8.11-7.92 (m, 2H). $^{13}C$ NMR (50 MHz, $CDCl_3$) δ 147.9, 144.8, 141.7, 136.8, 135.4, 131.9, 128.2, 126.8, 124.6.

N,N-Dimethyl-3-((5-(4,4,5,5-tetramethyl-1,3,2-dioxaborolan-2-yl)pyridin-2-yl)oxy)propan-1-amine (7) was synthesized as described in WO2017/046216:

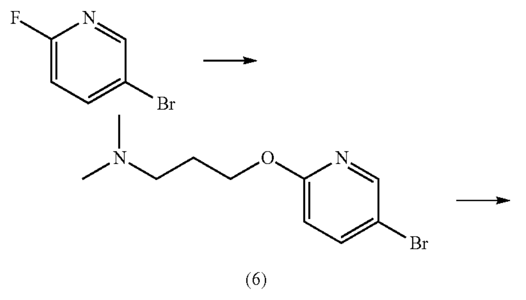

(6)

-continued

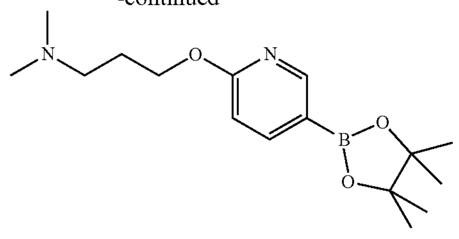

(7)

3-((5-Bromopyridin-2-yl)oxy)-N,N-dimethylpropan-1-amine (6)

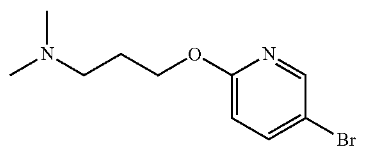

Sodium hydride (2.10 g, 53 mmol) was added in portions to an ice-cooled solution of 4.33 g 3-(dimethylamino)prop-1-ol (42 mmol) in 75 ml dry THF. After complete addition the cooling bath was removed and stirring was continued for 30 min at ambient temperature. Subsequently, 6.16 g 2-fluoro-5-bromopyridine (35 mmol) were added to the mixture and the temperature was increased to 50° C. for two hours. The reaction was cooled to ambient temperature and quenched by dropwise addition of 70 ml water. The mixture was diluted with EtOAc, transferred to a separatory funnel and the organic phase was washed twice with brine. After drying with $Na_2SO_4$, the organic phase was evaporated under reduced pressure to yield 9.18 g (quant.) of the title compound as yellow oil in sufficient purity. $^1H$ NMR (200 MHz, $CDCl_3$) δ 8.15 (dd, J=2.6, 0.6 Hz, 1H), 7.60 (dd, J=8.8, 2.6 Hz, 1H), 6.62 (dd, J=8.8, 0.6 Hz, 1H), 4.28 (t, J=6.6 Hz, 2H), 2.49-2.35 (m, 2H), 2.24 (s, 6H), 2.02-1.81 (m, 2H). $^{13}C$ NMR (50 MHz, $CDCl_3$) δ 162.8, 147.6, 141.1, 112.8, 111.6, 64.8, 56.5, 45.6, 27.3. HPLC $t_{ret}$=2.34 min.

N,N-Dimethyl-3-((5-(4,4,5,5-tetramethyl-1,3,2-dioxaborolan-2-yl)pyridin-2-yl)oxy)propan-1-amine (7)

(7)

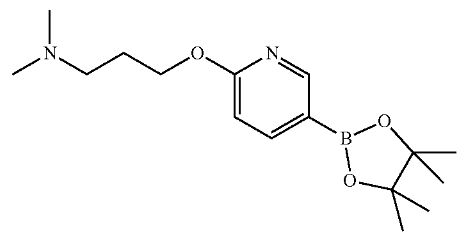

A solution of 1037 mg (6)(4 mmol) and 781 mg 2-isopropoxy-4,4,5,5-tetramethyl-1,3,2-dioxaborolane (4.2 mmol) in 16 ml anhydrous THF was cooled to −78° C. and 1.68 ml BuLi (4.2 mmol, 2.5 M in hexane) were added dropwise to the stirred solution. After stirring for 30 min at low temperature, TLC indicated full consumption of starting material and the reaction was quenched by addition of 0.5 ml half saturated $NH_4Cl$. The mixture was allowed to warm up to ambient temperature and diluted with EtOAc. The organic phase was washed twice with brine, dried over $Na_2SO_4$ and concentrated under reduced pressure. The title compound was obtained as yellow oil (1231 mg, quant. yield). $^1H$ NMR (200 MHz, $CDCl_3$) δ 8.48 (dd, J=2.0, 0.6 Hz, 1H), 7.87 (dd, J=8.3, 2.0 Hz, 1H), 6.65 (dd, J=8.3, 0.6 Hz, 1H), 4.32 (t, J=6.5 Hz, 2H), 2.46-2.35 (m, 2H), 2.21 (s, 6H), 1.99-1.83 (m, 2H), 1.29 (s, 12H). $^{13}C$ NMR (50 MHz, $CDCl_3$) δ 166.0, 154.3, 144.6, 110.3, 83.9, 82.9, 64.4, 56.6, 45.6, 27.4, 24.9. ESI-MS m/z: 329.4 $[M+Na]^+$.

Examples 1 to 6 were prepared via a four step synthetic route including $S_NAr$, $NO_2$ reduction, cyclization and Suzuki coupling starting from (5):

6-Bromo-3-nitro-N-(tetrahydro-2H-pyran-4-yl)quinolin-4-amine (8)

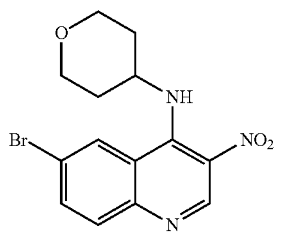

575 mg (5) (2 mmol) were dissolved in 8 ml dry DMF at ambient temperature and a solution of 305 mg $Et_3N$ (3 mmol) and 223 mg 4-aminotetrahydropyrane (2.2 mmol) in 1 ml dry DMF were added dropwise. The mixture was stirred for 30 min until TLC indicated complete conversion. The reaction was quenched by dropwise addition of half saturated $NH_4Cl$ solution until precipitation of a yellow solid. After dilution with additional $NH_4Cl$ solution, stirring was continued under ice-cooling for 20 min. The precipitate was filtered off, washed with water and the filter cake was dried to yield 670 mg (95%) of the title compound as yellow fluffy solid. $^1H$ NMR (200 MHz, DMSO) δ 8.97 (s, 1H), 8.69 (d, J=1.7 Hz, 1H), 8.23 (d, J=8.5 Hz, 1H), 7.94 (dd, J=8.9, 1.7 Hz, 1H), 7.80 (d, J=8.9 Hz, 1H), 3.95-3.80 (m, 2H), 3.79-3.59 (m, 1H), 3.45-3.21 (m, 2H), 2.01-1.58 (m, 4H). $^{13}C$ NMR (50 MHz, DMSO) δ 147.4, 147.2, 145.3, 135.0, 131.5, 127.5, 126.8, 121.5, 119.3, 65.7, 53.6, 32.8. ESI-MS m/z: 350.2 $[M-]^-$ HPLC $t_{ret}$=6.77 min.

6-Bromo-$N^4$-(tetrahydro-2H-pyran-4-yl)quinoline-3,4-diamine (9)

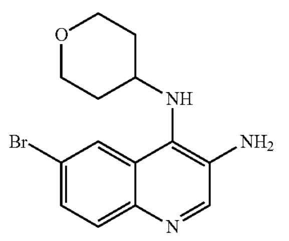 [SMILES: O=[N+]([O-])c1cnc2ccc(Br)cc2c1NC1CCOCC1]

A suspension of 633 mg (9) (1.8 mmol) and 1.62 g $SnCl_2$ dihydrate (7.2 mmol) in 30 ml EtOH was heated to reflux to form a clear solution. The mixture was stirred until TLC indicated complete conversion (about 2 hours). Then, 3.2 g solid $NaHCO_3$ was added and the reaction mixture was concentrated under reduced pressure. EtOAc (100 ml) was added and the mixture was sonicated to break down the agglomerated solids. The suspension was filtered over a bed of celite and the filter cake was washed with additional EtOAc. The filtrate was concentrated under reduced pressure and the residue was co-evaporated with DCM several times to yield the title compound as a slightly yellowish foamy solid (544 mg, 94%). $^1H$ NMR (200 MHz, $CDCl_3$) δ 8.47 (s, 1H), 7.90 (d, J=1.9 Hz, 1H), 7.80 (d, J=9.0 Hz, 1H), 7.48 (dd, J=9.0, 1.9 Hz, 1H), 4.16-3.57 (m, 4H), 3.56-3.26 (m, 4H), 1.94-1.76 (m, 2H), 1.72-1.46 (m, 2H). $^{13}C$ NMR (50 MHz, $CDCl_3$) δ 143.5, 142.4, 133.3, 132.2, 131.6, 129.1, 126.4, 122.6, 120.6, 67.1, 52.0, 35.1. ESI-MS m/z: 322.3 $[M+H]^+$ HPLC $t_{ret}$=2.68 min.

8-Bromo-1-(tetrahydro-2H-pyran-4-yl)-1H-imidazo[4,5-c]quinolone (10)

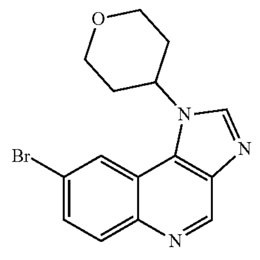 [SMILES: Brc1ccc2ncc3ncn(C4CCOCC4)c3c2c1]

To a solution of 97 mg (9) (0.3 mmol) in 3 ml toluene was added 133 mg triethyl orthoformate (0.9 mmol) and a catalytic amount pTsOH. The reaction vial was sealed and the mixture was heated up to 80° C. oil bath temperature until TLC indicated complete conversion. The formed suspension was diluted with 6 mL hexane and cooled with ice/water, prior to filtration. The isolated solid was washed with cold hexane and dried in vacuo to yield the title compound as brown solid. According to NMR, the crude product contained bigger amounts of TsOH. Flash purification (DCM/MeOH 2-8%) yielded the pure title compound as brownish solid. Yield: 72 mg (72%). $^1H$ NMR (200 MHz, $CDCl_3$) δ 9.27 (s, 1H), 8.22-8.00 (m, 3H), 7.69 (dd, J=8.9, 1.6 Hz, 1H), 5.04-4.77 (m, 1H), 4.30-4.13 (m, 2H), 3.82-3.62 (m, 2H), 2.42-2.02 (m, 4H). $^{13}C$ NMR (50 MHz, $CDCl_3$) δ 146.2, 143.3, 140.2, 138.3, 132.8, 131.2, 130.5, 122.6, 120.7, 119.1, 66.9, 55.0, 33.7. ESI-MS m/z: 332.3 $[M+H]^+$ HPLC $t_{ret}$=4.48 min.

8-Bromo-2-methyl-1-(tetrahydro-2H-pyran-4-yl)-1H-imidazo[4,5-c]quinolone (11)

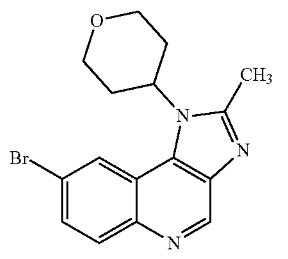 [SMILES: Cc1nc2cnc3ccc(Br)cc3c2n1C1CCOCC1]

To a solution of 97 mg (9) (0.3 mmol) in 3 ml toluene was added 146 mg triethyl orthoacetate (0.9 mmol) and a catalytic amount pTsOH. The reaction vial was sealed and the mixture was heated up to 80° C. oil bath temperature until TLC indicated complete conversion. The reaction mixture was concentrated under reduced pressure and the residue was triturated with hexane until precipitation of the product. The formed suspension was cooled with ice/water, prior to filtration. The isolated solid was washed with cold hexane and dried in vacuo to yield 80 mg (77%) of the title compound as off-white solid. $^{1}$H NMR (200 MHz, $CDCl_3$) δ 9.22 (s, 1H), 8.74-8.27 (m, 1H), 8.15 (d, J=9.0 Hz, 1H), 7.82-7.58 (m, 1H), 5.24-4.85 (m, 1H), 4.31 (dd, J=11.7, 4.1 Hz, 2H), 3.69 (t, J=11.7 Hz, 2H), 2.82 (s, 3H), 2.79-2.47 (m, 2H), 2.21-1.85 (m, 2H). $^{13}$C NMR (50 MHz, $CDCl_3$) δ 152.3, 145.1, 143.3, 137.1, 133.1, 132.8, 130.2, 123.5, 120.6, 118.9, 67.7, 55.2, 31.4, 17.6. ESI-MS m/z: 346.4 $[M+H]^+$ HPLC $t_{ret}$=4.50 min.

8-Bromo-2-(furan-2-yl)-1-(tetrahydro-2H-pyran-4-yl)-1H-imidazo[4,5-c]quinolone (12)

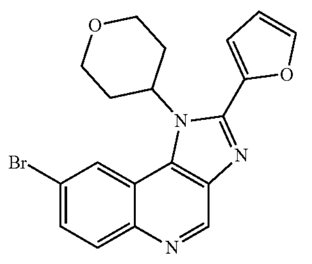 [SMILES: Brc1ccc2ncc3nc(-c4ccco4)n(C4CCOCC4)c3c2c1]

To an solution of 97 mg (9) (0.3 mmol) in 3 ml DMF was added 35 mg furfural (0.36 mmol) at ambient temperature. After 15 min of stirring, 36 μl water and 129 mg oxone (0.21 mmol) were added and stirring was continued at ambient temperature. TLC/MS indicated formation of the condensation intermediate and low conversion to the desired product. The mixture was heated up to 80° C. oil bath temperature and stirring was continued overnight. At this point TLC indicated sufficient conversion and the reaction was quenched by addition to aqueous $K_2CO_3$ solution. The aqueous phase was extracted with EtOAc (4×20 ml) and the combined extracts were washed once with brine. After drying and evaporation, the residue was purified via flash chromatography (DCM/MeOH 2-8%) to yield 36 mg (30%) of the title compound as reddish solid. $^{1}$H NMR (200 MHz, $CDCl_3$/MeOD) δ 9.35-9.15 (m, 1H), 8.48 (s, 1H), 8.20-8.04 (m, 1H), 7.82-7.64 (m, 2H), 7.12 (d, J=3.0 Hz, 1H), 6.72-6.55 (m, 1H), 5.27-5.06 (m, 1H), 4.33-4.09 (m, 2H), 3.69-3.48 (m, 2H), 2.73-2.41 (m, 2H), 2.08-1.89 (m, 2H). $^{13}$C NMR (50 MHz, $CDCl_3$/MeOD) δ 145.7, 145.5, 144.7, 144.2, 143.5, 137.3, 133.6, 132.5, 130.7, 124.4, 121.0, 119.0, 114.6, 112.5, 67.6, 56.1, 31.1. ESI-MS m/z: 398.1 $[M+H]^+$ HPLC $t_{ret}$=7.50 min.

8-Bromo-2-phenyl-1-(tetrahydro-2H-pyran-4-yl)-1H-imidazo[4,5-c]quinolone (13)

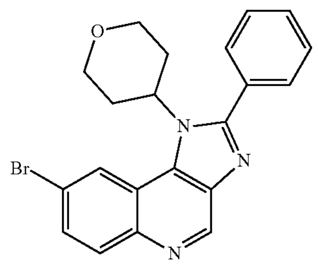 [SMILES: Brc1ccc2ncc3nc(-c4ccccc4)n(C4CCOCC4)c3c2c1]

To an solution of 97 mg (9) (0.3 mmol) in 3 ml DMF was added 38 mg benzaldehyde (0.36 mmol) at ambient temperature. After 15 min of stirring, 36 μl water and 129 mg oxone (0.21 mmol) were added and stirring was continued at ambient temperature. TLC/MS indicated formation of the condensation intermediate and low conversion to the desired product. The mixture was heated up to 80° C. oil bath temperature and stirring was continued overnight. At this point TLC indicated sufficient conversion and the reaction was quenched by addition to aqueous $K_2CO_3$ solution. The precipitate was collected by filtration and dried in vacuo. The crude product was purified via flash chromatography (DCM/MeOH 2-8%) to yield the 49 mg (40%) of title compound as reddish solid. $^{1}$H NMR (200 MHz, $CDCl_3$/MeOD) δ 9.32 (s, 1H), 8.65 (d, J=1.9 Hz, 1H), 8.17 (d, J=8.9 Hz, 1H), 7.77 (dd, J=8.9, 1.9 Hz, 1H), 7.67-7.48 (m, 5H), 5.07-4.81 (m, 1H), 4.29-4.11 (m, 2H), 3.60-3.40 (m, 2H), 2.75-2.46 (m, 2H), 2.02-1.84 (m, 2H). $^{13}$C NMR (50 MHz, $CDCl_3$/MeOD) δ 155.2, 146.1, 143.9, 137.7, 133.1, 133.0, 131.4, 130.6, 130.3, 129.7, 129.1, 125.2, 120.7, 119.1, 67.4, 55.2, 31.5. ESI-MS m/z: 462.3 $[M+Na+MeOH]^+$ HPLC $t_{ret}$=7.54 min.

Example 1

N,N-Dimethyl-3-((5-(1-(tetrahydro-2H-pyran-4-yl)-1H-imidazo[4,5-c]quinolin-8-yl)pyridin-2-yl)oxy)propan-1-amine

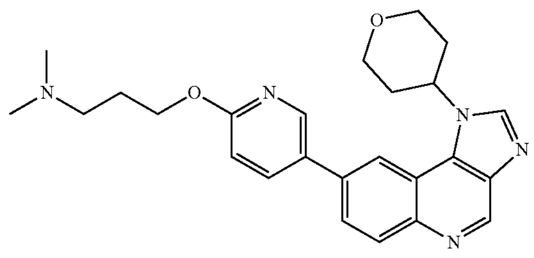 [SMILES: CN(C)CCCOc1ccc(-c2ccc3ncc4ncn(C5CCOCC5)c4c3c2)cn1]

In a screw-top reaction vial, 50 mg (10) (0.15 mmol) and 1 mg $tBu_3P$ Pd G3 (1.5 mol %) were suspended in 3.6 ml degassed dioxane under argon atmosphere. Subsequently were added 57 mg (7) (0.19 mmol) and 0.9 ml of an aqueous 0.5M $K_3PO_4$ solution (0.45 mmol) via syringe. The reaction vial was sealed and heated to 50° C. heatingblock temperature overnight. TLC indicated incomplete conversion at that point and additional boronic ester (20 mg, 0.07 mmol) was added. After another 4 hours, the reaction was quenched by dilution with DCM and brine. The phases were separated and the aqueous phase was further extracted with DCM (4×15 ml). The combined extracts were washed with brine, dried and evaporated. The residue was purified via flash chromatography (DCM/MeOH+2N $NH_3$ 2-8%) to yield the title substance as yellowish oil. The residue was triturated with pentane to afford a white solid, which was isolated by filtration, washed with pentane and dried in vacuo. Yield: 42 mg (65%). $^1H$ NMR (200 MHz, $CDCl_3$) δ 9.31 (s, 1H), 8.45 (d, J=1.9 Hz, 1H), 8.32 (d, J=8.9 Hz, 1H), 8.18 (d, J=8.4 Hz, 2H), 7.95-7.73 (m, 2H), 6.88 (d, J=8.5 Hz, 1H), 5.17-4.93 (m, 1H), 4.41 (t, J=6.4 Hz, 2H), 4.33-4.13 (m, 2H), 3.72 (t, J=11.6 Hz, 2H), 2.57-2.32 (m, 4H), 2.27 (s, 6H), 2.26-2.09 (m, 2H), 2.08-1.85 (m, 2H). $^{13}C$ NMR (50 MHz, $CDCl_3$) δ 163.9, 146.1, 145.3, 144.3, 139.8, 138.4, 137.6, 136.4, 132.4, 132.0, 129.7, 126.3, 118.3, 117.5, 111.5, 67.1, 64.7, 56.5, 55.3, 45.5, 33.9, 27.4. ESI-MS m/z: 432.6 $[M+H]^+$ HPLC $t_{ret}$=1.29 min.

Example 2

N,N-Dimethyl-3-((5-(2-methyl-1-(tetrahydro-2H-pyran-4-yl)-1H-imidazo[4,5-c]quinolin-8-yl)pyridin-2-yl)oxy)propan-1-amine

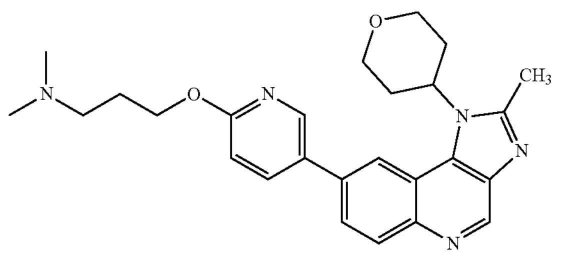

In a screw-top reaction vial, 52 mg (11) (0.15 mmol) and 1 mg $tBu_3P$ Pd G3 (1.5 mol %) were suspended in 3.6 ml degassed dioxane under argon atmosphere. Subsequently were added 57 mg (7) (0.19 mmol) and 0.9 ml of an aqueous 0.5M $K_3PO_4$ solution (0.45 mmol) via syringe. The reaction vial was sealed and heated to 50° C. heatingblock for 4 hours. TLC indicated complete conversion at that point and the reaction was quenched by dilution with EtOAc and brine. The phases were separated and the aqueous phase was further extracted with EtOAc (3×15 ml). The combined extracts were washed with brine, dried and evaporated. The residue was purified via flash chromatography (DCM/MeOH+2N $NH_3$ 2-8%) to yield 51 mg (76%) of the title substance as off-white solid. $^1H$ NMR (400 MHz, $CDCl_3$) δ 9.19 (s, 1H), 8.72-8.33 (m, 2H), 8.28 (d, J=8.6 Hz, 1H), 7.93 (br s, 1H), 7.80 (d, J=8.3 Hz, 1H), 6.86 (d, J=8.6 Hz, 1H), 4.39 (t, J=6.4 Hz, 2H), 4.29 (dd, J=11.2, 3.7 Hz, 2H), 3.64 (td, J=12.1, 1.8 Hz, 2H), 3.00-2.62 (m, 5H), 2.53-2.46 (m, 2H), 2.28 (s, 6H), 2.10-1.86 (m, 4H). $^{13}C$ NMR (101 MHz, $CDCl_3$) δ 163.9, 151.6, 145.5, 145.2, 144.5, 137.5, 137.3, 135.9, 133.9, 132.3, 129.6, 125.4, 119.3, 118.1, 111.4, 67.7, 64.7, 56.5, 54.9, 45.4, 31.4, 27.4, 17.0. ESI-MS m/z: 445.8 $[M+H]^+$ HPLC $t_{ret}$=1.37 min.

Example 3

3-((5-(2-(Furan-2-yl)-1-(tetrahydro-2H-pyran-4-yl)-1H-imidazo[4,5-c]quinolin-8-yl)pyridin-2-yl)oxy)-N,N-dimethylpropan-1-amine

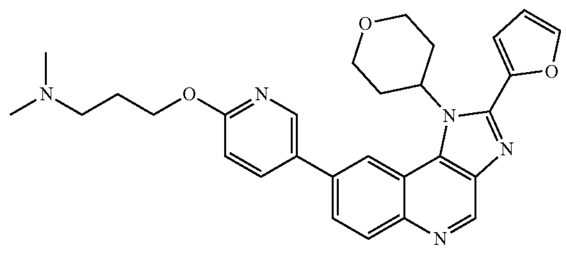 [SMILES: CN(C)CCCOc1ccc(-c2ccc3ncc4nc(-c5ccco5)n(C5CCOCC5)c4c3c2)cn1]

The preparation was carried out as described above for example 2 starting from 36 mg (12) (0.09 mmol). Yield: 26 mg (58%) as yellowish foam. $^1H$ NMR (200 MHz, $CDCl_3$) δ 9.31 (s, 1H), 8.64-8.48 (m, 2H), 8.34 (d, J=8.7 Hz, 1H), 7.98 (dd, J=8.7, 2.6 Hz, 1H), 7.88 (dd, J=8.7, 1.7 Hz, 1H), 7.71 (dd, J=1.7, 0.6 Hz, 1H), 7.13 (dd, J=3.5, 0.6 Hz, 1H), 6.89 (d, J=8.7 Hz, 1H), 6.66 (dd, J=3.5, 1.7 Hz, 1H), 5.44-5.17 (m, 1H), 4.42 (t, J=6.5 Hz, 2H), 4.34-4.15 (m, 2H), 3.72-3.49 (m, 2H), 2.88-2.60 (m, 2H), 2.58-2.43 (m, 2H), 2.29 (s, 6H), 2.12-1.92 (m, 4H). $^{13}C$ NMR (50 MHz, $CDCl_3$) δ 163.9, 145.9, 145.5, 145.1, 144.9, 144.8, 144.5, 137.7, 137.6, 136.1, 134.5, 132.3, 129.4, 125.9, 119.7, 118.3, 114.1, 112.4, 111.5, 67.7, 64.7, 56.5, 55.7, 45.5, 31.1, 27.4. ESI-MS m/z: 498.5 $[M+H]^+$ HPLC $t_{ret}$=3.48 min.

Example 4

N,N-Dimethyl-3-((5-(2-phenyl-1-(tetrahydro-2H-pyran-4-yl)-1H-imidazo[4,5-c]quinolin-8-yl)pyridin-2-yl)oxy)propan-1-amine

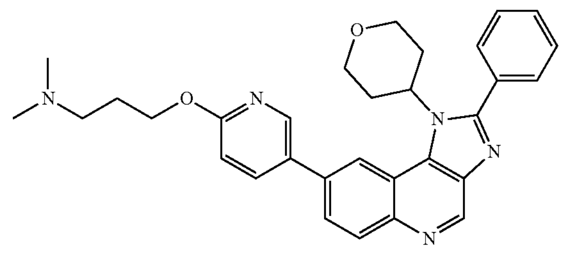 [SMILES: CN(C)CCCOc1ccc(-c2ccc3ncc4nc(-c5ccccc5)n(C5CCOCC5)c4c3c2)cn1]

The preparation was carried out as described above for example 2 starting from 49 mg (13) (0.12 mmol). Yield: 45 mg (74%) as off-white solid. $^1H$ NMR (200 MHz, $CDCl_3$) δ 9.35 (s, 1H), 8.70 (s, 1H), 8.58 (d, J=1.9 Hz, 1H), 8.36 (d, J=8.7 Hz, 1H), 8.02 (dd, J=8.7, 1.9 Hz, 1H), 7.95-7.82 (m, 1H), 7.72-7.46 (m, 5H), 6.88 (d, J=8.5 Hz, 1H), 5.16-4.89 (m, 1H), 4.41 (t, J=6.2 Hz, 2H), 4.22 (dd, J=11.5, 4.7 Hz, 2H), 3.50 (t, J=11.5 Hz, 2H), 2.94-2.65 (m, 2H), 2.50 (t, J=7.4 Hz, 2H), 2.28 (s, 6H), 2.12-1.83 (m, 4H). $^{13}C$ NMR (50 MHz, $CDCl_3$) δ 163.9, 154.8, 146.0, 145.5, 144.7, 137.9, 137.6, 136.0, 134.1, 132.3, 131.5, 130.4, 129.7, 129.3, 129.1, 125.5, 120.4, 118.3, 111.4, 67.4, 64.7, 56.6, 54.6, 45.5, 31.3, 27.4. ESI-MS m/z: 508.6 $[M+H]^+$ HPLC $t_{ret}$=3.76 min.

6-Bromo-N-(2-methoxyethyl)-3-nitroquinolin-4-amine (14)

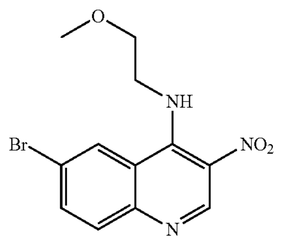

To a suspension of 135 mg (4) (0.5 mmol) in 1 ml DMF were added 107 mg $POCl_3$ (0.7 mmol) at ambient temperature and the mixture was stirred until a dark solution was formed and TLC indicated complete conversion. Excess of 2-methoxyethylamine (315 mg/4.2 mmol) was added in several portions until TLC indicated full consumption of the intermediate and formation of a yellow product. The mixture was diluted with half-sat. $NH_4Cl$ and the precipitate was isolated by filtration and washed with water. Drying at 60° C. in a convection oven afforded 156 mg (96%) of the title substance as yellow solid. According HPLC and NMR the crude product still contains minor amounts of starting material, but the crude product was used without further purification. $^1H$ NMR (200 MHz, DMSO) δ 9.17-9.07 (m, 1H), 9.05 (s, 1H), 8.70 (d, J=1.9 Hz, 1H), 7.95 (dd, J=8.8, 1.9 Hz, 1H), 7.81 (d, J=8.8 Hz, 1H), 3.75 (dd, J=9.4, 4.8 Hz, 2H), 3.62 (t, J=4.8 Hz, 2H), 3.29 (s, 3H). $^{13}C$ NMR (50 MHz, DMSO) δ 147.8, 147.7, 147.3, 135.3, 131.5, 127.9, 126.6, 121.1, 118.7, 70.0, 58.1, 47.3. ESI-MS m/z: 325.9 $[M+H]^+$ HPLC $t_{ret}$=6.47 min.

6-Bromo-$N^4$-(2-methoxyethyl)quinoline-3,4-diamine (15)

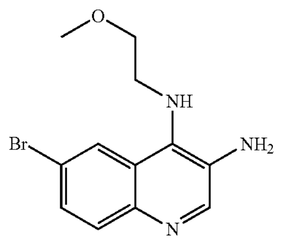 [SMILES: COCCNc1c([N+](=O)[O-])cnc2ccc(Br)cc12]

A suspension of 140 mg (14) (0.43 mmol) and 387 mg $SnCl_2$ dihydrate (1.72 mmol) in 6 ml EtOH was heated to reflux temperature to form a yellow solution. The mixture was stirred until TLC indicated complete conversion (about 2 hours). Then 0.8 g solid $NaHCO_3$ were added and the reaction mixture was concentrated under reduced pressure. EA (20 ml) was added and the mixture was sonicated to break down the agglomerated solids. The suspension was filtered over a bed of celite and the filter cake was washed with additional EA. The filtrate was concentrated under reduced pressure and the residue was purified via flash chromatography (DCM/MeOH 2-8%) to obtain the title substance as colorless oil which solidifies in the freezer. Yield: 51 mg (40%). $^1H$ NMR (200 MHz, $CDCl_3$) δ 8.44 (s, 1H), 8.05 (d, J=1.5 Hz, 1H), 7.78 (d, J=8.8 Hz, 1H), 7.46 (dd, J=8.8, 1.5 Hz, 1H), 4.07 (br s, 3H), 3.39 (s, 3H), 3.34 (s, 4H). $^{13}C$ NMR (50 MHz, $CDCl_3$) δ 143.3, 142.3, 133.3, 133.3, 131.3, 128.9, 126.2, 123.0, 120.4, 71.3, 58.8, 46.5. ESI-MS m/z: 295.8 $[M+H]^+$ HPLC $t_{ret}$=2.98 min.

8-Bromo-1-(2-methoxyethyl)-1H-imidazo[4,5-c]quinolone (16)

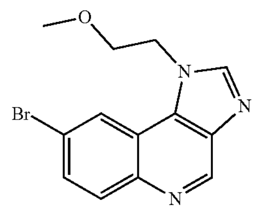 [SMILES: COCCn1cnc2cnc3ccc(Br)cc3c21]

To a solution of 59 mg (15) (0.2 mmol) in 3 ml toluene were added 89 mg triethyl orthoformate (0.6 mmol) and a catalytic amount pTsOH. The reaction vial was sealed and the mixture was heated up to 80° C. oil bath temperature overnight. The solvents were removed under reduced pressure and the residue was purified via flash chromatography (DCM/MeOH 1-10%) to afford 53 mg (87%) of the title substance as white solid. $^1H$ NMR (200 MHz, $CDCl_3$) δ 9.32 (s, 1H), 8.30 (d, J=1.4 Hz, 1H), 8.17 (d, J=8.9 Hz, 1H), 8.05 (s, 1H), 7.76 (dd, J=8.9, 1.4 Hz, 1H), 4.74 (t, J=5.0 Hz, 2H), 3.90 (t, J=5.0 Hz, 2H), 3.33 (s, 3H). $^{13}C$ NMR (50 MHz, $CDCl_3$) δ 145.8, 145.2, 142.9, 138.5, 132.4, 132.2, 130.8, 122.7, 120.8, 119.3, 70.4, 59.4, 47.9. ESI-MS m/z: 305.9 $[M+H]^+$ HPLC $t_{ret}$=3.65 min.

8-Bromo-2-(furan-2-yl)-1-(2-methoxyethyl)-1H-imidazo[4,5-c]quinolone (17)

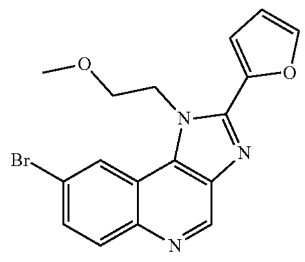 [SMILES: COCCn1c(-c2ccco2)nc2cnc3ccc(Br)cc3c21]

To a solution of 51 mg (15) (0.17 mmol) in 2 ml DMF were added 51 mg furfural (0.21 mmol) at ambient temperature. After 30 min of stirring, 60 μl water and 74 mg oxone (0.12 mmol) were added and stirring was continued at ambient temperature. TLC/MS indicated formation of the condensation intermediate, the desired product as well as several byproducts. The mixture was left stirring at ambient temperature until HPLC indicated the major conversion to the supposed main product (about 5 hours). The reaction was quenched with aqueous $NaHCO_3$ and the aqueous phase was extracted with EtOAc (4×20 ml). The combined extracts were washed with brine, dried over $Na_2SO_4$ and evaporated. The residue was purified via flash chromatography to yield 36 mg (56%) of the title compound as brownish crystals. $^1$H NMR (200 MHz, $CDCl_3$) δ 9.26 (s, 1H), 8.50 (d, J=1.9 Hz, 1H), 8.09 (d, J=8.9 Hz, 1H), 7.70 (dd, J=8.9, 1.9 Hz, 1H), 7.66-7.59 (m, 1H), 7.26 (d, J=3.2 Hz, 1H), 6.62 (dd, J=3.4, 1.8 Hz, 1H), 4.96 (t, J=5.8 Hz, 2H), 3.98 (t, J=5.8 Hz, 2H), 3.33 (s, 3H). $^{13}$C NMR (50 MHz, $CDCl_3$) δ 145.5, 145.5, 144.7, 144.6, 143.4, 137.5, 133.5, 132.5, 130.5, 123.1, 120.7, 119.1, 114.2, 112.3, 71.4, 59.4, 46.9. ESI-MS m/z: 426.1 $[M+Na+MeOH]^+$ HPLC $t_{ret}$=7.50 min.

Example 5

3-((5-(1-(2-Methoxyethyl)-1H-imidazo[4,5-c]quinolin-8-yl)pyridin-2-yl)oxy)-N,N-dimethylpropan-1-amine

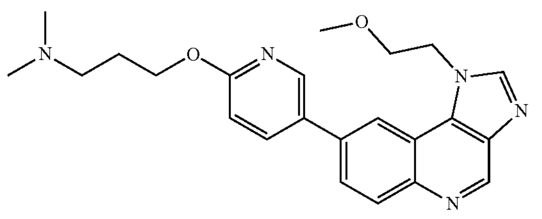 [SMILES: COCCn1cnc2cnc3ccc(-c4ccc(OCCCN(C)C)nc4)cc3c21]

The preparation was carried out as described above for example 2 starting from 37 mg (16) (0.12 mmol) with overnight stirring at 50° C. heatingblock temperature. Flash purification using gradient elution (DCM/MeOH+2N $NH_3$ 4-10%). Yield: 31 mg (64%) as white solid. $^1$H NMR (200 MHz, $CDCl_3$) δ 9.35 (s, 1H), 8.52 (s, 1H), 8.43-8.20 (m, 2H), 8.06 (s, 1H), 8.00-7.77 (m, 2H), 6.92 (d, J=8.5 Hz, 1H), 4.83 (s, 2H), 4.58-4.31 (m, 2H), 4.10-3.84 (m, 2H), 3.35 (s, 3H), 2.63-2.45 (m, 2H), 2.34 (s, 6H), 2.16-1.93 (m, 2H). $^{13}$C NMR (50 MHz, $CDCl_3$) δ 163.8, 145.9, 145.8, 145.5, 144.7, 144.1, 138.5, 137.8, 136.1, 131.7, 129.7, 126.3, 118.5, 117.7, 111.4, 70.6, 64.7, 59.4, 56.5, 48.0, 45.5, 27.4. ESI-MS m/z: 406.1 $[M+H]^+$ HPLC $t_{ret}$=1.30 min.

Example 6

3-((5-(2-(Furan-2-yl)-1-(2-methoxyethyl)-1H-imidazo[4,5-c]quinolin-8-yl)pyridin-2-yl)oxy)-N,N-dimethylpropan-1-amine dimesylate

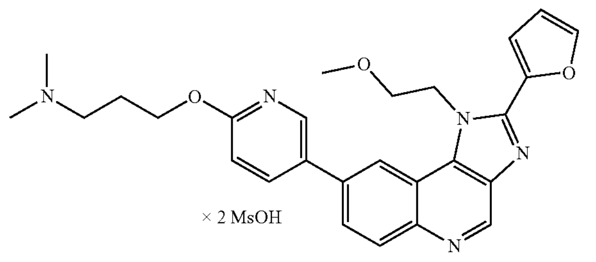 [SMILES: COCCn1c(-c2ccco2)nc2cnc3ccc(-c4ccc(OCCCN(C)C)nc4)cc3c21]

The preparation was carried out as described above for example 2 starting from 31 mg (17) (0.08 mmol) with overnight stirring at 50° C. heatingblock temperature. Flash purification using gradient elution (DCM/MeOH+2N $NH_3$ 1-8%). The product appeared as sticky residue and was therefore converted to the mesylate salt by treatment with 0.25 M MsOH in THF under sonication. The precipitate was filtered off and washed with pentane/THF (2:1) to yield 23 mg (42%) as the dimesylate salt (according to NMR) of the title compound. $^1$H NMR (200 MHz, DMSO) δ 9.82 (s, 1H), 9.47 (br s, 1H), 8.95 (s, 1H), 8.75 (d, J=1.9 Hz, 1H), 8.50-8.37 (m, 2H), 8.32 (dd, J=8.9, 2.2 Hz, 1H), 8.21-8.09 (m, 1H), 7.53 (d, J=3.4 Hz, 1H), 7.06 (d, J=8.7 Hz, 1H), 6.95-6.82 (m, 1H), 5.48-5.17 (m, 2H), 4.43 (t, J=5.8 Hz, 2H), 4.13-4.01 (m, 2H), 3.34-3.22 (m, 2H), 3.19 (s, 3H), 2.85 (d, J=4.8 Hz, 6H), 2.37 (s, 6H), 2.26-2.07 (m, 2H). $^{13}$C NMR (50 MHz, DMSO) δ 163.3, 148.8, 146.8, 145.8, 142.9, 139.6, 139.5, 138.4, 137.2, 135.7, 135.0, 129.5, 128.0, 123.5, 119.5, 117.2, 116.2, 112.7, 111.2, 70.8, 63.1, 58.7, 54.3, 42.4, 39.8, 25.2, 23.9. ESI-MS m/z: 472.2 $[M+H]^+$ HPLC $t_{ret}$=1.74 min.

Preparation of compounds of formula (I), wherein $R^1$ is X—C(=O)—$NR^{11}$—

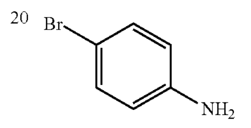

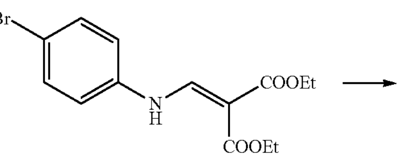

(18)

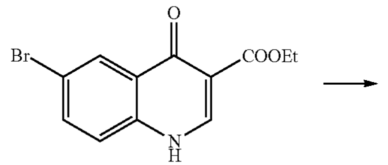

(19)

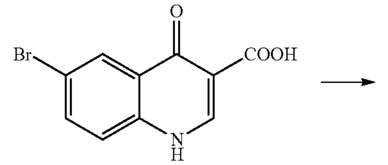

(20)

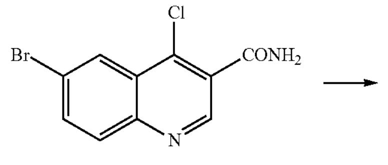

(21)

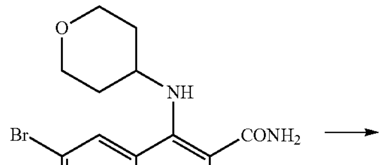

(22)

-continued

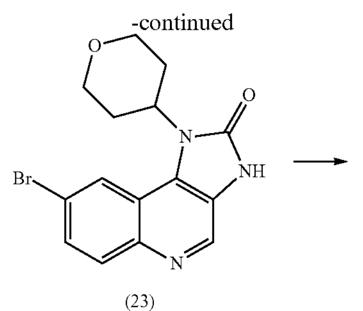

(23)

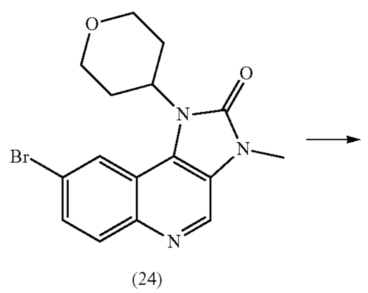

(24)

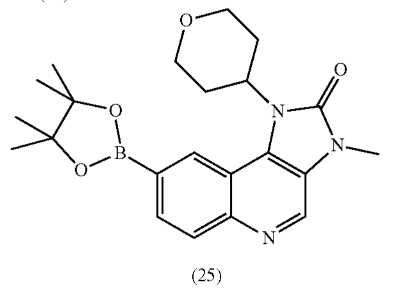

(25)

The main intermediates (21) and (24) were prepared following procedures and methods previously described in WO/2015/170081 starting from 4-bromoaniline. The building block (25) was readily accessible via Miyaura borylation of (24).

Diethyl 2-(((4-bromophenyl)amino)methylene)malonate (18)

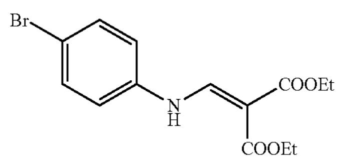 [SMILES: CCOC(=O)C(=CNc1ccc(Br)cc1)C(=O)OCC]

A solution of 21.5 g 4-bromoaniline (125 mmol) and 37.8 g diethyl 2-(ethoxymethylene)malonate (175 mmol) in 210 ml EtOH was refluxed overnight. TLC indicated full conversion and the yellow reaction mixture was cooled in an ice/water bath. The precipitate was collected by filtration and washed with cold hexane. The product was dried at 60° C. in vacuo to afford 38.6 g (90%) of the title compound as white crystalline solid. $^1$H NMR (200 MHz, DMSO) δ 10.65 (d, J=13.6 Hz, 1H), 8.34 (d, J=13.6 Hz, 1H), 7.54 (d, J=8.9 Hz, 2H), 7.34 (d, J=8.9 Hz, 2H), 4.29-4.03 (m, 4H), 1.31-1.15 (m, 6H). $^{13}$C NMR (50 MHz, DMSO) δ 167.2, 164.9, 150.7, 138.9, 132.3, 119.7, 116.5, 94.0, 59.7, 59.6, 14.3, 14.2. ESI-MS m/z: 363.6 [M+Na]$^+$ HPLC $t_{ret}$=9.20 min.

Ethyl 6-bromo-4-oxo-1,4-dihydroquinoline-3-carboxylate (19)

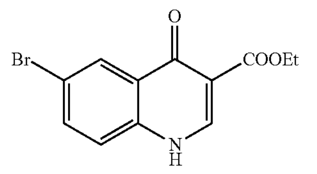 [SMILES: CCOC(=O)c1c[nH]c2ccc(Br)cc2c1=O]

A suspension of 38.4 g (18) (112 mmol) in 200 ml diphenylether was heated up to 220° C. internal temperature and stirring was continued for 30 hours. The reaction mixture was then cooled to room temperature and diluted with 200 ml $Et_2O$. The precipitate was isolated by filtration and washed successively with EtOH and $Et_2O$. The filter cake was dried in a vacuum oven at 60° C. overnight to yield 26.4 g (80%) of the title compound as off-white crystalline solid.

ESI-MS m/z: 317.7 [M+Na]$^+$

6-Bromo-4-oxo-1,4-dihydroquinoline-3-carboxylic acid (20)

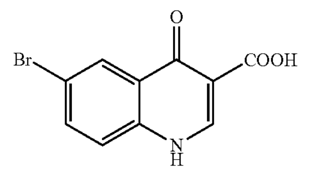

To a suspension od 15.2 g (19) (51.2 mmol) in in 77 ml EtOH were added 77 ml aqueous NaOH (2N) at ambient temperature. The mixture was heated to reflux for 3 hours and was then concentrated to approx. 50% of the starting volume. The yellow solution was diluted with water and cooled with an ice bath. The mixture was acidified to pH 2 with hydrochloric acid to precipitate the product. The resulting suspension was stirred for ten minutes at low temperature and was then filtered via a buchner funnel. The filter cake was washed with $H_2O$ and dried in a convection oven at 80° C. to yield 13.5 g (99%) of the title compound as white solid. $^1$H NMR (200 MHz, DMSO) δ 14.97 (br s, 1H), 13.56 (br s, 1H), 8.90 (s, 1H), 8.30 (d, J=2.3 Hz, 1H), 8.00 (dd, J=8.9, 2.3 Hz, 1H), 7.75 (d, J=8.9 Hz, 1H)$^{13}$C NMR (50 MHz, DMSO) δ 177.1, 166.0, 145.6, 138.4, 136.6, 127.1, 125.9, 122.1, 119.0, 108.1. ESI-MS m/z: 265.6 [M−]$^-$ HPLC $t_{ret}$=6.16 min.

6-Bromo-4-chloroquinoline-3-carboxamide (21)

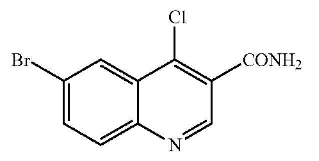 [SMILES: NC(=O)c1cnc2ccc(Br)cc2c1Cl]

To a suspension of 13.5 g (20) (50 mmol) in 80 ml $SOCl_2$ was added a catalytic amount of DMF (400 μl) at ambient temperature. Upon warming an exothermic event was observed starting at about 35° C. After attenuation of the reaction, the temperature was gradually increased to reflux conditions. The thick suspension transformed to a clear yellow solution and refluxing was continued for 4 hours. The majority of thionyl chloride was removed by destillation under normal pressure and subsequently the residue was azeotroped twice with 25 ml dry toluene under reduced pressure to yield the acid chloride as yellowish crystalline solid. The solid was dried in the high vacuum for 30 min to remove residual solvents before it was added portionwise to 150 ml ice-cooled aqueous $NH_3$ solution (25% wt). The resulting suspension was stirred for another 30 min at ambient temperature. The solids were collected by vacuum filtration, washed with water and dried in an oven at 75° C. The title compound obtained as off-white amorphous solid. Yield: 14.2 g (99%). $^1$H NMR (200 MHz, DMSO) δ 8.91 (s, 1H), 8.46-8.37 (m, 1H), 8.25 (br s, 1H), 8.11-7.96 (m, 3H). $^{13}$C NMR (50 MHz, DMSO) δ 166.0, 149.2, 146.6, 136.6, 134.4, 131.7, 130.8, 126.4, 126.2, 122.2. HPLC $t_{ret}$=5.86 min.

6-Bromo-4-((tetrahydro-2H-pyran-4-yl)amino)quinoline-3-carboxamide (22)

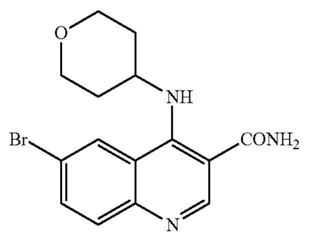 [SMILES: NC(=O)c1cnc2ccc(Br)cc2c1NC1CCOCC1]

To a solution of 6.41 g (21) (22.4 mmol) in 45 ml dry DMF were added 4.7 ml $Et_3N$ (33.7 mmol) and 2.50 g 4-aminotetrahydropyran (24.7 mmol) at ambient temperature. The flask was sealed and the reaction was heated to 85-90° C. heating block temperature. After stirring overnight, the starting material was consumed and the reaction was quenched by dropwise addition of 50 ml half saturated $NH_4Cl$ solution to the hot solution. The resulting suspension was stirred until cooled to ambient temperature and was further diluted with 200 ml water. The suspension was cooled with ice and stirring was continued for 30 min. The solids were collected by filtration, washed with water and dried in vacuo at 75° C. to afford 6.84 g (87%) of the title compound as greyish fine needles. $^1$H NMR (200 MHz, DMSO) δ 8.59 (s, 1H), 8.55-8.47 (m, 1H), 8.13 (br s, 1H), 7.91 (d, J=8.9 Hz, 1H), 7.84-7.71 (m, 2H), 7.62 (br s, 1H), 4.09-3.94 (m, 1H), 3.93-3.78 (m, 2H), 3.36-3.24 (m, 2H), 1.99-1.83 (m, 2H), 1.71-1.46 (m, 2H). $^{13}$C NMR (50 MHz, DMSO) δ 170.7, 150.3, 149.2, 147.7, 132.9, 131.4, 126.0, 121.6, 117.7, 111.3, 65.9, 51.9, 33.5. ESI-MS m/z: 349.9 $[M+H]^+$ HPLC $t_{ret}$=2.22 min.

8-Bromo-1-(tetrahydro-2H-pyran-4-yl)-1,3-dihydro-2H-imidazo[4,5-c]quinolin-2-one (23)

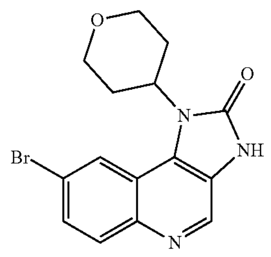 [SMILES: O=c1[nH]c2cnc3ccc(Br)cc3c2n1C1CCOCC1]

To a suspension of 6.49 g (22) (18.5 mmol) in 100 ml MeOH was added 5.5 ml 1,8-diazabicyclo[5.4.0]undec-7-ene (37.1 mmol). The mixture was cooled with ice/water and 2.15 g trichloroisocyanuric acid (9.3 mmol) was added as solid in one portion. The reaction was stirred for 30 min with cooling and two hours at ambient temperature. TLC indicated complete conversion at this point and the suspension was diluted with 100 ml water and stirred for another hour under ice cooling. The solids were collected by filtration, washed with diluted $NaHCO_3$ and water. The filter cake was finally dried in vacuo at 80° C. to afford the title compound as beige solid. $^1$H NMR (200 MHz, DMSO) δ 11.85 (br s, 1H), 8.74 (s, 1H), 8.42 (d, J=1.8 Hz, 1H), 8.00 (d, J=9.0 Hz, 1H), 7.78 (dd, J=9.0, 1.8 Hz, 1H), 5.07-4.79 (m, 1H), 4.03 (dd, J=11.2, 4.2 Hz, 2H), 3.57 (t, J=11.2 Hz, 2H), 2.67 (qd, J=12.5, 4.7 Hz, 2H), 1.85 (dd, J=12.5, 2.4 Hz, 2H). ESI-MS m/z: 345.9 $[M-H]^+$ HPLC $t_{ret}$=6.56 min.

8-Bromo-3-methyl-1-(tetrahydro-2H-pyran-4-yl)-1,3-dihydro-2H-imidazo[4,5-c]quinolin-2-one (24)

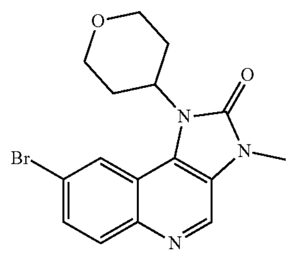 [SMILES: Cn1c(=O)n(C2CCOCC2)c2c3cc(Br)ccc3ncc21]

To a suspension of 3.48 g (23) (10 mmol) in 50 ml dry DMF was added 600 mg NaH (60% wt dispersion in mineral oil, 15 mmol) portionwise at ambient temperature. After 20 min, 1.99 g Mel (14 mmol) were added dropwise to the mixture and stirring was continued at ambient temperature for 90 min. The mixture was diluted with water and stirred under ice-cooling for 30 min. The solids were collected by filtration, washed with water and dried at 90° C. in a convection oven to obtain 3.53 g (98%) of the title compound as off-white solid. $^1$H NMR (200 MHz, $CDCl_3$) δ 8.66 (s, 1H), 8.32 (d, J=1.9 Hz, 1H), 7.97 (d, J=9.0 Hz, 1H), 7.65 (dd, J=9.0, 1.9 Hz, 2H), 5.00-4.77 (m, 2H), 4.28-4.12 (m, 2H), 3.67-3.49 (m, 5H), 3.01-2.75 (m, 2H), 1.95-1.78 (m, 2H). $^{13}$C NMR (50 MHz, $CDCl_3$) δ 153.5, 143.6, 132.6, 132.5, 130.4, 128.2, 123.6, 123.3, 120.9, 116.6, 67.7, 53.9, 30.1, 27.5. HPLC $t_{ret}$=6.80 min.

3-Methyl-1-(tetrahydro-2H-pyran-4-yl)-8-(4,4,5,5-tetramethyl-1,3,2-dioxaborolan-2-yl)-1,3-dihydro-2H-imidazo[4,5-c]quinolin-2-one (25)

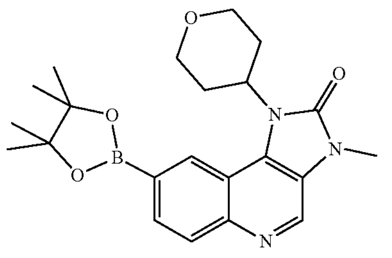

In an oven dried schlenk flask were combined 724 mg (24) (2 mmol), 523 mg bis(pinacolato)diboron (2.06 mmol), 589 mg KOAc (6 mmol) and 49 mg Pd(dppf)$Cl_2$×DCM (0.06 mmol) under inert atmosphere and 14 ml degassed dioxane were added. The mixture was heated to 75° C. oil bath temperature for 24 hours. The brown suspension was diluted with EtOAc and filtered over celite. The filtrate was concentrated under reduced pressure and the residue purified via flash chromatography (DCM/MeOH 2-6%). Yield: 435 mg (53%) as white solid. $^1$H NMR (400 MHz, $CDCl_3$) δ 8.74 (s, 1H), 8.71 (s, 1H), 8.12 (d, J=8.2 Hz, 1H), 7.94 (d, J=8.2 Hz, 1H), 5.12-4.96 (m, 1H), 4.23 (dd, J=11.6, 4.0 Hz, 2H), 3.68-3.58 (m, 2H), 3.55 (s, 3H), 2.96 (qd, J=12.5, 4.0 Hz, 2H), 1.98 (d, J=12.5 Hz, 2H), 1.38 (s, 12H). $^{13}$C NMR (101 MHz, $CDCl_3$) δ 153.6, 146.5, 132.8, 132.7, 131.5, 130.0, 129.8, 129.0, 123.1, 115.1, 84.4, 67.9, 55.0, 30.7, 27.4, 25.1, 25.0.

Pyridinylureas were accessible via a two-step sequence including oxidation and Curtius rearrangement starting from (5-bromopyridin-2-yl)methanol, finally resulting in examples 7 and 8 by Suzuki coupling with (25)

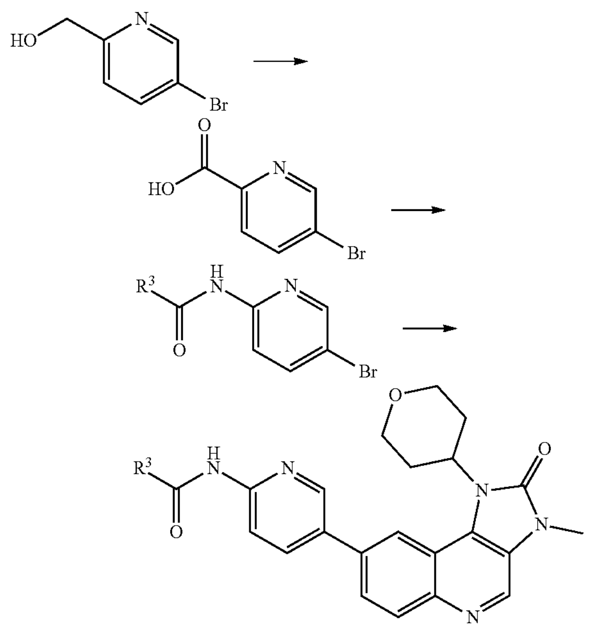

(5-Bromopyridin-2-yl)carboxylic acid (26)

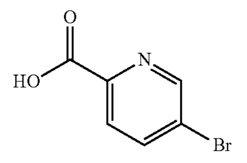

To an suspension of 376 mg (5-bromopyridin-2-yl)methanol (2 mmol) in 10 ml aqueous $Na_2CO_3$ (0.2 M) were added 442 mg $KMnO_4$ (2.8 mmol) as solid in one portion. The mixture was stirred at ambient temperature for about 2 hours until TLC indicated full consumption of starting material. The reaction was quenched by addition of 0.5 ml formalin and stirring was continued for additional 10 min. Then the mixture was filtered over celite and the solids were washed with aqueous $Na_2CO_3$. The filtrate was carefully acidified with HCl and the resulting thick suspension was stirred for about 30 min on ice for better agglomeration of the precipitate. The solids were filtered off, washed with water and dried in vacuo (1st crop, 245 mg). To yield a second crop, the filtrate was extracted with EtOAc (3×15 ml). The combined extracts were washed with brine, dried and evaporated to yield another 80 mg as white crystalline solid (2nd crop). Total yield: 325 mg (80%). $^1$H NMR (200 MHz, DMSO) δ 13.40 (br s, 1H), 8.83 (d, J=2.2 Hz, 1H), 8.23 (dd, J=8.3, 2.2 Hz, 1H), 7.97 (d, J=8.3 Hz, 1H). $^{13}$C NMR (50 MHz, DMSO) δ 165.5, 150.4, 147.1, 140.1, 126.4, 124.1. HPLC $t_{ret}$=3.50 min.

1-(5-Bromopyridin-2-yl)-3-(2-(dimethylamino)ethyl) urea (27)

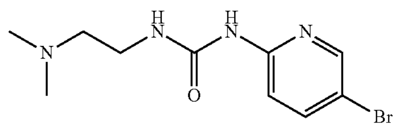 [SMILES: CN(C)CCNC(=O)Nc1ccc(Br)cn1]

To a solution of 81 mg (26) (0.4 mmol) and 49 mg $Et_3N$ (0.48 mmol) in 3 ml toluene was added 110 mg diphenyl phosphorylazide (0.4 mmol). The mixture was stirred at ambient temperature for 30 min and was then heated up to 80° C. heating block temperature for one hour. After cooling to ambient temperature, 53 mg N,N-dimethylethylendiamine (0.6 mmol) were added and stirring was continued at 60° C. overnight. HPLC indicated full consumption of starting material and the reaction mixture was poured on half saturated $NaHCO_3$ solution. The aqueous phase was extracted with EtOAc (4×15 ml) and subsequently the combined extracts were washed with brine, dried and evaporated. The residue was purified via flash chromatography (DCM/MeOH+2N $NH_3$ 2-8%). The title compound was obtained as yellow semi-solid, which solidified upon standing. Yield: 50 mg (44%). $^1$H NMR (200 MHz, $CDCl_3$) δ 9.86 (br s, 1H), 9.00 (br s, 1H), 8.17 (d, J=1.9 Hz, 1H), 7.61 (dd, J=8.7, 1.9 Hz, 1H), 6.93 (d, J=8.7 Hz, 1H), 3.57-3.34 (m, 2H), 2.51 (t, J=6.3 Hz, 2H), 2.29 (s, 6H). $^{13}$C NMR (50 MHz, $CDCl_3$) δ 156.4, 152.5, 146.9, 140.6, 113.8, 111.5, 58.8, 45.6, 38.0. ESI-MS m/z: 309.2 $[M+Na]^+$ HPLC $t_{ret}$=2.11 min.

N-(5-Bromopyridin-2-yl)-4-methylpiperazine-1-carboxamide (28)

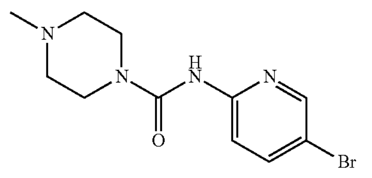 [SMILES: CN1CCN(C(=O)Nc2ccc(Br)cn2)CC1]

The synthesis was carried out using the same procude as described above for (27) but using 60 mg N-methylpiperazine (0.6 mmol) to quench the isocyanate intermediate. Yield: 55 mg as yellow semi-solid. $^{1}$H NMR (200 MHz, $CDCl_3$) δ 8.17 (d, J=1.8 Hz, 1H), 7.92 (d, J=8.9 Hz, 1H), 7.68 (dd, J=8.9, 1.8 Hz, 1H), 7.49 (br s, 1H), 3.50 (t, J=4.9 Hz, 4H), 2.40 (t, J=4.9 Hz, 4H), 2.28 (s, 3H). $^{13}$C NMR (50 MHz, $CDCl_3$) δ 153.8, 151.6, 148.2, 140.5, 114.7, 113.1, 54.6, 46.0, 44.0. ESI-MS m/z: 321.2 $[M+Na]^+$ HPLC $t_{ret}$=1.95 min.

Example 7

1-(2-(Dimethylamino)ethyl)-3-(5-(3-methyl-2-oxo-1-(tetrahydro-2H-pyran-4-yl)-2,3-dihydro-H-imidazo[4,5-c]quinolin-8-yl)pyridin-2-yl)urea

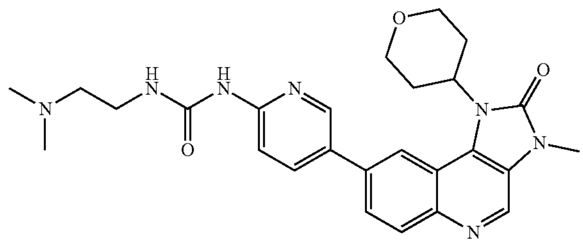

In a screw-top reaction vial, 41 mg (25) (0.1 mmol) and 1 mg $tBu_3P$ Pd G3 (1.5 mol %) were suspended in 2.4 ml degassed dioxane under argon atmosphere. Subsequently were added 40 mg (27) (0.14 mmol) as solution in dioxane and 0.6 ml of an aqueous 0.5M $K_3PO_4$ solution (0.3 mmol) via syringe. The reaction vial was sealed and heated to 50° C. heating block temperature for about 2 hours. TLC indicated complete conversion at that point and the reaction was quenched by dilution with EtOAc and brine. The phases were separated and the aqueous phase was further extracted with EtOAc (3×15 ml) and subsequently with DCM (4×15 ml). The combined extracts were washed with brine, dried and evaporated. The residue was purified via flash chromatography (DCM/MeOH+2N $NH_3$ 2-10%) to obtain 36 mg (74%) of the title substance as white solid. The free base of this compound showed very low solubility in DMSO (<10 mM). Therefore, it was converted to the HCl salt by dissolution in DCM/MeOH, acidification with HCl in EtOH and subsequent concentration of the solution. The residue was triturated with pentane and the precipitate was isolated by filtration to yield the hydrochloride as slightly yellowish solid. $^{1}$H NMR (freebase) (200 MHz, $CDCl_3$/MeOD) δ 8.56 (s, 1H), 8.42 (d, J=2.2 Hz, 1H), 8.28 (s, 1H), 8.06 (d, J=8.9 Hz, 1H), 7.85 (dd, J=8.6, 2.2 Hz, 1H), 7.72 (dd, J=8.9, 1.4 Hz, 1H), 7.13 (d, J=8.6 Hz, 1H), 5.10-4.83 (m, 1H), 4.18-4.04 (m, 2H), 3.62-3.42 (m, 5H), 3.36 (t, J=6.6 Hz, 2H), 2.95-2.66 (m, 2H), 2.50 (t, J=6.6 Hz, 2H), 2.23 (s, 6H), 1.95-1.73 (m, 2H). $^{13}$C NMR (freebase) (50 MHz, $CDCl_3$/MeOD) δ 155.9, 153.7, 152.7, 144.7, 144.2, 136.8, 135.8, 132.2, 131.3, 129.3, 129.2, 125.9, 123.5, 118.4, 115.8, 112.3, 67.5, 58.5, 53.1, 44.9, 37.2, 30.0, 27.3. $^{1}$H NMR (hydrochloride salt) (400 MHz, DMSO) δ 10.59 (br s, 1H), 10.09 (s, 1H), 9.39 (s, 1H), 8.76 (s, 1H), 8.67-8.50 (m, 2H), 8.42-8.29 (m, 2H), 8.22 (br s, 1H), 7.75 (d, J=8.7 Hz, 1H), 5.40-5.21 (m, 1H), 4.11-4.02 (m, 2H), 3.69-3.58 (m, 4H), 3.57 (s, 3H), 3.30-3.15 (m, 2H), 2.81 (d, J=4.5 Hz, 6H), 2.76-2.61 (m, 2H), 2.06-1.91 (m, 2H). ESI-MS m/z: 490.6 $[M+H]^+$ HPLC $t_{ret}$=1.31 min.

Example 8

4-Methyl-N-(5-(3-methyl-2-oxo-1-(tetrahydro-2H-pyran-4-yl)-2,3-dihydro-1H-imidazo[4,5-c]quinolin-8-yl)pyridin-2-yl)piperazine-1-carboxamide

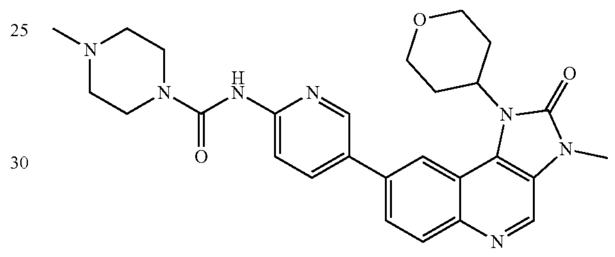

The synthesis was carried out using the same procedure as for example 2 but with 42 mg (28) as arylbromide starting material in the Suzuki coupling. $^{1}$H NMR (freebase) (200 MHz, $CDCl_3$/MeOD) δ 8.59 (s, 1H), 8.47 (d, J=1.3 Hz, 1H), 8.40-8.27 (m, 1H), 8.15-7.98 (m, 2H), 7.93 (dd, J=8.8, 2.1 Hz, 1H), 7.76 (dd, J=8.8, 1.3 Hz, 1H), 5.11-4.88 (m, 1H), 4.22-4.04 (m, 2H), 3.63-3.37 (m, 9H), 2.95-2.68 (m, 2H), 2.64-2.39 (m, 4H), 2.30 (s, 3H), 1.96-1.75 (m, 2H). $^{13}$C NMR (freebase) (50 MHz, $CDCl_3$/MeOD) δ 154.2, 153.6, 152.5, 145.5, 144.2, 136.7, 135.7, 132.1, 131.1, 130.4, 129.2, 125.8, 123.4, 118.5, 115.7, 113.7, 67.4, 54.2, 52.9, 45.3, 43.3, 29.9, 27.2. $^{1}$H NMR (hydrochloride salt) (400 MHz, DMSO) δ 11.43 (br s, 1H), 9.99 (br s, 1H), 9.33 (s, 1H), 8.83 (s, 1H), 8.62 (s, 1H), 8.53 (d, J=8.6 Hz, 1H), 8.39-8.25 (m, 2H), 8.01 (d, J=8.6 Hz, 1H), 5.43-5.22 (m, 1H), 4.38-4.26 (m, 2H), 4.14-3.99 (m, 2H), 3.68-3.59 (m, 2H), 3.57 (s, 3H), 3.47-3.30 (m, 4H), 3.13-2.97 (m, 2H), 2.77 (s, 3H), 2.75-2.63 (m, 2H), 2.08-1.92 (m, 2H). ESI-MS m/z: 524.6 $[M+Na]^+$ HPLC $t_{ret}$=1.27 min.

The main intermediate (29) used in some of the following examples was accessible via the same methodology as already described above for the preparation of (25):

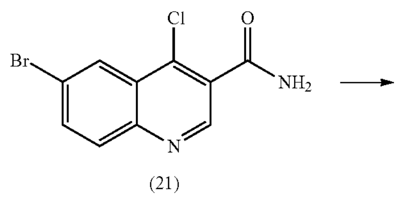

(21)

-continued

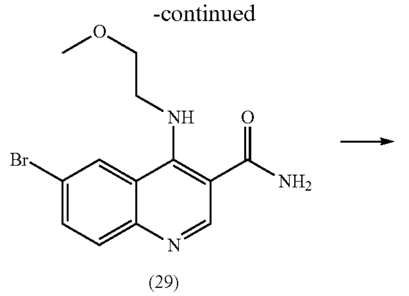

(29)

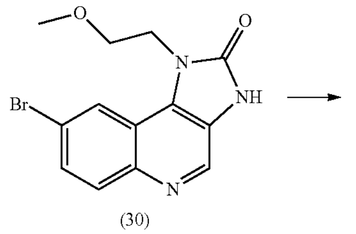

(30)

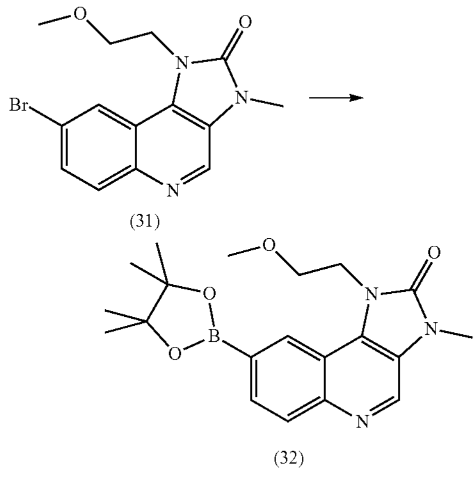

(31)

(32)

6-Bromo-4-((2-methoxyethyl)amino)quinoline-3-carboxamide (29)

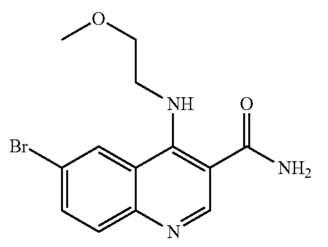 [SMILES: COCCNc1c(C(N)=O)cnc2ccc(Br)cc12]

To a solution of 8.0 g (21) (28 mmol) in 50 ml dry DMF was added 5.26 g 2-methoxyethylamine (70 mmol) at ambient temperature. The flask was sealed and the reaction was heated to 100° C. heating block temperature. After stirring for about one hour the starting material was consumed (TLC) and the reaction was quenched by the dropwise addition of 120 ml half saturated $NH_4Cl$ solution to the hot solution. The mixture was cooled to ambient temperature and was further diluted with water. After additional 30 min of stirring under ice-cooling, the solids were collected by filtration, washed with water and dried at 75° C. in a convection oven to afford 8.60 g (95%) of the title compound as white solid. $^1H$ NMR (200 MHz, DMSO) δ 8.60 (s, 1H), 8.56-8.41 (m, 2H), 8.07 (br s, 1H), 7.82-7.68 (m, 2H), 7.48 (br s, 1H), 3.72-3.61 (m, 2H), 3.56 (t, J=5.3 Hz, 2H), 3.27 (s, 3H). $^{13}C$ NMR (50 MHz, DMSO) δ 170.5, 150.6, 150.3, 147.8, 132.9, 131.3, 126.4, 121.0, 117.0, 109.4, 70.8, 58.1, 46.1. ESI-MS m/z: 323.9 $[M+H]^+$ HPLC $t_{ret}$=1.46 min.

8-Bromo-1-(2-methoxyethyl)-1,3-dihydro-2H-imidazo[4,5-c]quinolin-2-one (30)

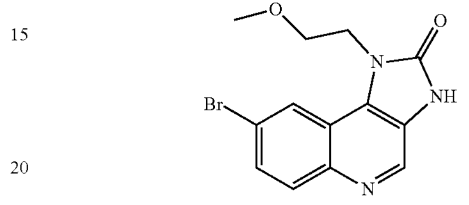

To a suspension of 8.60 g (29) (26.5 mmol) in 140 ml MeOH was added 8.08 g 1,8-diazabicyclo[5.4.0]undec-7-ene (53.1 mmol). The mixture was cooled with ice/water and 3.39 trichloroisocyanuric acid (14.6 mmol) were added as solid in one portion. The reaction was stirred for 15 min with cooling and 120 min at ambient temperature. TLC indicated complete conversion and the white suspension was diluted with water and stirred for additional 30 min under ice cooling. The solids were collected by filtration, washed with water and dried in a convection oven at 75° C. The title compound was obtained as white solid. Yield: 8.40 g (98%). $^1H$ NMR (200 MHz, DMSO) δ 11.66 (br s, 1H), 8.68 (s, 1H), 8.42 (d, J=2.0 Hz, 1H), 7.92 (d, J=9.0 Hz, 1H), 7.70 (dd, J=9.0, 2.0 Hz, 1H), 4.41 (t, J=5.4 Hz, 2H), 3.69 (t, J=5.4 Hz, 2H), 3.22 (s, 3H). $^{13}C$ NMR (50 MHz, DMSO) δ 154.0, 142.6, 134.4, 132.2, 129.5, 128.8, 123.3, 122.0, 119.1, 116.4, 70.1, 58.4, 41.9. ESI-MS m/z: 321.9 $[M+H]^+$ HPLC $t_{ret}$=3.87 min.

8-Bromo-1-(2-methoxyethyl)-3-methyl-1,3-dihydro-2H-imidazo[4,5-c]quinolin-2-one (31)

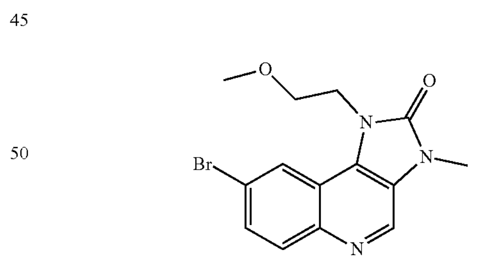

To a suspension of 8.4 g (30) (26 mmol) in 150 ml dry DMF was added 1.56 g NaH (60% dispersion in mineral oil, 39.1 mmol) portionwise at ambient temperature. After 20 min, 4.44 g MeI (31.3 mmol) were added to dropwise to the mixture and stirring was continued at ambient temperature until TLC indicated complete conversion. The reaction was quenched with 100 ml half-sat. NH4Cl and further diluted with water after gas evolution ceased. Stirring was continued under ice-cooling for 30 min and the solids were collected by filtration, washed with water and dried in a convection oven at 75° C. to obtain 7.40 g (84%) of the title compound as off-white solid. $^1H$ NMR (200 MHz, $CDCl_3$)

δ 8.68 (s, 1H), 8.42 (d, J=1.8 Hz, 1H), 7.97 (d, J=9.1 Hz, 1H), 7.64 (dd, J=9.1, 1.8 Hz, 1H), 4.48 (t, J=5.4 Hz, 2H), 3.80 (t, J=5.4 Hz, 2H), 3.60 (s, 3H), 3.33 (s, 3H). $^{13}C$ NMR (50 MHz, $CDCl_3$) δ 154.1, 143.5, 132.3, 132.1, 130.6, 129.0, 123.5, 123.3, 120.5, 116.7, 70.7, 59.3, 43.5, 27.9. ESI-MS m/z: 336.0 $[M+H]^+$ HPLC $t_{ret}$=4.30 min.

1-(2-Methoxyethyl)-3-methyl-8-(4,4,5,5-tetramethyl-1,3,2-dioxaborolan-2-yl)-1,3-dihydro-2H-imidazo[4,5-c]quinolin-2-one (32)

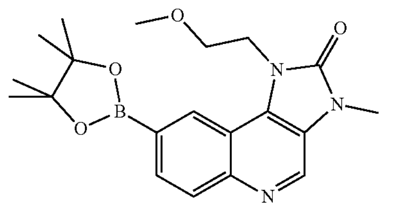

In an oven dried schlenk flask were combined 4.0 g (31) (11.9 mmol), 3.11 g bis(pinacolato)diboron (12.3 mmol) and 3.50 g KOAc (35.7 mmol) under inert atmosphere. Degassed dioxane was added and the suspensions was degassed via several vacuum/argon cycles. Then, 261 mg $Pd(dppf)Cl_2$ (0.36 mmol) were added and the degassing procedure was repeated. The reaction mixture was then heated up to 85° C. oil-bath temperature and stirred overnight. TLC indicated complete conversion at this point and the dark reaction mixture was diluted with EtOAc and filtered over celite. Activated carbon was added and the filtrate was heated to reflux for about 45 min. After filtration over celite, the filtrate was concentrated under reduced pressure. The crude product was triturated with heptane and stored in the freezer for several hours. The solids were isolated by filtration and washed with heptane and pentane. The filter cake was dried in a convection oven at 60° C. and the title substance was obtained as greyish solid. For further purification, the crude product was suspended in acetonitrile (8-10 ml/g) and heated to 60° C. oil-bath temperature for several hours until a uniform suspension was formed. After cooling back to ambient temperature and cooling in an ice bath, the solids were isolated by filtration and washed with cold acetonitrile to afford the title compound as white solid. Yield 4.1 g (90%). $^1H$ NMR (200 MHz, $CDCl_3$) δ 8.82-8.67 (m, 2H), 8.12 (d, J=8.6 Hz, 1H), 7.97 (dd, J=8.6, 0.8 Hz, 1H), 4.62 (t, J=6.0 Hz, 2H), 3.86 (t, J=6.0 Hz, 2H), 3.60 (s, 3H), 3.39 (s, 3H), 1.38 (s, 12H). $^{13}C$ NMR (50 MHz, $CDCl_3$) δ 154.3, 146.0, 132.4 (2C), 132.1, 130.5, 129.0, 128.9, 123.0, 115.1, 84.4, 70.2, 59.2, 43.2, 27.9, 25.0. HPLC $t_{ret}$=1.42 min.

Example 9

8-(6-(3-(Dimethylamino)propoxy)43uinolin-3-yl)-1-(2-methoxyethyl)-3-methyl-1,3-dihydro-2H-imidazo[4,5-c]43uinoline-2-one

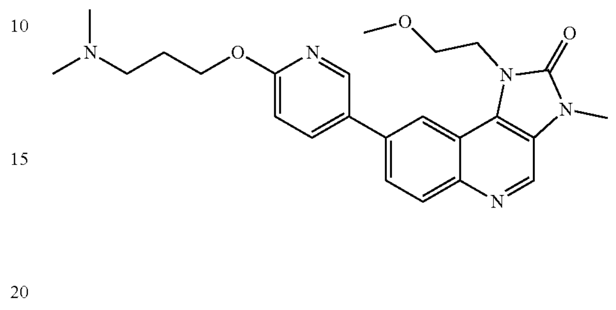

In a screw-top reaction vial, 40 mg (31) (0.12 mmol) and 1.4 mg $tBu_3P$ Pd G3 (2 mol %) were suspended in 2.9 ml degassed dioxane under argon atmosphere. Subsequently were added 59 mg (7) (0.19 mmol) and 0.72 ml of an aqueous 0.5M $K_3PO_4$ solution (0.36 mmol) via syringe. The reaction vial was sealed and heated to 50° C. heatingblock and stirring was continued overnight. TLC indicated complete conversion at that point and the reaction was quenched by dilution with EtOAc and brine. The phases were separated and the aqueous phase was further extracted with EtOAc (3×15 ml). The combined extracts were washed with brine, dried and evaporated. The residue was purified via flash chromatography (DCM/MeOH+2N $NH_3$ 4-10%) to yield 35 mg (67%) of the title substance as white solid. $^1H$ NMR (200 MHz, $CDCl_3$) δ 8.68 (s, 1H), 8.50 (d, J=2.5 Hz, 1H), 8.44 (d, J=1.7 Hz, 1H), 8.17 (d, J=8.7 Hz, 1H), 7.91 (dd, J=8.7, 2.5 Hz, 1H), 7.78 (dd, J=8.7, 1.7 Hz, 1H), 6.86 (d, J=8.7 Hz, 1H), 4.57 (t, J=5.5 Hz, 2H), 4.42 (t, J=6.5 Hz, 2H), 3.85 (t, J=5.5 Hz, 2H), 3.61 (s, 3H), 3.33 (s, 3H), 2.58-2.43 (m, 2H), 2.30 (s, 6H), 2.13-1.92 (m, 2H). $^{13}C$ NMR (50 MHz, $CDCl_3$) δ 163.8, 154.3, 145.5, 144.7, 137.6, 135.8, 132.4, 131.5, 129.7, 129.5, 126.1, 123.2, 118.3, 116.1, 111.3, 71.0, 64.7, 59.4, 56.6, 45.5, 43.7, 27.8, 27.4. ESI-MS m/z: 436.2 $[M+H]^+$ HPLC $t_{ret}$=1.30 min.

Phenylurea substituted compounds were conveniently accessible via reaction with 4-bromophenylisocyanate or Curtius rearrangement from 4-bromobenzoic acid and finally led via Suzuki coupling with (32) or (25) to the examples 10 to 26.

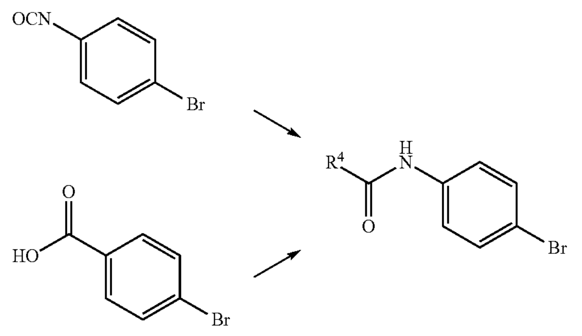

1-(4-Bromophenyl)-3-(2-(dimethylamino)ethyl)urea (33)

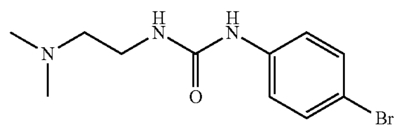 [SMILES: CN(C)CCNC(=O)Nc1ccc(Br)cc1]

To a solution of 243 mg 4-bromophenylisocyanate (1.23 mmol) in 5.0 ml dry toluene was added 119 mg N,N-dimethylethylendiamine (1.35 mmol) at ambient temperature. A suspension was formed and stirring was continued for about 2 hours. Then it was diluted with hexane and cooled in an ice bath. The solids were collected by filtration, washed with pentane and dried in vacuo to afford 348 mg (99%) of the title compound as white solid. $^1H$ NMR (400 MHz, DMSO) δ 8.78 (s, 1H), 7.40-7.33 (m, 4H), 6.10 (t, J=5.2 Hz, 1H), 3.20-3.13 (m, 2H), 2.31 (t, J=6.2 Hz, 2H), 2.15 (s, 6H). $^{13}C$ NMR (101 MHz, DMSO) δ 154.9, 140.0, 131.2, 119.3, 112.0, 58.4, 44.9, 36.9. ESI-MS m/z: 286.1 $[M+H]^+$ HPLC $t_{ret}$=3.37 min.

(1S,4S)—N-(4-Bromophenyl)-5-methyl-2,5-diazabicyclo[2.2.1]heptane-2-carboxamide (34)

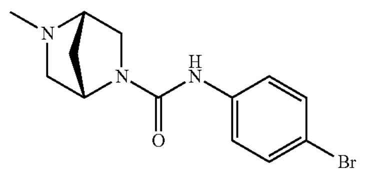 [SMILES: CN1C[C@@H]2C[C@H]1CN2C(=O)Nc1ccc(Br)cc1]

To a suspension of 301 mg (1 S,4S)-2-methyl-2,5-diazabicyclo-[2.2.1]heptane dihydrobromide (1.1 mmol) in 4 ml DMF was added 356 μl $Et_3N$ (2.5 mmol). Subsequently, were added 198 mg 4-bromophenylisocyanate (1.0 mmol) as solution in 1 ml DMF and the mixture was stirred at ambient temperature until TLC indicated complete consumption of starting material (about 2 hours). The mixture was diluted with water and basified with NaOH, followed by extractive workup with EtOAc (3×20 ml). The combined organic phases were washed with water and brine, prior to drying over $Na_2SO_4$ and evaporation. The residue was taken up in about 5 ml toluene and diluted with about the same amount pentane to obtain a white precipitate. The suspension was aged in the freezer, filtered and the solids were washed with additional pentane to afford 270 mg (87%) of the title substance as white solid. $^1H$ NMR (400 MHz, DMSO) δ 8.35 (br s, 1H), 7.49 (d, J=8.9 Hz, 2H), 7.38 (d, J=8.9 Hz, 2H), 4.48-4.40 (m, 1H), 3.48 (d, J=9.6 Hz, 1H), 3.41-3.35 (m, 1H), 3.20 (dd, J=9.6, 1.4 Hz, 1H), 2.75 (dd, J=9.6, 1.8 Hz, 1H), 2.51-2.46 (m, 1H), 2.29 (s, 3H), 1.82-1.74 (m, 1H), 1.66-1.58 (m, 1H). $^{13}C$ NMR (101 MHz, DMSO) δ 153.4, 139.9, 130.9, 121.0, 112.9, 62.2, 60.9, 57.2, 49.6, 40.8, 34.8. HPLC $t_{ret}$=2.98 min. tert-Butyl (1-((4-bromophenyl)carbamoyl)piperidin-4-yl)carbamate (35)

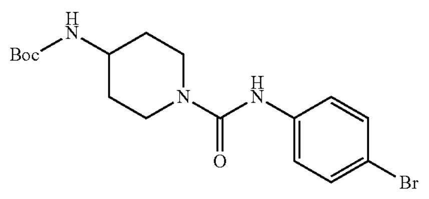 [SMILES: CC(C)(C)OC(=O)NC1CCN(C(=O)Nc2ccc(Br)cc2)CC1]

To a solution of 300 mg (1.5 mmol) and 455 mg $Et_3N$ (4.5 mmol) in 10 ml toluene was added 495 mg diphenyl phosphorylazide (1.8 mmol). The mixture was stirred at ambient temperature for 30 min and was then heated up to 90° C. heatingblock temperature for one hour. After cooling to ambient temperature, 900 mg tert-butyl piperidin-4-ylcarbamate (4.5 mmol) were added and stirring was continued at 60° C. overnight. HPLC indicated full consumption of starting material and the reaction mixture was poured on half saturated $NaHCO_3$ solution. The aqueous phase was extracted with EtOAc (4×15 ml) and subsequently the combined extracts were washed with brine, dried and evaporated. The residue was purified via flash chromatography (DCM/MeOH 2-10%). The title compound was obtained as white solid. Yield: 313 mg (53%). $^1H$ NMR (200 MHz, DMSO) δ 8.61 (s, 1H), 7.45-7.38 (m, 4H), 6.86 (d, J=7.5 Hz, 1H), 4.10-3.93 (m, 2H), 3.57-3.40 (m, 1H), 2.97-2.77 (m, 2H), 1.82-1.64 (m, 2H), 1.38 (s, 9H), 1.34-1.22 (m, 2H). ESI-MS m/z: 420.6 $[M+Na]^+$ HPLC $t_{ret}$=8.39 min.

tert-Butyl 4-(3-(4-bromophenyl)ureido)piperidine-1-carboxylate (36)

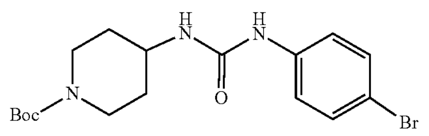 [SMILES: CC(C)(C)OC(=O)N1CCC(NC(=O)Nc2ccc(Br)cc2)CC1]

The same procedure as for the preparation of (35) was applied as described above, but using 900 mg tert-butyl 4-aminopiperidine-1-carboxylate (4.5 mmol) for quenching the isocyanate intermediate. Flash purification with gradient elution (DCM/MeOH 2-10%) afforded 272 mg (46%) of the title compound as white solid. $^1$H NMR (200 MHz, DMSO) δ 8.48 (s, 1H), 7.47-7.27 (m, 4H), 6.21 (d, J=7.6 Hz, 1H), 3.95-3.71 (m, 2H), 3.72-3.51 (m, 1H), 3.03-2.74 (m, 2H), 1.86-1.69 (m, 2H), 1.40 (s, 9H), 1.30-1.18 (m, 2H). ESI-MS m/z: 420.6 $[M+Na]^+$ HPLC $t_{ret}$=9.07 min.

1-(4-Bromophenyl)-3-(1-methylpiperidin-3-yl)urea (37)

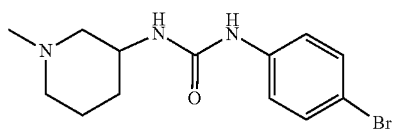 [SMILES: CN1CCCC(NC(=O)Nc2ccc(Br)cc2)C1]

To a suspension of 206 mg 3-amino-1-methylpiperidine dihydrochloride (1.1 mmol) in 4 ml DMF were added 256 mg $Et_3N$ (2.5 mmol). Subsequently, 198 mg 4-bromophenylisocyanate (1 mmol) was added as solution in DMF and the reaction was stirred at ambient temperature until TLC indicated complete consumption of starting material (about 2 hours). The mixture was diluted with water and basified with NaOH. The resulting white suspension was stirred for about 30 min under ice cooling, before the solids were isolated by filtration. The filter cake was washed with water and dried in a convection oven at 60° C. to yield 282 mg (90%) of the title substance as white solid. $^1$H NMR (400 MHz, DMSO) δ 8.64 (s, 1H), 7.39-7.28 (m, 4H), 6.26 (d, J=8.0 Hz, 1H), 3.77-3.63 (m, 1H), 2.49-2.37 (m, 1H), 2.23 (s, 2H), 2.14 (s, 3H), 2.12-2.01 (m, 1H), 1.67-1.41 (m, 3H), 1.36-1.23 (m, 1H). $^{13}$C NMR (101 MHz, DMSO) δ 154.2, 139.9, 131.3, 119.3, 112.1, 60.6, 55.1, 46.1, 45.1, 29.0, 22.2. HPLC $t_{ret}$=3.78 min.

1-(4-Bromophenyl)-3-(1-methylpiperidin-4-yl)urea (38)

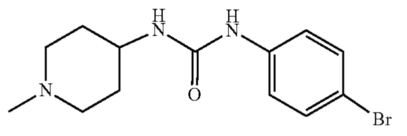 [SMILES: CN1CCC(NC(=O)Nc2ccc(Br)cc2)CC1]

The same protocol was applied as already described for the preparation of (33) using 131 mg 1-methylpiperidin-4-amine (1.15 mmol) and 198 mg 4-bromophenylisocyanate (1.0 mmol) as starting materials. Yield: 312 mg (100%) as white solid. $^1$H NMR (200 MHz, DMSO) δ 8.45 (s, 1H), 7.44-7.28 (m, 4H), 6.14 (d, J=7.6 Hz, 1H), 3.54-3.37 (m, 1H), 2.72-2.54 (m, 2H), 2.14 (s, 3H), 2.07-1.89 (m, 2H), 1.85-1.68 (m, 2H), 1.50-1.25 (m, 2H). $^{13}$C NMR (50 MHz, DMSO) δ 154.6, 140.2, 131.7, 119.8, 112.5, 54.2, 46.3, 50.0, 46.0, 32.4. ESI-MS m/z: 312.1 $[M+H]^+$ HPLC $t_{ret}$=3.80 min.

tert-Butyl 3-(3-(4-bromophenyl)ureido)pyrrolidine-1-carboxylate (39)

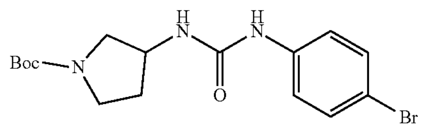 [SMILES: CC(C)(C)OC(=O)N1CCC(NC(=O)Nc2ccc(Br)cc2)C1]

The same protocol was applied as already described for the preparation of (33) using 102 mg tert-butyl 3-aminopyrrolidine-1-carboxylate (0,548 mmol) and 103 mg 4-bromophenylisocyanate (0,520 mmol) as starting materials. Yield: 160 mg (80%) as white solid. $^1$H NMR (400 MHz, DMSO) δ 8.47 (s, 1H), 7.42-7.32 (m, 4H), 6.55-6.45 (m, 1H), 4.19-4.08 (m, 1H), 3.52-3.39 (m, 1H), 3.33-3.26 (m, 2H), 3.14-3.03 (m, 1H), 2.10-1.97 (m, 1H), 1.82-1.70 (m, 1H), 1.40 (s, 9H). $^{13}$C NMR (101 MHz, DMSO) δ 154.6, 153.5, 139.7, 131.3, 119.6, 112.4, 78.3, 51.7, 51.3, 49.3, 48.5, 43.8, 43.6, 31.3, 30.4, 28.1. (complex signal splitting due to carbamate rotamers) ESI-MS m/z: 406.4 $[M+Na]^+$ HPLC $t_{ret}$=8.90 min.

1-(4-Bromophenyl)-3-(1-methylpyrrolidin-3-yl)urea (40)

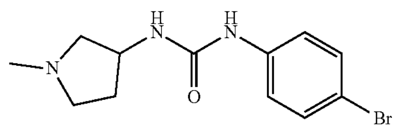 [SMILES: CN1CCC(NC(=O)Nc2ccc(Br)cc2)C1]

To a suspension of 95 mg $LiAlH_4$ (2.5 mmol) in 25 ml dry THF was added 384 mg (39) portionwise as solid at ambient temperature. After gas evolution ceased, the mixture was heated to reflux until TLC indicated complete conversion (about 3 hours). The mixture was cooled to ambient temperature and 100 μl water were added dropwise. After gas evolution ceased, 100 μl of a 15 wt % aqueous NaOH solution were added and stirring was continued for ten minutes. Then, 300 μl water were added dropwise followed by addition of $Na_2SO_4$ and stirring was again continued for about 30 min at ambient temperature. The white suspension was then filtered over celite and the filter was rinsed with EtOAc. The filtrate was washed with water and brine, dried over $Na_2SO_4$ and concentrated under reduced pressure. The residue was triturated with pentane and the precipitate isolated by filtration to obtain 253 mg (85%) of the title substance as white solid. $^1$H NMR (400 MHz, DMSO) δ 8.50 (br s, 1H), 7.41-7.28 (m, 4H), 6.39 (d, J=7.6 Hz, 1H), 4.17-4.05 (m, 1H), 2.65 (td, J=8.4, 5.0 Hz, 1H), 2.54-2.46 (m, 1H), 2.36 (dd, J=9.3, 3.5 Hz, 1H), 2.24 (s, 3H), 2.29-2.20 (m, 1H), 2.19-2.07 (m, 1H), 1.55-1.44 (m, 1H). $^{13}$C NMR (101 MHz, DMSO) δ 154.4, 139.8, 131.2, 119.4, 112.2, 62.6, 54.3, 49.0, 41.6, 32.6. HPLC $t_{ret}$=3.56 min.

tert-Butyl 3-(3-(4-bromophenyl)ureido)azetidine-1-carboxylate (41)

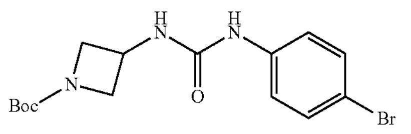 [SMILES: CC(C)(C)OC(=O)N1CC(NC(=O)Nc2ccc(Br)cc2)C1]

The same protocol was applied as already described for the preparation of (33) using 287 mg tert-butyl 3-aminoazetidine-1-carboxylate (1.67 mmol) and 300 mg 4-bromophenylisocyanate (1.52 mmol) as starting materials. Yield: 541 mg (96%) as white solid. $^1$H NMR (400 MHz, DMSO) δ 8.67 (s, 1H), 7.41-7.34 (m, 4H), 6.84 (d, J=7.2 Hz, 1H), 4.43-4.29 (m, 1H), 4.05 (t, J=8.1 Hz, 2H), 3.74-3.64 (m, 2H), 1.38 (s, 9H). $^{13}$C NMR (101 MHz, DMSO) δ 155.5, 154.4, 139.6, 131.3, 119.9, 112.7, 78.6, 56.1, 28.1. ESI-MS m/z: 367.7 $[M-]^-$ HPLC $t_{ret}$=8.64 min.

1-(4-Bromophenyl)-3-(1-methylazetidin-3-yl)urea (42)

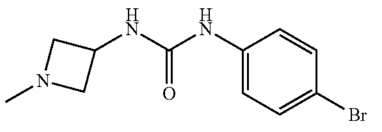 [SMILES: CN1CC(NC(=O)Nc2ccc(Br)cc2)C1]

The same method was used as for the synthesis of (40) using 520 mg (41) as the starting material. Yield: 401 mg (100%) as white solid. $^1$H NMR (400 MHz, DMSO) δ 8.52 (s, 1H), 7.42-7.29 (m, 4H), 6.65 (d, J=7.8 Hz, 1H), 4.21-4.10 (m, 1H), 3.53-3.46 (m, 2H), 2.77-2.73 (m, 2H), 2.21 (s, 3H). $^{13}$C NMR (101 MHz, DMSO) δ 154.2, 139.7, 131.3, 119.7, 112.5, 63.5, 45.7, 40.1. ESI-MS m/z: 284.1 $[M+H]^+$ HPLC $t_{ret}$=3.38 min.

N-(4-Bromophenyl)-4-methylpiperazine-1-carboxamide (43)

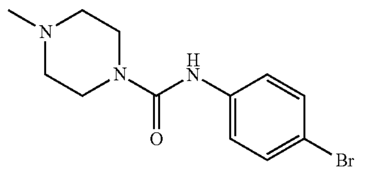 [SMILES: CN1CCN(C(=O)Nc2ccc(Br)cc2)CC1]

The same protocol was applied as already described for the preparation of (33) using 101 mg 1-methylpiperazine (1.01 mmol) and 200 mg 4-bromophenylisocyanate (1.01 mmol) as starting materials. Yield: 249 mg (83%) as white solid. $^1$H NMR (400 MHz, DMSO) δ 8.62 (s, 1H), 7.44 (d, J=8.8 Hz, 2H), 7.39 (d, J=8.8 Hz, 2H), 3.47-3.38 (m, 4H), 2.35-2.26 (m, 4H), 2.19 (s, 3H). $^{13}$C NMR (101 MHz, DMSO) δ 154.6, 140.0, 131.0, 121.3, 113.1, 54.4, 45.6, 43.6. ESI-MS m/z: 320.2 $[M+Na]^+$ HPLC $t_{ret}$=3.06 min.

N-(4-Bromophenyl)-4-ethylpiperazine-1-carboxamide (44)

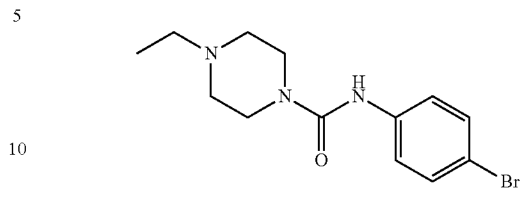

The same protocol was applied as already described for the preparation of (33) using 97 mg 1-ethylpiperazine (0.85 mmol) and 140 mg 4-bromophenylisocyanate (0.71 mmol) as starting materials. Yield: 220 mg (99%) as white solid. $^1$H NMR (400 MHz, DMSO) δ 8.61 (br s, 1H), 7.45 (d, J=8.4 Hz, 2H), 7.38 (d, J=8.4 Hz, 2H), 3.48-3.38 (m, 4H), 2.38-2.27 (m, 6H), 1.01 (t, J=7.1 Hz, 3H). $^{13}$C NMR (101 MHz, DMSO) δ 154.7, 140.0, 131.0, 121.3, 113.1, 52.2, 51.6, 43.7, 11.9. ESI-MS m/z: 366.4 $[M+Na+MeOH]^+$ HPLC $t_{ret}$=3.17 min.

N-(4-Bromophenyl)-4-isopropylpiperazine-1-carboxamide (45)

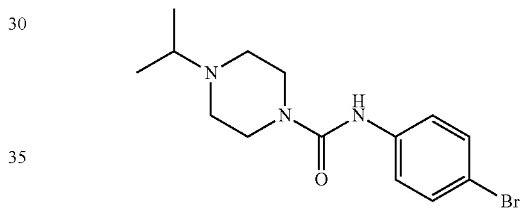

The same protocol was applied as already described for the preparation of (33) using 93 mg 1-ethylpiperazine (0.73 mmol) and 120 mg 4-bromophenylisocyanate (0.61 mmol) as starting materials. Yield: 181 mg (92%) as white solid. $^1$H NMR (400 MHz, DMSO) δ 8.60 (br s, 1H), 7.45 (d, J=8.6 Hz, 2H), 7.38 (d, J=8.6 Hz, 2H), 3.46-3.38 (m, 4H), 2.66 (hept, J=6.5 Hz, 1H), 2.47-2.36 (m, 4H), 0.97 (d, J=6.5 Hz, 6H). $^{13}$C NMR (101 MHz, DMSO) δ 154.6, 140.1, 131.0, 121.3, 113.1, 53.7, 48.0, 44.1, 18.1. ESI-MS m/z: 380.2 $[M+Na+MeOH]^+$ HPLC $t_{ret}$=3.24 min.

N-(4-Bromophenyl)-4-(dimethylamino)piperidine-1-carboxamide (46)

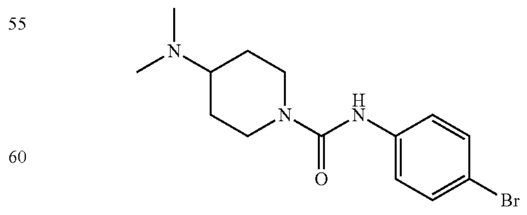

The same protocol was applied as already described for the preparation of (33) using 101 mg N,N-dimethylpiperidin-4-amine (1.05 mmol) and 149 mg 4-bromophenylisocyanate (0.75 mmol) as starting materials. Yield: 214 mg (88%) as white solid. $^1$H NMR (400 MHz, DMSO) δ 8.60 (s, 1H), 7.44 (d, J=8.8 Hz, 2H), 7.38 (d, J=8.8 Hz, 2H), 4.14-4.05 (m, 2H), 2.84-2.72 (m, 2H), 2.31-2.21 (m, 1H), 2.17 (s, 6H), 1.80-1.70 (m, 2H), 1.34-1.20 (m, 2H). $^{13}$C NMR (101 MHz, DMSO) δ 154.5, 140.2, 131.0, 121.3, 113.0, 61.3, 43.0, 41.4, 28.0. ESI-MS m/z: 326.3 [M+H]$^+$ HPLC $t_{ret}$=3.22 min.

N-(4-Bromophenyl)-3-(dimethylamino)pyrrolidine-1-carboxamide (47)

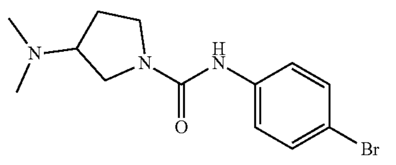 [SMILES: CN(C)C1CCN(C(=O)Nc2ccc(Br)cc2)C1]

The same method was applied as described above for the preparation of (37) using 147 mg N,N-dimethylpyrrolidin-3-amine dihydrochloride (0,789 mmol), 149 mg 4-bromophenylisocyanate (0,750 mmol) and 190 mg TEA (1.88 mmol) as starting materials. The reaction was quenched with 4.5 ml water, basified with NaOH to pH 9 and extracted with EA (3×20 ml). After drying over $Na_2SO_4$, the combined organic phases were evaporated under reduced pressure. Yield: 160 mg (68%) as white solid. $^1$H NMR (400 MHz, DMSO) δ 8.24 (s, 1H), 7.50 (d, J=8.8 Hz, 2H), 7.38 (d, J=8.8 Hz, 2H), 3.67-3.60 (m, 1H), 3.58-3.50 (m, 1H), 3.34-3.26 (m, 1H), 3.09 (t, J=9.1 Hz, 1H), 2.74-2.63 (m, 1H), 2.18 (s, 6H), 2.09-2.00 (m, 1H), 1.75-1.64 (m, 1H). $^{13}$C NMR (101 MHz, DMSO) δ 153.5, 140.0, 131.0, 121.2, 113.0, 64.7, 49.9, 44.8, 43.8, 29.4. ESI-MS m/z: 310.1 [M−]$^-$ HPLC $t_{ret}$=3.02 min.

N-(4-Bromophenyl)-3-(dimethylamino)azetidine-1-carboxamide (48)

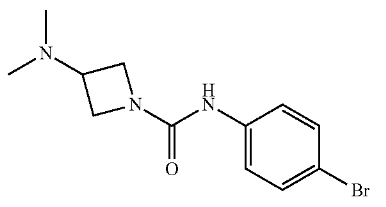 [SMILES: CN(C)C1CN(C(=O)Nc2ccc(Br)cc2)C1]

The same method was applied as described above for the preparation of (37) using 140 mg N,N-dimethylazetidin-3-amine dihydrochloride (0.788 mmol) and 149 mg 4-bromophenylisocyanate (0,750 mmol) as starting materials. Yield: 176 mg (79%) as white solid. $^1$H NMR (400 MHz, DMSO) δ 8.54 (s, 1H), 7.48 (d, J=8.5 Hz, 2H), 7.39 (d, J=8.1 Hz, 2H), 3.99-3.91 (m, 2H), 3.77-3.68 (m, 2H), 3.05-2.96 (m, 1H), 2.07 (s, 6H). $^{13}$C NMR (101 MHz, DMSO) δ 156.4, 139.7, 131.1, 120.5, 113.0, 54.5, 53.4, 41.4. ESI-MS m/z: 398.2 [M+H]$^+$ HPLC $t_{ret}$=3.12 min.

Example 10

1-(2-(Dimethylamino)ethyl)-3-(4-(3-methyl-2-oxo-1-(tetrahydro-2H-pyran-4-yl)-2,3-dihydro-1H-imidazo[4,5-c]quinolin-8-yl)phenyl)urea

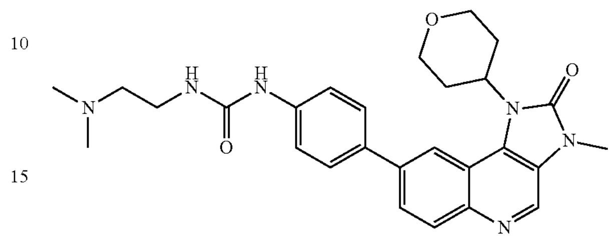

In a schlenk tube were combined 43 mg (33) (0.15 mmol) and 74 mg (25) (0.18 mmol) under argon atmosphere. Subsequently were added 3 ml dioxane and 0.9 ml of an aqueous 0.5M $K_3PO_4$ solution (0.45 mmol) and the mixture was degassed carefully via three vacuum/argon cycles. Then, 1.7 mg $tBu_3P$ Pd G3 (2 mol %) were added and the degassing procedure was repeated. The flask was sealed and heated to 70° C. oil-bath temperature and stirring was continued overnight. TLC indicated complete conversion at that point and the reaction was quenched by dilution with EtOAc and brine. The phases were separated and the aqueous phase was further extracted with EtOAc (3×15 ml). The combined extracts were washed with brine, dried and evaporated. The residue was purified via flash chromatography (DCM/MeOH+2N $NH_3$ 1-7%) to obtain 48 mg (66%) of the title substance as white solid. $^1$H NMR (200 MHz, DMSO) δ 9.01-8.71 (m, 2H), 8.39 (s, 1H), 8.19-8.02 (m, 1H), 7.98-7.85 (m, 1H), 7.73 (d, J=7.8 Hz, 2H), 7.56 (d, J=8.5 Hz, 2H), 6.30-6.09 (m, 1H), 5.22-5.00 (m, 1H), 4.18-3.98 (m, 2H), 3.66-3.55 (m, 2H), 3.49 (s, 3H), 3.27-3.15 (m, 2H), 2.86-2.59 (m, 2H), 2.44-2.33 (m, 2H), 2.21 (s, 6H), 2.02-1.82 (m, 2H). ESI-MS m/z: 489.4 [M+H]$^+$ HPLC $t_{ret}$=1.43 min.

Example 11

1-(2-(Dimethylamino)ethyl)-3-(4-(1-(2-methoxyethyl)-3-methyl-2-oxo-2,3-dihydro-1H-imidazo[4,5-c]quinolin-8-yl)phenyl)urea

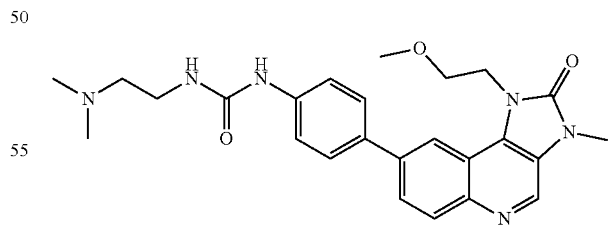

The preparation of this example was carried out following the same protocol as for example 10, but with 57 mg (33) (0.2 mmol) and 92 mg (32) (0.24 mmol) as the starting materials. Reaction time: 3 hours at 70° C. oil bath temperature. Yield: 66 mg (71%) as white solid. $^1$H NMR (400 MHz, DMSO) δ 8.99 (s, 1H), 8.83 (s, 1H), 8.43-8.36 (m, 1H), 8.05 (d, J=8.9 Hz, 1H), 7.90 (dd, J=8.9, 1.8 Hz, 1H), 7.72 (d, J=8.6 Hz, 2H), 7.56 (d, J=8.5 Hz, 2H), 6.52-6.16 (m, 1H), 4.54 (t, J=5.5 Hz, 2H), 3.76 (t, J=5.6 Hz, 2H), 3.52 (s, 3H), 3.33-3.19 (m, 5H), 2.54 (t, J=5.1 Hz, 2H), 2.33 (s, 6H). ESI-MS m/z: 463.4 $[M+H]^+$ HPLC $t_{ret}$=1.42 min.

Example 12

(1S,4S)—N-(4-(1-(2-Methoxyethyl)-3-methyl-2-oxo-2,3-dihydro-1H-imidazo[4,5-c]quinolin-8-yl)phenyl)-5-methyl-2,5-diazabicyclo[2.2.1]heptane-2-carboxamide

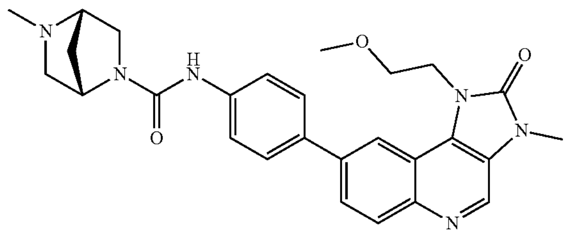

To a suspension of 42 mg (32) (0.11 mmol), 38 mg (34) (0.12 mmol) and 1 mg $tBu_3P$ Pd G3 (1.5 mol %) in 2.6 ml degassed dioxane were added 0.66 ml of a 0.5 M aqueous $K_3PO_4$ solution (0.33 mmol). The reaction vial was sealed and heated to 50° C. heatingblock temperature overnight and TLC indicated complete conversion at that point. Activated carbon was added to the mixture and stirring was continued for one hour. The reaction was diluted with EA and filtered. The filtrate was washed with brine, the organic phase was dried over $Na_2SO_4$ and evaporated. The residue was purified via flash chromatography (DCM/MeOH+2N $NH_3$ 2-10%) to yield 16 mg (30%) of the title substance as off-white solid. $^1$H NMR (400 MHz, DMSO) δ 8.85 (s, 1H), 8.46-8.35 (m, 2H), 8.07 (d, J=8.9 Hz, 1H), 7.93 (dd, J=8.9, 1.6 Hz, 1H), 7.74 (d, J=8.8 Hz, 2H), 7.68 (d, J=8.8 Hz, 2H), 4.56 (t, J=5.6 Hz, 2H), 4.52-4.45 (m, 1H), 3.78 (t, J=5.6 Hz, 2H), 3.53 (s, 3H), 3.53-3.49 (m, 1H), 3.44-3.39 (m, 1H), 3.29-3.25 (m, 1H), 3.24 (s, 3H), 2.79 (dd, J=9.4, 1.5 Hz, 1H), 2.56-2.51 (m, 1H), 2.32 (s, 3H), 1.84-1.77 (m, 1H), 1.70-1.60 (m, 1H). $^{13}$C NMR (101 MHz, DMSO) δ 153.6, 153.5, 143.5, 140.5, 137.4, 132.8, 132.5, 130.6, 128.5, 126.9, 125.4, 122.8, 119.5, 117.3, 115.3, 70.0, 62.2, 61.0, 58.3, 57.2, 49.6, 42.5, 40.8, 34.8, 27.4. ESI-MS m/z: 487.4 $[M+H]^+$ HPLC $t_{ret}$=1.37 min.

Example 13 tert-Butyl (1-((4-(1-(2-methoxyethyl)-3-methyl-2-oxo-2,3-dihydro-1H-imidazo[4,5-c]quinolin-8-yl)phenyl)carbamoyl)piperidin-4-yl)carbamate

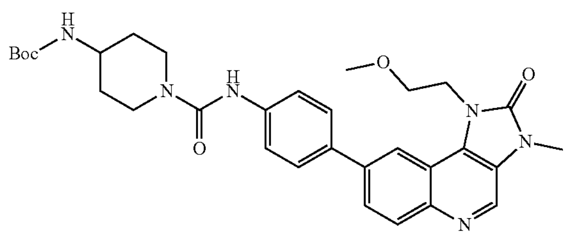 [SMILES: COCCn1c(=O)n(C)c2cnc3ccc(-c4ccc(NC(=O)N5CCC(NC(=O)OC(C)(C)C)CC5)cc4)cc3c21]

The preparation of this example was carried out following the same protocol as for example 10, but with 131 mg (35) (0.33 mmol) and 152 mg (32) (0.40 mmol) as the starting materials. Flash chromatography was carried out with DCM/MeOH (0-8%). Yield: 97 mg (52%) as white solid. $^1$H NMR (200 MHz, DMSO) δ 8.85 (s, 1H), 8.72-8.63 (m, 1H), 8.47-8.39 (m, 1H), 8.07 (d, J=9.0 Hz, 1H), 7.98-7.88 (m, 1H), 7.74 (d, J=8.8 Hz, 2H), 7.63 (d, J=8.7 Hz, 2H), 6.88 (d, J=8.3 Hz, 1H), 4.57 (t, J=5.4 Hz, 2H), 4.16-3.97 (m, 2H), 3.78 (t, J=5.5 Hz, 2H), 3.58-3.43 (m, 4H), 3.24 (s, 3H), 3.01-2.80 (m, 2H), 1.86-1.67 (m, 2H), 1.39 (s, 9H), 1.33-1.20 (m, 2H). ESI-MS m/z: 575.7 $[M+H]^+$ HPLC $t_{ret}$=5.94 min.

Example 14

4-Amino-N-(4-(1-(2-methoxyethyl)-3-methyl-2-oxo-2,3-dihydro-1H-imidazo[4,5-c]quinolin-8-yl)phenyl)piperidine-1-carboxamide

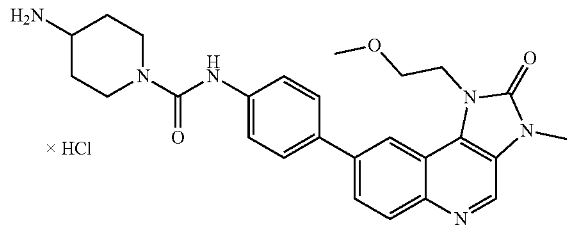 [SMILES: COCCn1c(=O)n(C)c2cnc3ccc(-c4ccc(NC(=O)N5CCC(N)CC5)cc4)cc3c21]

A solution of 77 mg of the compound of example 13 (0.13 mmol) in 3 ml ethanolic HCl (2.5N) was stirred at ambient temperature overnight. The solvents were stripped off under reduced pressure and the residue triturated with THF. The solids were isolated by filtration and dried in vacuo to obtain the title compound as the hydrochloride salt. Yield: 33 mg (50%) as a white solid. $^1$H NMR (400 MHz, DMSO) δ 9.23 (s, 1H), 8.93 (s, 1H), 8.65 (s, 1H), 8.38-8.31 (m, 1H), 8.26 (br s, 3H), 8.31-8.17 (m, 1H), 7.78 (d, J=8.3 Hz, 2H), 7.69 (d, J=8.3 Hz, 2H), 4.67 (t, J=5.2 Hz, 2H), 4.34-4.14 (m, 2H), 3.86-3.79 (m, 2H), 3.59 (s, 3H), 3.43-3.41 (m, 1H), 3.23 (s, 3H), 2.98-2.84 (m, 2H), 2.02-1.90 (m, 2H), 1.61-1.41 (m, 2H). ESI-MS m/z: 475.6 $[M+H]^+$ HPLC $t_{ret}$=1.41 min.

Example 15 tert-Butyl 4-(3-(4-(1-(2-methoxyethyl)-3-methyl-2-oxo-2,3-dihydro-1H-imidazo[4,5-c]quinolin-8-yl)phenyl)ureido)piperidine-1-carboxylate

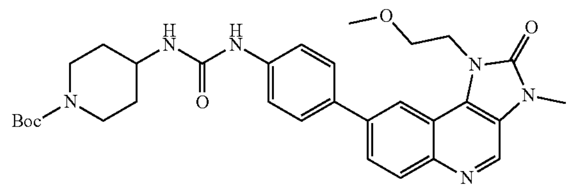 [SMILES: COCCn1c(=O)n(C)c2cnc3ccc(-c4ccc(NC(=O)NC5CCN(C(=O)OC(C)(C)C)CC5)cc4)cc3c21]

The preparation of this example was carried out following the same protocol as for example 10, but with 177 mg (36) (0.44 mmol) and 207 mg (32) (0.54 mmol) as the starting materials. Flash chromatography was carried out with DCM/MeOH (0-10%). Yield: 115 mg (45%) as white solid. $^1$H NMR (200 MHz, DMSO) δ 8.84 (s, 1H), 8.52 (s, 1H), 8.45-8.37 (m, 1H), 8.07 (d, J=8.8 Hz, 1H), 7.98-7.86 (m, 1H), 7.73 (d, J=8.5 Hz, 2H), 7.54 (d, J=8.7 Hz, 2H), 6.25 (d, J=7.5 Hz, 1H), 4.56 (t, J=5.0 Hz, 2H), 3.91-3.60 (m, 5H), 3.53 (s, 3H), 3.24 (s, 3H), 3.03-2.83 (m, 2H), 1.92-1.74 (m, 2H), 1.41 (s, 9H), 1.34-1.21 (m, 2H). ESI-MS m/z: 597.9 $[M+Na]^+$ HPLC $t_{ret}$=6.80 min.

Example 16

1-(4-(1-(2-Methoxyethyl)-3-methyl-2-oxo-2,3-dihydro-1H-imidazo[4,5-c]quinolin-8-yl)phenyl)-3-(piperidin-4-yl)urea

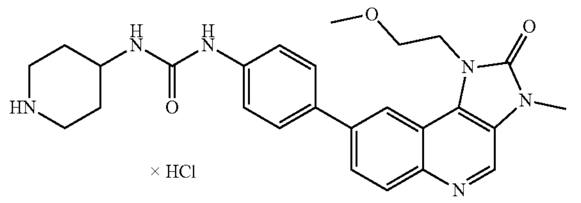 [SMILES: COCCn1c(=O)n(C)c2cnc3ccc(-c4ccc(NC(=O)NC5CCNCC5)cc4)cc3c21]

A solution of 43 mg of the compound of example 15 (0.08 mmol) in 3 ml ethanolic HCl (2.5N) was stirred at ambient temperature overnight. The solvents were stripped off under reduced pressure and the residue triturated with THF. The solids were isolated by filtration and dried in vacuo to obtain the title compound as the hydrochloride salt. Yield: 30 mg (73%) as a white solid. $^1$H NMR (400 MHz, DMSO) δ 9.29 (s, 1H), 9.24 (s, 1H), 8.96 (br s, 1H), 8.87 (br s, 1H), 8.67 (s, 1H), 8.39 (d, J=7.9 Hz, 1H), 8.28 (d, J=7.9 Hz, 1H), 7.77 (d, J=7.2 Hz, 2H), 7.58 (d, J=7.2 Hz, 2H), 7.11 (d, J=6.8 Hz, 1H), 4.84-4.54 (m, 2H), 3.87-3.77 (m, 3H), 3.59 (s, 3H), 3.23 (s, 3H), 3.29-3.22 (m, 2H), 3.07-2.93 (m, 2H), 2.10-1.91 (m, 2H), 1.76-1.55 (m, 2H). ESI-MS m/z: 473.7 $[M-]^-$ HPLC $t_{ret}$=1.55 min.

Example 17

1-(4-(1-(2-Methoxyethyl)-3-methyl-2-oxo-2,3-dihydro-1H-imidazo[4,5-c]quinolin-8-yl)phenyl)-3-(1-methylpiperidin-3-yl)urea

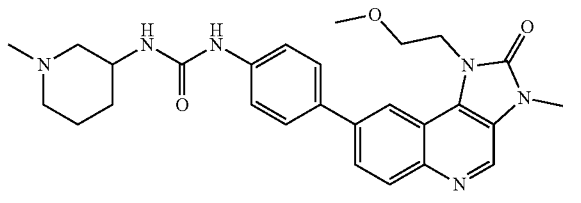

The preparation of this final compound was performed following the same procedure as described above for the compound of example 15 using 42 mg (32) (0.11 mmol) and 38 mg (37) (0.12 mmol) as the starting materials. Flash chromatography with DCM/MeOH+2N $NH_3$ (2-10%) yielded 27 mg (50%) of the title compound as white solid. $^1$H NMR (400 MHz, DMSO) δ 8.83 (s, 1H), 8.69 (s, 1H), 8.39 (d, J=1.5 Hz, 1H), 8.05 (d, J=8.9 Hz, 1H), 7.90 (dd, J=8.9, 1.5 Hz, 1H), 7.71 (d, J=8.6 Hz, 2H), 7.54 (d, J=8.6 Hz, 2H), 6.31 (d, J=8.0 Hz, 1H), 4.54 (t, J=5.5 Hz, 2H), 3.77 (t, J=5.5 Hz, 2H), 3.81-3.69 (m, 1H), 3.52 (s, 3H), 3.23 (s, 3H), 2.54-2.44 (m, 1H), 2.35-2.20 (m, 2H), 2.17 (s, 3H), 2.19-2.05 (m, 1H), 1.71-1.43 (m, 3H), 1.41-1.26 (m, 1H). $^{13}$C NMR (101 MHz, DMSO) δ 154.3, 153.4, 143.5, 140.5, 137.3, 132.7, 132.0, 130.6, 128.4, 127.2, 125.4, 122.8, 117.8, 117.2, 115.3, 70.0, 60.6, 58.3, 55.1, 46.1, 45.1, 42.5, 29.1, 27.4, 22.2. ESI-MS m/z: 511.3 $[M+Na]^+$ HPLC $t_{ret}$=1.71 min.

Example 18

1-(4-(1-(2-Methoxyethyl)-3-methyl-2-oxo-2,3-dihydro-1H-imidazo[4,5-c]quinolin-8-yl)phenyl)-3-(1-methylpiperidin-4-yl)urea

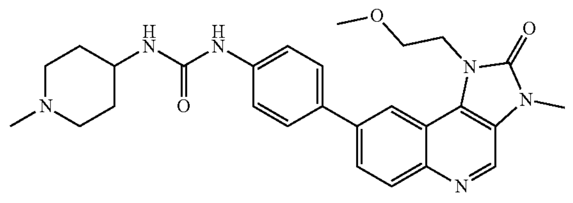

The preparation of this final compound was performed following the same procedure as described above for the compound of example 15 using 42 mg (32) (0.11 mmol) and 38 mg (38) (0.12 mmol) as the starting materials. Flash chromatography with DCM/MeOH+2N $NH_3$ (2-10%) yielded 26 mg (48%) of the title compound as white solid. $^1$H NMR (400 MHz, DMSO+MeOD+TFA) δ 8.82 (s, 1H), 8.40 (d, J=1.6 Hz, 1H), 8.05 (d, J=8.9 Hz, 1H), 7.90 (dd, J=8.9, 1.6 Hz, 1H), 7.71 (d, J=8.6 Hz, 2H), 7.56 (d, J=8.6 Hz, 2H), 4.54 (t, J=5.5 Hz, 2H), 3.77 (t, J=5.5 Hz, 2H), 3.73-3.64 (m, 1H), 3.52 (s, 3H), 3.23 (s, 4H), 3.23-3.15 (m, 2H), 2.93-2.79 (m, 2H), 2.63 (s, 3H), 2.06-1.90 (m, 2H), 1.69-1.51 (m, 2H). ESI-MS m/z: 511.4 $[M+Na]^+$ HPLC $t_{ret}$=1.65 min.

Example 19

1-(4-(1-(2-Methoxyethyl)-3-methyl-2-oxo-2,3-dihydro-1H-imidazo[4,5-c]quinolin-8-yl)phenyl)-3-(1-methylpyrrolidin-3-yl)urea

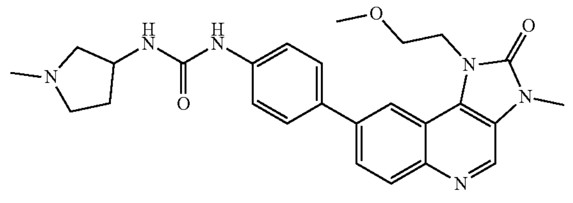

The preparation of this final compound was performed following the same procedure as described above for the compound of example 15 using 42 mg (32) (0.11 mmol) and 36 mg (40) (0.12 mmol) as the starting materials. Flash chromatography with DCM/MeOH+2N $NH_3$ (2-10%) yielded 26 mg (50%) of the title compound as white solid. $^1$H NMR (400 MHz, DMSO+MeOD) δ 8.82 (s, 1H), 8.40 (d, J=1.7 Hz, 1H), 8.05 (d, J=8.9 Hz, 1H), 7.90 (dd, J=8.9, 1.7 Hz, 1H), 7.71 (d, J=8.7 Hz, 2H), 7.52 (d, J=8.7 Hz, 2H), 4.54 (t, J=5.5 Hz, 2H), 4.19-4.11 (m, 1H), 3.77 (t, J=5.5 Hz, 2H), 3.52 (s, 3H), 3.23 (s, 3H), 2.72-2.61 (m, 1H), 2.57-2.51 (m, 1H), 2.39 (dd, J=9.4, 3.6 Hz, 1H), 2.26 (s, 3H), 2.29-2.22 (m, 1H), 2.22-2.12 (m, 1H), 1.59-1.46 (m, 1H). ESI-MS m/z: 497.3 $[M+Na]^+$ HPLC $t_{ret}$=1.60 min.

Example 20

N-(4-(1-(2-methoxyethyl)-3-methyl-2-oxo-2,3-dihydro-1H-imidazo[4,5-c]quinolin-8-yl)phenyl)-4-methylpiperazine-1-carboxamide

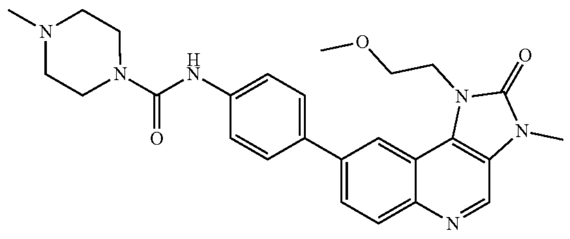

The preparation of this final compound was performed following the same procedure as described above for the compound of example 15 using 108 mg (32)(0.28 mmol) and 80 mg (43)(0.27 mmol) as the starting materials. Flash chromatography with DCM/MeOH+2N $NH_3$ (2-10%) yielded 80 mg (63%) of the title compound as white solid. $^1H$ NMR (400 MHz, $CDCl_3$+MeOD) δ 8.62 (s, 1H), 8.43 (d, J=1.8 Hz, 1H), 8.11 (d, J=8.9 Hz, 1H), 7.83 (dd, J=8.9, 1.9 Hz, 1H), 7.66-7.58 (m, 2H), 7.49 (d, J=8.6 Hz, 2H), 4.55 (t, J=5.6 Hz, 2H), 3.83 (t, J=5.6 Hz, 2H), 3.58 (s, 3H), 3.56 (d, J=5.2 Hz, 4H), 3.32 (s, 3H), 2.53-2.46 (m, 4H), 2.34 (s, 3H). $^{13}C$ NMR (101 MHz, $CDCl_3$+MeOD) δ 155.3, 154.3, 144.2, 139.2, 138.7, 134.9, 131.9, 130.6, 129.9, 127.7, 126.7, 123.1, 120.6, 120.5, 118.1, 116.0, 70.7, 59.2, 54.7, 45.9, 43.8, 43.5, 27.8. ESI-MS m/z: 475.3 $[M+H]^+$ HPLC $t_{ret}$=1.41 min.

Example 21

1-(4-(1-(2-Methoxyethyl)-3-methyl-2-oxo-2,3-dihydro-1H-imidazo[4,5-c]quinolin-8-yl)phenyl)-3-(1-methylazetidin-3-yl)urea

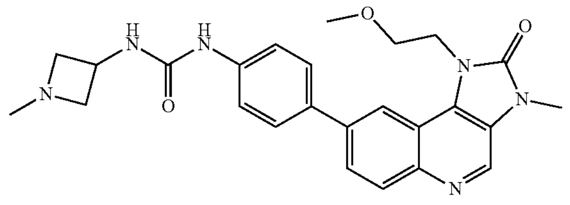

The preparation of this final compound was performed following the same procedure as described above for the compound of example 15 using 113 mg (32) (0.30 mmol) and 80 mg (42) (0.28 mmol) as the starting materials. Flash chromatography with DCM/MeOH+2N $NH_3$ (2-10%) yielded 79 mg (61%) of the title compound as white solid. $^1H$ NMR (400 MHz, $CDCl_3$+MeOD) δ 8.60 (s, 1H), 8.40 (d, J=1.6 Hz, 1H), 8.08 (d, J=8.9 Hz, 1H), 7.82 (dd, J=8.9, 1.8 Hz, 1H), 7.59 (d, J=8.7 Hz, 2H), 7.49 (d, J=8.6 Hz, 2H), 4.54 (t, J=5.6 Hz, 2H), 4.43 (ddd, J=11.4, 7.3, 4.3 Hz, 1H), 3.82 (t, J=5.6 Hz, 2H), 3.62 (t, J=8.2 Hz, 3H), 3.57 (s, 3H), 3.35 (dd, J=9.2, 4.2 Hz, 2H), 3.30 (s, 3H), 2.43 (s, 3H). $^{13}C$ NMR (101 MHz, $CDCl_3$+MeOD) δ 155.4, 154.4, 144.2, 139.5, 138.9, 134.3, 131.8, 130.5, 129.9, 127.8, 126.7, 123.1, 119.4, 117.9, 116.0, 70.7, 63.4, 59.2, 44.7, 43.6, 41.2, 27.7. ESI-MS m/z: 461.3 $[M+H]^+$ HPLC $t_{ret}$=1.61 min.

Example 22

4-Ethyl-N-(4-(1-(2-methoxyethyl)-3-methyl-2-oxo-2,3-dihydro-1H-imidazo[4,5-c]quinolin-8-yl)phenyl)piperazine-1-carboxamide

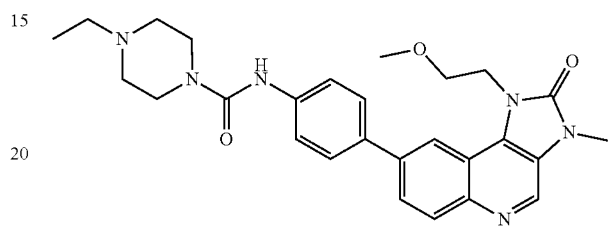

The preparation of this final compound was performed following the same procedure as described above for the compound of example 15 using 42 mg (32) (0.11 mmol) and 34 mg (44) (0.11 mmol) as the starting materials. Flash chromatography with DCM/MeOH+2N $NH_3$ (1-7%) yielded 32 mg (60%) of the title compound as white solid. $^1H$ NMR (400 MHz, DMSO) δ 8.84 (s, 1H), 8.66 (s, 1H), 8.42 (s, 1H), 8.06 (d, J=8.8 Hz, 1H), 7.92 (d, J=8.8 Hz, 1H), 7.73 (d, J=8.0 Hz, 2H), 7.64 (d, J=8.0 Hz, 2H), 4.55 (t, J=5.1 Hz, 2H), 3.77 (t, J=5.1 Hz, 2H), 3.52 (s, 3H), 3.50-3.39 (m, 4H), 3.24 (s, 3H), 2.45-2.27 (m, 6H), 1.03 (t, J=7.0 Hz, 3H). $^{13}C$ NMR (101 MHz, DMSO) δ 154.9, 153.5, 143.5, 140.6, 137.4, 132.9, 132.7, 130.6, 128.5, 126.9, 125.5, 122.9, 119.8, 117.4, 115.3, 70.1, 58.4, 52.3, 51.6, 43.8, 42.5, 27.5, 11.9. ESI-MS m/z: 489.5 $[M+H]^+$ HPLC $t_{ret}$=1.95 min.

Example 23

4-Isopropyl-N-(4-(1-(2-methoxyethyl)-3-methyl-2-oxo-2,3-dihydro-1H-imidazo[4,5-c]quinolin-8-yl)phenyl)piperazine-1-carboxamide

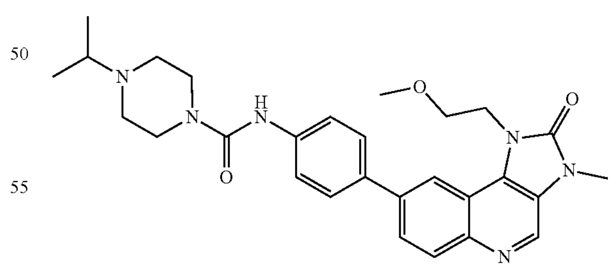

The preparation of this final compound was performed following the same procedure as described above for the compound of example 15 using 42 mg (32) (0.11 mmol) and 36 mg (45) (0.11 mmol) as the starting materials. Flash chromatography with DCM/MeOH+2N $NH_3$ (1-7%) yielded 36 mg (65%) of the title compound as white solid. $^1H$ NMR (400 MHz, DMSO) δ 8.84 (s, 1H), 8.65 (s, 1H), 8.42 (s, 1H), 8.06 (d, J=8.8 Hz, 1H), 7.95-7.89 (m, 1H), 7.73 (d, J=8.2 Hz, 2H), 7.64 (d, J=8.2 Hz, 2H), 4.55 (t, J=5.2 Hz, 2H), 3.77 (t, J=5.2 Hz, 2H), 3.53 (s, 3H), 3.49-3.43 (m, 4H), 3.24 (s, 3H), 2.73-2.64 (m, 1H), 2.49-2.40 (m, 4H), 0.99 (d, J=6.4 Hz, 6H). ESI-MS m/z: 503.4 $[M+H]^+$ HPLC $t_{ret}$=2.16 min.

Example 24

4-(Dimethylamino)-N-(4-(1-(2-methoxyethyl)-3-methyl-2-oxo-2,3-dihydro-1H-imidazo[4,5-c]quinolin-8-yl)phenyl)piperidine-1-carboxamide

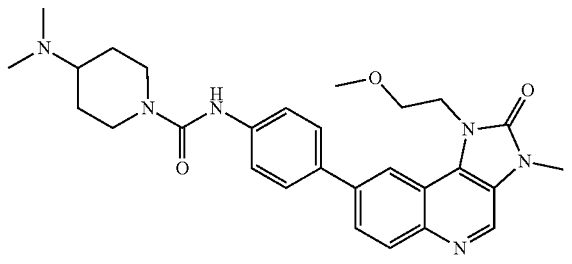

The preparation of this example was carried out following the same protocol as for example 10, but with 49 mg (46) (0.150 mmol), 54 mg (32) (0.165 mmol) and 136 mg potassiumphosphate trihydrate (0.600 mmol) in 2.5 ml Dioxan and 0.5 ml water as the starting materials. The Reaction was run at 60° C. overnight. Flash chromatography was carried out with DCM/MeOH+2N $NH_3$ (5-10%). Yield: 75 mg (99%) as white solid. $^1$H NMR (400 MHz, DMSO) δ 8.84 (s, 1H), 8.66 (s, 1H), 8.42 (s, 1H), 8.06 (d, J=8.8 Hz, 1H), 7.92 (d, J=8.8 Hz, 1H), 7.72 (d, J=8.4 Hz, 2H), 7.64 (d, J=8.3 Hz, 2H), 4.61-4.48 (m, 2H), 4.22-4.10 (m, 2H), 3.82-3.73 (m, 2H), 3.52 (s, 3H), 3.24 (s, 3H), 2.88-2.75 (m, 2H), 2.37-2.27 (m, 1H), 2.20 (s, 6H), 1.85-1.72 (m, 2H), 1.39-1.25 (m, 2H). $^{13}$C NMR (101 MHz, DMSO) δ 154.71, 153.48, 143.53, 140.77, 137.42, 132.86, 132.56, 130.62, 128.50, 126.93, 125.52, 122.87, 119.82, 117.38, 115.35, 70.07, 61.42, 58.37, 43.13, 42.56, 41.33, 28.04, 27.47. ESI-MS m/z: 503.1 $[M+H]^+$ HPLC $t_{ret}$=2.26 min.

Example 25

3-(Dimethylamino)-N-(4-(1-(2-methoxyethyl)-3-methyl-2-oxo-2,3-dihydro-1H-imidazo[4,5-c]quinolin-8-yl)phenyl)pyrrolidine-1-carboxamide

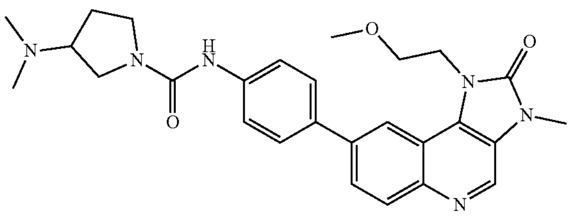

The preparation of this example was carried out following the same protocol as for example 10, but with 47 mg (47) (0,150 mmol), 63 mg (32) (0,165 mmol) and 136 mg potassiumphosphate trihydrate (0,600 mmol) in 2.5 ml Dioxan and 0.5 ml water as the starting materials. The Reaction was run at 60° C. overnight. Flash chromatography was carried out with DCM/MeOH+2N $NH_3$ (6-10%). Yield:

65 mg (89%) as white solid. $^1$H NMR (400 MHz, DMSO) δ 8.84 (s, 1H), 8.42 (s, 1H), 8.28 (s, 1H), 8.06 (d, J=8.8 Hz, 1H), 7.92 (d, J=8.9 Hz, 1H), 7.77-7.64 (m, 4H), 4.55 (t, J=5.1 Hz, 2H), 3.77 (t, J=5.3 Hz, 2H), 3.72-3.65 (m, 1H), 3.63-3.56 (m, 1H), 3.52 (s, 3H), 3.34-3.30 (m, 1H), 3.25 (s, 3H), 3.17-3.09 (m, 1H), 2.74-2.64 (m, 1H), 2.19 (s, 6H), 2.12-2.02 (m, 1H), 1.78-1.65 (m, 1H). $^{13}$C NMR (101 MHz, DMSO) δ 153.7, 153.5, 143.5, 140.6, 137.4, 132.8, 132.5, 130.6, 128.5, 126.9, 125.5, 122.9, 119.7, 117.4, 115.3, 70.1, 64.8, 58.4, 50.0, 44.9, 43.8, 42.5, 29.5, 27.5. ESI-MS m/z: 489.6 $[M+H]^+$ HPLC $t_{ret}$=2.17 min.

Example 26

3-(Dimethylamino)-N-(4-(1-(2-methoxyethyl)-3-methyl-2-oxo-2,3-dihydro-1H-imidazo[4,5-c]58uinoline-8-yl)phenyl)azetidine-1-carboxamide

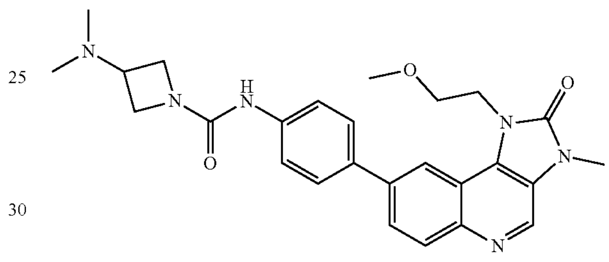

The preparation of this example was carried out following the same protocol as for example 10, but with 45 mg (47) (0.15 mmol) and 58 mg (32) (0.15 mmol) and 136 mg potassiumphosphate trihydrate (0,600 mmol) in 2.0 ml Dioxan and 0.5 ml water as the starting materials. The Reaction was run at 60° C. overnight. Flash chromatography was carried out with DCM/MeOH+2N $NH_3$ (6-10%). Yield: 55 mg (77%) as white solid. $^1$H NMR (400 MHz, DMSO) δ 8.84 (s, 1H), 8.58 (s, 1H), 8.41 (s, 1H), 8.06 (d, J=8.8 Hz, 1H), 7.91 (d, J=8.9 Hz, 1H), 7.73 (d, J=8.3 Hz, 2H), 7.67 (d, J=8.3 Hz, 2H), 4.55 (t, J=5.1 Hz, 2H), 4.04-3.94 (m, 2H), 3.83-3.73 (m, 4H), 3.53 (s, 3H), 3.24 (s, 3H), 3.09-2.99 (m, 1H), 2.10 (s, 6H). ESI-MS m/z: 475.6 $[M+H]^+$ HPLC $t_{ret}$=2.18 min.

Synthesis of compounds of formula (I), wherein the phenyl linker A is substituted

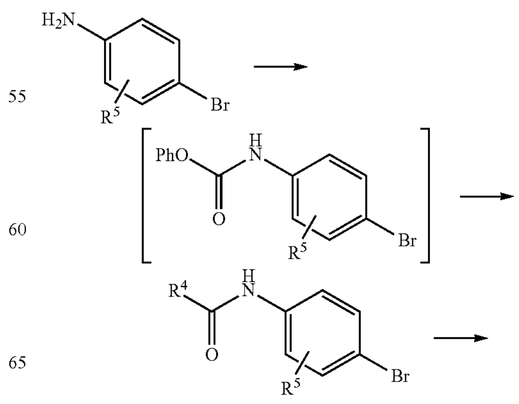

-continued

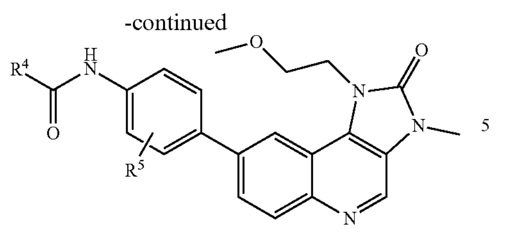

Different substitution patterns on the linking phenyl residue were accessible from the corresponding 4-bromoanilines via a two to three step procedure via an phenylcarbamate intermediate and Suzuki coupling resulting in examples 27 to 45.

Phenyl (4-bromo-3-fluorophenyl)carbamate (49)

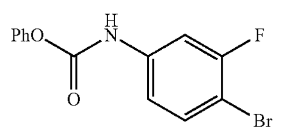 [SMILES: O=C(Nc1ccc(Br)c(F)c1)Oc1ccccc1]

To a solution of 470 mg phenyl chloroformate (3 mmol) in 5 ml THF was added a solution of 570 mg 4-bromo-3-fluoroaniline (3 mmol) in 5 ml THF dropwise over about 10 min. After complete addition, 304 mg $Et_3N$ (3 mmol) was added slowly as a solution in 2 ml THF in a rate that allowed adequate temperature control (slightly exotherm). About 15 min after complete addition, TLC indicated complete conversion and the white suspension was filtered to remove the hydrochloride salts. The filtrate was concentrated to a residual volume of about 4 ml and was then diluted slowly with hexane to induce crystallization. The white suspension was stirred in an ice bath before the solids were isolated by filtration and washed with additional hexane. Vacuum drying afforded 655 mg (70%) of the title compound as white crystalline solid. $^1H$ NMR (400 MHz, DMSO) δ 10.61 (br s, 1H), 7.64 (t, J=8.4 Hz, 1H), 7.61-7.53 (m, 1H), 7.43 (t, J=7.6 Hz, 2H), 7.34-7.17 (m, 4H). $^{13}C$ NMR (101 MHz, DMSO) δ 158.22 (d, J=242.5 Hz), 151.6, 150.2, 140.07 (d, J=10.2 Hz), 133.51 (d, J=1.1 Hz), 125.7, 121.9, 115.82 (d, J=2.5 Hz), 106.37 (d, J=27.3 Hz), 100.46 (d, J=21.0 Hz). HPLC $t_{ret}$=9.08 min.

Phenyl (4-bromo-2-fluorophenyl)carbamate (50)

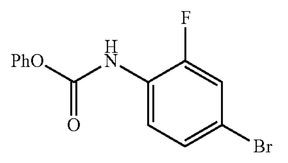 [SMILES: O=C(Nc1ccc(Br)cc1F)Oc1ccccc1]

To a solution of 939 mg phenyl chloroformate (6 mmol) in 15 ml THF was added a solution of 1140 mg 4-bromo-2-fluoroaniline (6 mmol) in 5 ml THF dropwise over about 10 min. After complete addition, 607 mg $Et_3N$ (6 mmol) was added slowly as a solution in 10 ml THF in a rate that allowed adequate temperature control (slightly exotherm). About 15 min after complete addition, TLC indicated complete conversion and the white suspension was filtered to remove the hydrochloride salts. The filtrate was concentrated to a residual volume of about 4 ml and was then diluted slowly with hexane to induce crystallization. The white suspension was stirred in an ice bath before the solids were isolated by filtration and washed with additional hexane. Vacuum drying afforded 1330 mg (72%) of the title compound as white crystalline solid. $^1H$ NMR (400 MHz, DMSO) δ 10.08 (br s, 1H), 7.68 (t, J=8.3 Hz, 1H), 7.64-7.58 (m, 1H), 7.46-7.38 (m, 3H), 7.29-7.18 (m, 3H). HPLC $t_{ret}$=8.57 min.

1-(4-Bromo-3-fluorophenyl)-3-(2-(dimethylamino)ethyl)urea (51)

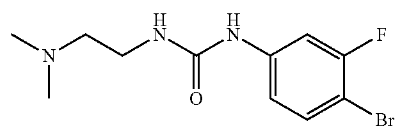 [SMILES: CN(C)CCNC(=O)Nc1ccc(Br)c(F)c1]

To a solution of 155 mg (49) (0.5 mmol) in 2 ml dioxane were added 53 mg N,N-dimethylethylendiamine (0.6 mmol). The vial was sealed and placed in a heating block at 80-90° C. After about one hour, TLC indicated complete consumption of the starting material and the mixture was diluted with EA (20 ml) and transferred to a separatory funnel. The organic phase was washed twice with 1M NaOH and once with brine, prior to drying over $Na_2SO_4$ and evaporation. The oily residue crystallized upon cooling and was triturated with hexane. The white precipitate was filtered off, washed with additional hexane and dried in vacuo to afford 137 mg (90%) of the title compound as white crystalline solid. $^1H$ NMR (400 MHz, DMSO) δ 9.02 (br s, 1H), 7.61 (d, J=12.0 Hz, 1H), 7.48 (t, J=8.4 Hz, 1H), 7.04-6.96 (m, J=8.7 Hz, 1H), 6.20 (s, 1H), 3.21-3.11 (m, 2H), 2.32 (t, J=5.9 Hz, 2H), 2.16 (s, 6H). $^{13}C$ NMR (101 MHz, DMSO) δ 158.2 (d, J=241.2 Hz), 154.7, 142.0 (d, J=10.6 Hz), 133.0 (d, J=1.3 Hz), 114.8 (d, J=2.7 Hz), 105.3 (d, J=27.4 Hz), 97.7 (d, J=21.2 Hz), 58.3, 45.0, 36.9. ESI-MS m/z: 304.1 $[M+H]^+$ HPLC $t_{ret}$=3.97 min.

1-(4-Bromo-2-fluorophenyl)-3-(2-(dimethylamino)ethyl)urea (52)

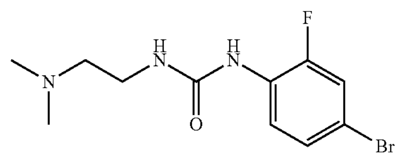 [SMILES: CN(C)CCNC(=O)Nc1ccc(Br)cc1F]

The preparation of this compound was carried out with the same procedure as described for (51) using 155 mg (50) (0.5 mmol) and 53 mg N,N-dimethylethylendiamine (0.6 mmol) as starting materials. Yield: 133 mg (88%) as white solid. $^1H$ NMR (400 MHz, DMSO) δ 8.56 (br s, 1H), 8.12 (t, J=8.7 Hz, 1H), 7.51-7.41 (m, 1H), 7.26 (d, J=8.7 Hz, 1H), 6.75-6.62 (m, 1H), 3.24-3.11 (m, 2H), 2.31 (t, J=5.7 Hz, 2H), 2.16 (s, 6H). $^{13}C$ NMR (101 MHz, DMSO) δ 154.6, 151.3 (d, J=246.0 Hz), 128.2 (d, J=10.3 Hz), 127.3 (d, J=3.3 Hz), 121.2 (d, J=1.7 Hz), 118.0 (d, J=22.6 Hz), 111.3 (d, J=9.1 Hz), 58.4, 45.0, 37.0. ESI-MS m/z: 304.1 $[M+H]^+$ HPLC $t_{ret}$=3.33 min.

N-(4-Bromo-3-fluorophenyl)-4-methylpiperazine-1-carboxamide (53)

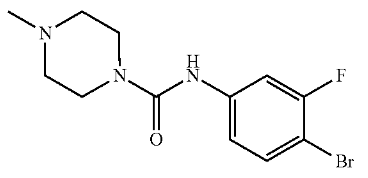 [SMILES: CN1CCN(C(=O)Nc2ccc(Br)c(F)c2)CC1]

The preparation of this compound was carried out with the same procedure as described for (51) using 155 mg (49) (0.5 mmol) and 60 mg 1-methylpiperazine (0.6 mmol) as starting materials. Yield: 139 mg (88%) as white crystalline solid. $^{1}H$ NMR (400 MHz, DMSO) δ 8.81 (br s, 1H), 7.68-7.56 (m, 1H), 7.51 (t, J=8.5 Hz, 1H), 7.31-7.19 (m, 1H), 3.49-3.39 (m, 4H), 2.39-2.26 (m, 4H), 2.19 (s, 3H). $^{13}C$ NMR (101 MHz, DMSO) δ 157.9 (d, J=240.9 Hz), 154.4, 142.1 (d, J=10.5 Hz), 132.7 (d, J=0.9 Hz), 116.4 (d, J=2.8 Hz), 107.0 (d, J=27.2 Hz), 98.6 (d, J=21.1 Hz), 54.4, 45.7, 43.6. ESI-MS m/z: 370.0 $[M+Na+MeOH]^+$ HPLC $t_{ret}$=3.73 min.

N-(4-Bromo-2-fluorophenyl)-4-methylpiperazine-1-carboxamide (54)

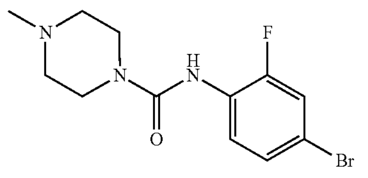 [SMILES: CN1CCN(C(=O)Nc2ccc(Br)cc2F)CC1]

The preparation of this compound was carried out with the same procedure as described for (50) using 155 mg (49) (0.5 mmol) and 60 mg 1-methylpiperazine (0.6 mmol) as starting materials. Yield: 134 mg (85%) as white solid. $^{1}H$ NMR (400 MHz, DMSO) δ 8.35 (br s, 1H), 7.54-7.46 (m, 1H), 7.40 (t, J=8.6 Hz, 1H), 7.31 (d, J=8.6 Hz, 1H), 3.46-3.37 (m, 4H), 2.35-2.26 (m, 4H), 2.19 (s, 3H). $^{13}C$ NMR (101 MHz, DMSO) δ 155.0 (d, J=250.0 Hz), 154.7, 127.4 (d, J=11.5 Hz), 127.2 (d, J=2.4 Hz), 127.0 (d, J=3.6 Hz), 118.7 (d, J=23.6 Hz), 115.2 (d, J=9.1 Hz), 54.4, 45.7, 43.7. ESI-MS m/z: 370.1 $[M+Na+MeOH]^+$ HPLC $t_{ret}$=2.63 min.

N-(4-Bromo-2-chlorophenyl)-4-methylpiperazine-1-carboxamide (55)

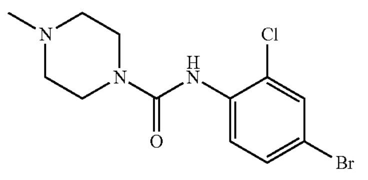 [SMILES: CN1CCN(C(=O)Nc2ccc(Br)cc2Cl)CC1]

To a solution of 103 mg 4-bromo-2-chloroaniline (0.5 mmol) in 4 ml dioxane was added 40 mg pyridine (0.5 mmol) at ambient temperature. Subsequently were added 78 mg phenylchloroformate (0.5 mmol) dropwise under vigorous stirring, resulting in formation of a white precipitate. After about 15 min, TLC indicated complete conversion to the carbamate intermediate and 75 mg N-methylpiperazine (0.6 mmol) were added in one portion. The reaction vial was placed in a heating block at 80° C. and stirring was continued until TLC indicated complete consumption of the phenyl carbamate. After cooling back to ambient temperature, the mixture was diluted with EtOAc and the organic phase was successively washed with NaOH (2×), water and brine. After drying and concentration under reduced pressure, crystallization was induced by addition of pentane. The precipitate was homogenized by addition of minor amounts of DCM combined with trituration and sonication. After aging in the freezer for about one hour, the solids were collected by filtration, washed with pentane and dried in vacuo to yield 132 mg (79%) of the title compound as beige to off-white solid. $^{1}H$ NMR (400 MHz, DMSO) δ 8.22 (br s, 1H), 7.70 (s, 1H), 7.52-7.42 (m, 2H), 3.49-3.37 (m, 4H), 2.36-2.25 (m, 4H), 2.19 (s, 3H). $^{13}C$ NMR (101 MHz, DMSO) δ 154.6, 136.4, 131.3, 130.2, 129.1, 128.2, 116.3, 54.4, 45.7, 43.7. ESI-MS m/z: 386.2 $[M+Na+MeOH]^+$ HPLC $t_{ret}$=3.15 min.

N-(4-Bromo-3-chlorophenyl)-4-methylpiperazine-1-carboxamide (56)

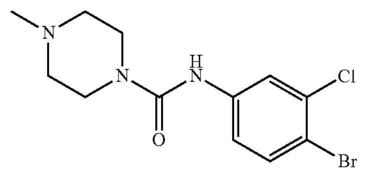

This compound was prepared via the same procedure as described for (55) with 103 mg 4-bromo-3-chloroaniline (0.5 mmol) as starting material. Yield: 130 mg (78%) as off-white solid. $^{1}H$ NMR (400 MHz, DMSO) δ 8.77 (br s, 1H), 7.84 (d, J=2.4 Hz, 1H), 7.58 (d, J=8.8 Hz, 1H), 7.38 (dd, J=8.8, 2.4 Hz, 1H), 3.48-3.38 (m, 4H), 2.37-2.26 (m, 4H), 2.19 (s, 3H). $^{13}C$ NMR (101 MHz, DMSO) δ 154.3, 141.5, 133.3, 132.6, 120.3, 119.4, 112.4, 54.4, 45.7, 43.6. ESI-MS m/z: 386.1 $[M+Na+MeOH]^+$ HPLC $t_{ret}$=4.62 min.

N-(4-Bromo-2-methylphenyl)-4-methylpiperazine-1-carboxamide (57)

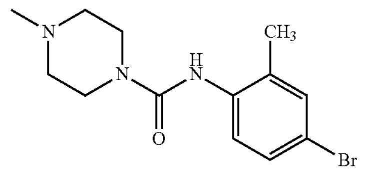 [SMILES: Cc1cc(Br)ccc1NC(=O)N1CCN(C)CC1]

This compound was prepared via the same procedure as described for (55) with 93 mg 4-bromo-2-methylaniline (0.5 mmol) as starting material. Yield: 125 mg (80%) as off-white solid. $^{1}H$ NMR (400 MHz, DMSO) δ 8.05 (br s, 1H), 7.38 (d, J=2.1 Hz, 1H), 7.29 (dd, J=8.5, 2.1 Hz, 1H), 7.15 (d, J=8.5 Hz, 1H), 3.47-3.35 (m, 4H), 2.35-2.25 (m, 4H), 2.19 (s, 3H), 2.14 (s, 3H). $^{13}C$ NMR (101 MHz, DMSO) δ 155.2, 137.6, 135.7, 132.4, 128.5, 127.6, 116.5, 54.5, 45.8, 43.7, 17.6. ESI-MS m/z: 366.2 $[M+Na+MeOH]^+$ HPLC $t_{ret}$=3.11 min.

N-(4-Bromo-3-methylphenyl)-4-methylpiperazine-1-carboxamide (58)

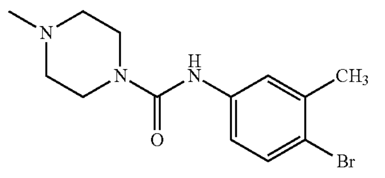

This compound was prepared via the same procedure as described for (55) with 93 mg 4-bromo-3-methylaniline (0.5 mmol) as starting material. Yield: 135 mg (87%) as off-white solid. $^1$H NMR (400 MHz, DMSO) δ 8.54 (br s, 1H), 7.46 (d, J=2.5 Hz, 1H), 7.39 (d, J=8.7 Hz, 1H), 7.26 (dd, J=8.7, 2.5 Hz, 1H), 3.46-3.38 (m, 4H), 2.33-2.28 (m, 4H), 2.27 (s, 3H), 2.19 (s, 3H). $^{13}$C NMR (101 MHz, DMSO) δ 154.7, 140.1, 136.7, 131.7, 121.8, 118.9, 115.7, 54.4, 45.7, 43.6, 22.6. ESI-MS m/z: 366.3 $[M+Na+MeOH]^+$ HPLC $t_{ret}$=4.24 min.

N-(4-Bromo-3-chloro-2-fluorophenyl)-4-methylpiperazine-1-carboxamide (59)

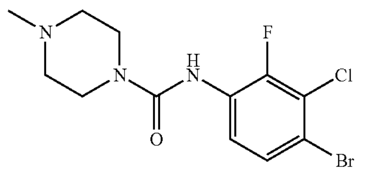 [SMILES: CN1CCN(C(=O)Nc2ccc(Br)c(Cl)c2F)CC1]

This compound was prepared via the same procedure as described for (55) with 112 mg 4-bromo-3-chloro-2-fluoroaniline (0.5 mmol) as starting material. Yield: 137 mg (78%) as off-white solid. $^1$H NMR (400 MHz, DMSO) δ 8.56 (br s, 1H), 7.57-7.47 (m, 1H), 7.43-7.33 (m, 1H), 3.49-3.36 (m, 4H), 2.36-2.27 (m, 4H), 2.19 (s, 3H). $^{13}$C NMR (101 MHz, DMSO) δ 154.9, 151.3 (d, J=250.5 Hz), 128.9 (d, J=11.9 Hz), 127.9 (d, J=4.0 Hz), 125.0 (d, J=2.4 Hz), 121.0 (d, J=18.4 Hz), 116.1 (d, J=0.9 Hz), 54.8, 46.2, 44.2. ESI-MS m/z: 350.2 $[M+H]^+$ HPLC $t_{ret}$=4.20 min.

N-(4-Bromo-5-chloro-2-fluorophenyl)-4-methylpiperazine-1-carboxamide (60)

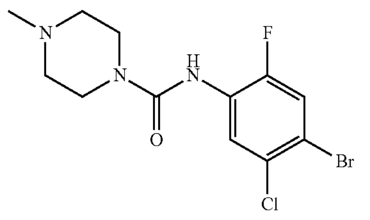 [SMILES: CN1CCN(C(=O)Nc2cc(Cl)c(Br)cc2F)CC1]

This compound was prepared via the same procedure as described for (55) with 112 mg 4-bromo-5-chloro-2-fluoroaniline (0.5 mmol) as starting material. Yield: 142 mg (81%) as off-white solid. $^1$H NMR (400 MHz, DMSO) δ 8.51 (br s, 1H), 7.79 (d, J=7.4 Hz, 1H), 7.73 (d, J=10.1 Hz, 1H), 3.46-3.38 (m, 4H), 2.34-2.26 (m, 4H), 2.19 (s, 3H). $^{13}$C NMR (101 MHz, DMSO) δ 154.3, 152.9 (d, J=249.8 Hz), 128.9 (d, J=12.6 Hz), 128.0 (d, J=3.6 Hz), 125.4 (d, J=2.6 Hz), 120.5 (d, J=24.8 Hz), 114.5 (d, J=9.3 Hz), 54.3, 45.7, 43.7. ESI-MS m/z: 404.3 $[M+Na+MeOH]^+$ HPLC $t_{ret}$=4.30 min.

N-(4-Bromo-3-fluoro-2-methylphenyl)-4-methylpiperazine-1-carboxamide (61)

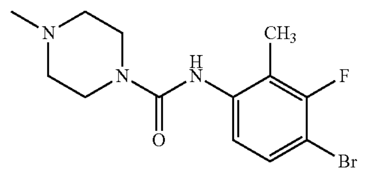 [SMILES: Cc1c(NC(=O)N2CCN(C)CC2)ccc(Br)c1F]

This compound was prepared via the same procedure as described for (55) with 102 mg 4-bromo-3-fluoro-2-methylaniline (0.5 mmol) as starting material. Yield: 132 mg (80%) as off-white solid. $^1$H NMR (400 MHz, DMSO) δ 8.29 (br s, 1H), 7.48-7.36 (m, 1H), 7.01 (dd, J=8.7, 1.0 Hz, 1H), 3.47-3.37 (m, 4H), 2.35-2.28 (m, 4H), 2.19 (s, 3H), 2.08 (d, J=2.4 Hz, 3H). $^{13}$C NMR (101 MHz, DMSO) δ 156.5 (d, J=240.9 Hz), 155.1, 139.7 (d, J=6.1 Hz), 129.2 (d, J=1.3 Hz), 122.6 (d, J=3.2 Hz), 122.0 (d, J=18.3 Hz), 102.9 (d, J=22.4 Hz), 54.4, 45.7, 43.7, 10.6 (d, J=4.4 Hz). ESI-MS m/z: 384.1 $[M+Na+MeOH]^+$ HPLC $t_{ret}$=3.61 min.

N-(4-Bromo-3-chloro-2-methylphenyl)-4-methylpiperazine-1-carboxamide (62)

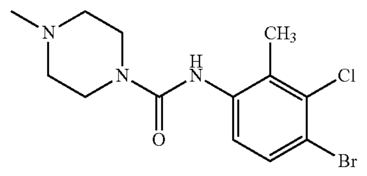 [SMILES: Cc1c(NC(=O)N2CCN(C)CC2)ccc(Br)c1Cl]

This compound was prepared via the same procedure as described for (55) with 110 mg 4-bromo-3-chloro-2-methylaniline (0.5 mmol) as starting material. Yield: 152 mg (88%) as off-white solid. $^1$H NMR (400 MHz, DMSO) δ 8.35 (br s, 1H), 7.53 (d, J=8.6 Hz, 1H), 7.10 (d, J=8.6 Hz, 1H), 3.49-3.37 (m, 4H), 2.34-2.27 (m, 4H), 2.23 (s, 3H), 2.20 (s, 3H). $^{13}$C NMR (101 MHz, DMSO) δ 155.2, 139.1, 134.1, 133.2, 130.1, 126.2, 117.5, 54.5, 45.7, 43.7, 17.0. ESI-MS m/z: 346.1 $[M+H]^+$ HPLC $t_{ret}$=4.48 min.

N-(4-Bromo-5-fluoro-2-methylphenyl)-4-methylpiperazine-1-carboxamide (63)

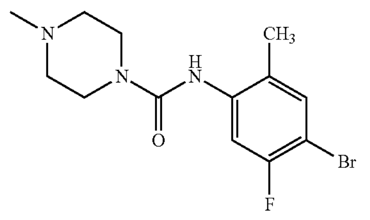 [SMILES: Cc1cc(Br)c(F)cc1NC(=O)N1CCN(C)CC1]

This compound was prepared via the same procedure as described for (55) with 102 mg 4-bromo-5-fluoro-2-methylaniline (0.5 mmol) as starting material. Yield: 136 mg (82%) as off-white solid. $^1$H NMR (400 MHz, DMSO) δ 8.09 (br s, 1H), 7.49 (d, J=7.9 Hz, 1H), 7.32 (d, J=10.8 Hz, 1H), 3.48-3.38 (m, 4H), 2.36-2.26 (m, 4H), 2.19 (s, 3H), 2.14 (s, 3H). $^{13}$C NMR (101 MHz, DMSO) δ 156.0 (d, J=240.8 Hz), 154.8, 139.1 (d, J=9.6 Hz), 133.5 (d, J=0.8 Hz), 129.9 (d, J=3.2 Hz), 112.6 (d, J=24.3 Hz), 101.7 (d, J=20.7 Hz), 54.4, 45.7, 43.7, 16.9. ESI-MS m/z: 384.3 $[M+Na+MeOH]^+$ HPLC $t_{ret}$=3.78 min.

N-(4-Bromo-5-chloro-2-methylphenyl)-4-methylpiperazine-1-carboxamide (64)

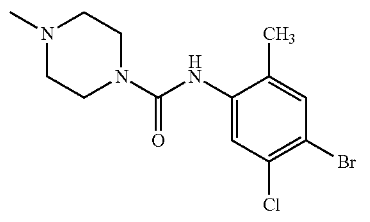 [SMILES: Cc1cc(Br)c(Cl)cc1NC(=O)N1CCN(C)CC1]

This compound was prepared via the same procedure as described for (55) with 102 mg 4-bromo-5-chloro-2-methylaniline (0.5 mmol) as starting material. Yield: 153 mg (92%) as off-white solid. $^1$H NMR (400 MHz, DMSO) δ 8.12 (br s, 1H), 7.57 (s, 1H), 7.51 (s, 1H), 3.47-3.37 (m, 4H), 2.34-2.26 (m, 4H), 2.19 (s, 3H), 2.15 (s, 3H). $^{13}$C NMR (101 MHz, DMSO) δ 154.9, 139.0, 134.4, 133.6, 129.5, 126.2, 115.6, 54.4, 45.7, 43.7, 17.1. ESI-MS m/z: 346.2 $[M+H]^+$ HPLC $t_{ret}$=4.56 min.

N-(4-Bromo-2,5-difluorophenyl)-4-methylpiperazine-1-carboxamide (65)

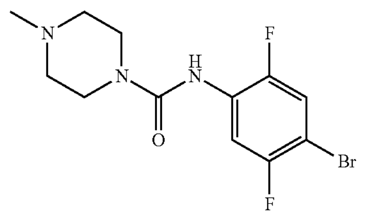 [SMILES: CN1CCN(C(=O)Nc2cc(F)c(Br)cc2F)CC1]

This compound was prepared via the same procedure as described for (55) with 104 mg 4-bromo-2,5-difluoroaniline (0.5 mmol) as starting material. Yield: 119 mg (71%) as off-white solid. $^1$H NMR (400 MHz, DMSO) δ 8.51 (br s, 1H), 7.72-7.64 (m, 1H), 7.63-7.51 (m, 1H), 3.48-3.38 (m, 4H), 2.35-2.25 (m, 4H), 2.19 (s, 3H). $^{13}$C NMR (101 MHz, DMSO) δ 154.3, 154.2 (dd, J=239.3, 2.7 Hz), 150.4 (dd, J=245.4, 2.5 Hz), 128.9 (dd, J=13.2, 10.5 Hz), 119.4 (dd, J=25.4, 1.1 Hz), 111.8 (dd, J=28.1, 2.5 Hz), 100.4 (dd, J=23.7, 9.5 Hz), 54.3, 45.7, 43.7. ESI-MS m/z: 388.1 $[M+H]^+$ HPLC $t_{ret}$=3.28 min.

N-(4-Bromo-2,3-difluorophenyl)-4-methylpiperazine-1-carboxamide (66)

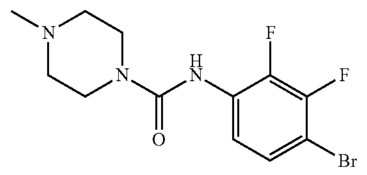 [SMILES: CN1CCN(C(=O)Nc2ccc(Br)c(F)c2F)CC1]

This compound was prepared via the same procedure as described for (55) with 104 mg 4-bromo-2,3-difluoroaniline (0.5 mmol) as starting material. Yield: 129 mg (78%) as off-white solid. $^1$H NMR (400 MHz, DMSO) δ 8.61 (br s, 1H), 7.47-7.36 (m, 1H), 7.28-7.16 (m, 1H), 3.47-3.39 (m, 4H), 2.36-2.26 (m, 4H), 2.19 (s, 3H). $^{13}$C NMR (101 MHz, DMSO) δ 154.3, 147.4 (dd, J=243.7, 13.4 Hz), 143.9 (dd, J=250.7, 14.4 Hz), 129.7 (dd, J=8.9, 1.3 Hz), 126.7 (d, J=4.0 Hz), 121.4 (dd, J=3.1, 1.2 Hz), 102.7 (d, J=17.6 Hz), 54.3, 45.7, 43.7. ESI-MS m/z: 332.2 $[M-]^-$ HPLC $t_{ret}$=3.31 min.

N-(4-Bromo-2,6-difluorophenyl)-4-methylpiperazine-1-carboxamide (67)

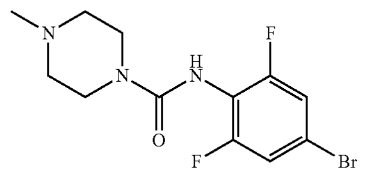 [SMILES: CN1CCN(C(=O)Nc2c(F)cc(Br)cc2F)CC1]

To a solution of 103 mg 4-bromo-2,6-difluoroaniline (0.5 mmol) in 4 ml dioxane were added 40 mg pyridine at ambient temperature. Subsequently 78 mg phenylchloroformate (0.5 mmol) were added dropwise under vigorous stirring, resulting in formation of a white precipitate. After 2 hours, TLC indicated incomplete conversion and additional 4 mg pyridine (0.05 mmol) and 8 mg phenylchloroformate (0.05 mmol) were added. After additional 5 hours at ambient temperature, 75 mg N-methylpiperazine (0.8 mmol) were added in one portion. The reaction vial was placed in a heating block at 80° C. and stirring was continued until TLC indicated complete consumption of the phenyl carbamate (about 4 hours). After cooling to ambient temperature, the mixture was diluted with EA and the organic phase was successively washed with water, NaOH (2×) and brine. After drying and concentration under reduced pressure, crystallization was induced by addition of pentane. The precipitate was homogenized by addition of minor amounts of DCM combined with trituration and sonication. After aging in the freezer for about one hour, the solids were collected by filtration, washed with pentane and dried in vacuo to yield 115 mg (69%) of the title compound as beige to off-white solid. $^{1}H$ NMR (400 MHz, DMSO) δ 8.29 (br s, 1H), 7.47 (d, J=6.8 Hz, 2H), 3.51-3.32 (m, 4H), 2.37-2.25 (m, 4H), 2.19 (s, 3H). $^{13}C$ NMR (101 MHz, DMSO) δ 158.1 (dd, J=251.1, 6.3 Hz), 154.6, 117.3 (t, J=12.2 Hz), 116.6 (t, J=16.4 Hz), 115.7-115.1 (m), 54.3, 45.7, 43.7. ESI-MS m/z: 388.1 $[M+Na+MeOH]^+$ HPLC $t_{ret}$=2.35 min.

N-(4-Bromo-3,5-difluorophenyl)-4-methylpiperazine-1-carboxamide (68)

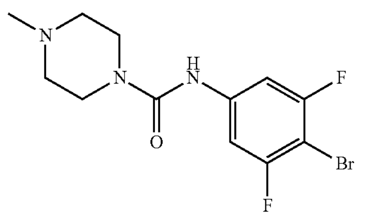 [SMILES: CN1CCN(C(=O)Nc2cc(F)c(Br)c(F)c2)CC1]

This compound was prepared via the same procedure as described for (55) with 104 mg 4-bromo-3,5-difluoroaniline (0.5 mmol) as starting material. Yield: 155 mg (93%) as off-white solid. $^{1}H$ NMR (400 MHz, DMSO) δ 8.96 (br s, 1H), 7.42 (d, J=10.6 Hz, 2H), 3.51-3.36 (m, 4H), 2.37-2.24 (m, 4H), 2.19 (s, 3H). $^{13}C$ NMR (101 MHz, DMSO) δ 158.9 (dd, J=241.4, 6.8 Hz), 154.0, 142.4 (t, J=13.5 Hz), 102.5 (dd, J=27.9, 2.4 Hz), 87.2 (t, J=25.2 Hz), 54.3, 45.6, 43.5. ESI-MS m/z: 332.2 $[M-]^-$ HPLC $t_{ret}$=4.55 min.

N-(4-Bromo-2-fluoro-5-methylphenyl)-4-methylpiperazine-1-carboxamide (69)

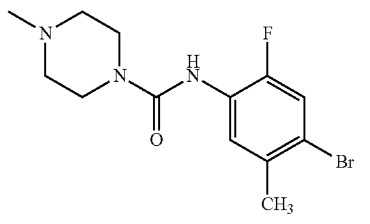 [SMILES: Cc1cc(NC(=O)N2CCN(C)CC2)c(F)cc1Br]

This compound was prepared via the same procedure as described for (55) with 102 mg 4-bromo-2-fluoro-5-methylaniline (0.5 mmol) as starting material. Yield: 130 mg (79%) as off-white solid. $^{1}H$ NMR (400 MHz, DMSO) δ 8.30 (br s, 1H), 7.48 (d, J=10.1 Hz, 1H), 7.42 (d, J=8.4 Hz, 1H), 3.48-3.36 (m, 4H), 2.32-2.28 (m, 4H), 2.27 (s, 3H), 2.19 (s, 3H). $^{13}C$ NMR (101 MHz, DMSO) δ 154.7, 153.25 (d, J=247.4 Hz), 132.76 (d, J=3.7 Hz), 127.59 (d, J=2.0 Hz), 127.04 (d, J=11.6 Hz), 118.87 (d, J=23.4 Hz), 117.41 (d, J=9.0 Hz), 54.4, 45.7, 43.7, 21.6. ESI-MS m/z: 384.2 $[M+Na+MeOH]^+$ HPLC $t_{ret}$=3.83 min.

Example 27

1-(2-(Dimethylamino)ethyl)-3-(3-fluoro-4-(1-(2-methoxyethyl)-3-methyl-2-oxo-2,3-dihydro-1H-imidazo[4,5-c]quinolin-8-yl)phenyl)urea

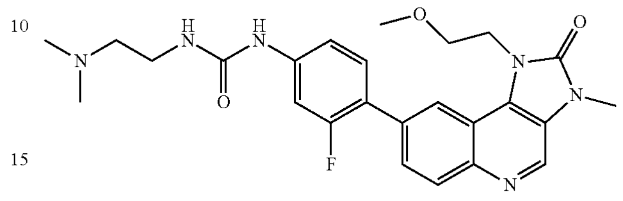

The preparation of this final compound was performed following the same procedure as described above for example 12 using 42 mg (32) (0.11 mmol) and 33 mg (51) (0.11 mmol) as the starting materials. Flash chromatography with DCM/MeOH+2N $NH_3$ (2-10%) yielded 30 mg (57%) of the title compound as white solid. $^{1}H$ NMR (400 MHz, DMSO) δ 9.10 (br s, 1H), 8.88 (s, 1H), 8.36 (s, 1H), 8.07 (d, J=8.9 Hz, 1H), 7.83-7.70 (m, 1H), 7.61 (dd, J=14.2, 1.8 Hz, 1H), 7.56 (t, J=8.9 Hz, 1H), 7.19 (dd, J=8.5, 1.8 Hz, 1H), 6.28 (t, J=5.0 Hz, 1H), 4.50 (t, J=5.5 Hz, 2H), 3.75 (t, J=5.5 Hz, 2H), 3.54 (s, 3H), 3.22 (s, 3H), 3.22-3.17 (m, 2H), 2.34 (t, J=6.1 Hz, 2H), 2.18 (s, 6H). ESI-MS m/z: 481.1 $[M+H]^+$ HPLC $t_{ret}$=2.46 min.

Example 28

1-(2-(Dimethylamino)ethyl)-3-(2-fluoro-4-(1-(2-methoxyethyl)-3-methyl-2-oxo-2,3-dihydro-1H-imidazo[4,5-c]quinolin-8-yl)phenyl)urea

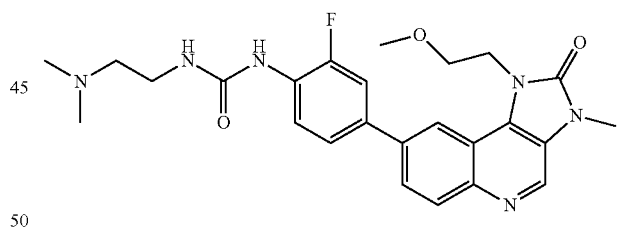

The preparation of this final compound was performed following the same procedure as described above for example 12 using 42 mg (32) (0.11 mmol) and 33 mg (52) (0.11 mmol) as the starting materials. Flash chromatography with DCM/MeOH+2N $NH_3$ (1-10%) yielded 29 mg (55%) of the title compound as white solid. $^{1}H$ NMR (400 MHz, DMSO) δ 8.86 (s, 1H), 8.63 (br s, 1H), 8.44 (d, J=1.8 Hz, 1H), 8.30 (t, J=8.7 Hz, 1H), 8.06 (d, J=8.9 Hz, 1H), 7.93 (dd, J=8.9, 1.8 Hz, 1H), 7.69 (dd, J=13.0, 2.0 Hz, 1H), 7.59 (dd, J=8.7, 1.8 Hz, 1H), 6.74 (t, J=5.2 Hz, 1H), 4.57 (t, J=5.5 Hz, 2H), 3.77 (t, J=5.5 Hz, 2H), 3.53 (s, 3H), 3.24 (s, 3H), 3.23-3.18 (m, 2H), 2.34 (t, J=6.1 Hz, 2H), 2.19 (s, 6H). ESI-MS m/z: 481.4 $[M+H]^+$ HPLC $t_{ret}$=2.23 min.

Example 29

N-(3-Fluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

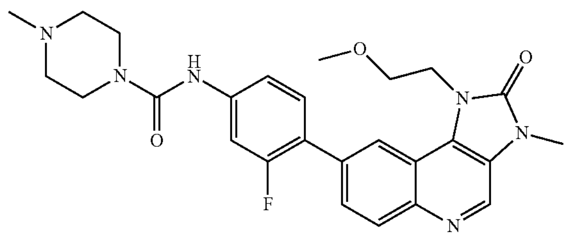

The preparation of this final compound was performed following the same procedure as described above for example 12 using 42 mg (32) (0.11 mmol) and 35 mg (53) (0.11 mmol) as the starting materials. Flash chromatography with DCM/MeOH+2N $NH_3$ (1-10%) yielded 32 mg (59%) of the title compound as white solid. $^1$H NMR (400 MHz, DMSO) δ 8.94-8.78 (m, 2H), 8.36 (s, 1H), 8.07 (d, J=8.8 Hz, 1H), 7.78 (d, J=8.8 Hz, 1H), 7.67-7.51 (m, 2H), 7.49-7.37 (m, 1H), 4.49 (t, J=5.5 Hz, 2H), 3.75 (t, J=5.5 Hz, 2H), 3.53 (s, 3H), 3.50-3.41 (m, 4H), 3.22 (s, 3H), 2.39-2.29 (m, 4H), 2.21 (s, 3H). ESI-MS m/z: 493.1 $[M+H]^+$ HPLC $t_{ret}$=2.25 min.

Example 30

N-(2-Fluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

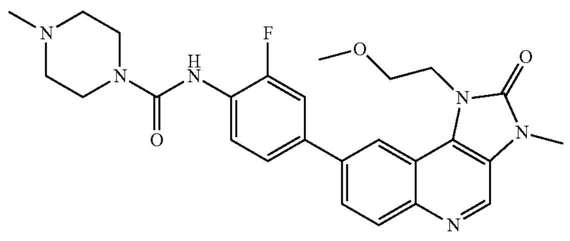

The preparation of this final compound was performed following the same procedure as described above for example 12 using 42 mg (32) (0.11 mmol) and 35 mg (54) (0.11 mmol) as the starting materials. Flash chromatography with DCM/MeOH+2N $NH_3$ (1-7%) yielded 33 mg (61%) of the title compound as white solid. $^1$H NMR (400 MHz, DMSO) δ 8.87 (s, 1H), 8.48 (d, J=1.4 Hz, 1H), 8.42 (s, 1H), 8.08 (d, J=8.9 Hz, 1H), 7.95 (dd, J=8.9, 1.7 Hz, 1H), 7.74-7.67 (m, 1H), 7.65-7.54 (m, 2H), 4.58 (t, J=5.5 Hz, 2H), 3.77 (t, J=5.5 Hz, 2H), 3.53 (s, 3H), 3.50-3.40 (m, 4H), 3.24 (s, 3H), 2.40-2.29 (m, 4H), 2.22 (s, 3H). ESI-MS m/z: 493.4 $[M+H]^+$ HPLC $t_{ret}$=1.73 min.

Example 31

N-(2-Chloro-4-(1-(2-methoxyethyl)-3-methyl-2-oxo-2,3-dihydro-1H-imidazo[4,5-c]quinolin-8-yl)phenyl)-4-methylpiperazine-1-carboxamide

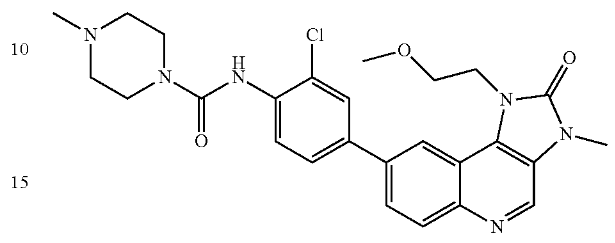

In a screw-top reaction vial were dissolved 42 mg (32) (0.11 mmol) and 37 mg (55) (0.11 mmol) in dioxane under argon atmosphere. Subsequently 0.66 ml of an 0.5 M aqueous $K_3PO_4$ solution (0.33 mmol) were added via syringe and the mixture was degassed by three vacuum/argon cycles. Then, 0.05 ml of a stock solution of tBu3P Pd G3 in dioxane (20 mg/ml, 1.5 mol %) were added and the degassing procedure was repeated. The reaction vial was sealed and placed in a heating block at 70° C. TLC indicated complete conversion after about 3 hours and the reaction mixture was diluted with EA. The organic phase was washed with brine, dried over $Na_2SO_4$ and concentrated under reduced pressure. The residue was taken up in a small amount acetonitrile and stored overnight in the freezer overnight for complete precipitation. The solids were collected by filtration and sparingly washed with chilled acetonitrile. Additional purification via flash chromatography (DCM/MeOH+2N $NH_3$ 1-7%) yielded 20 mg (36%) of the title compound as white solid. $^1$H NMR (400 MHz, DMSO) δ 8.89 (br s, 1H), 8.51 (s, 1H), 8.25 (s, 1H), 8.09 (d, J=8.8 Hz, 1H), 7.96 (d, J=8.8 Hz, 1H), 7.92 (s, 1H), 7.77 (d, J=8.4 Hz, 1H), 7.68 (d, J=8.4 Hz, 1H), 4.58 (t, J=5.2 Hz, 2H), 3.78 (t, J=5.2 Hz, 2H), 3.54 (s, 3H), 3.51-3.42 (m, 4H), 3.26 (s, 3H), 2.39-2.29 (m, 4H), 2.21 (s, 3H). $^{13}$C NMR (101 MHz, DMSO) δ 154.9, 153.5, 143.8, 136.7, 136.4, 135.8, 133.3, 130.8, 128.7, 128.3, 127.5, 126.9, 125.8, 125.5, 123.0, 118.6, 115.2, 70.2, 58.4, 54.4, 45.7, 43.8, 42.6, 27.5. ESI-MS m/z: 509.5 $[M+H]^+$ HPLC $t_{ret}$=2.56 min.

Example 32

N-(3-Chloro-4-(1-(2-methoxyethyl)-3-methyl-2-oxo-2,3-dihydro-1H-imidazo[4,5-c]quinolin-8-yl)phenyl)-4-methylpiperazine-1-carboxamide

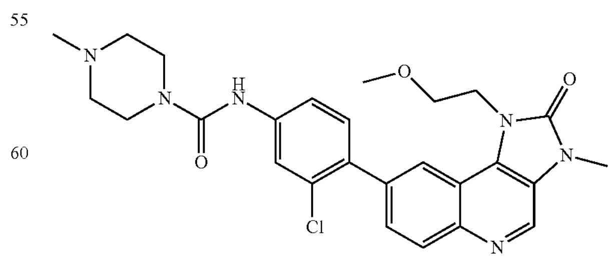

The preparation of this compound was carried out following the above described procedure for the synthesis of the compound of example 31, but with 37 mg (56) (0.11 mmol) as the aryl bromide starting material. Yield: 27 mg (48%) as a white solid. $^1$H NMR (400 MHz, DMSO) δ 8.95-8.89 (m, 1H), 8.81 (s, 1H), 8.30-8.25 (m, 1H), 8.08 (dd, J=8.8, 1.0 Hz, 1H), 7.86-7.81 (m, 1H), 7.71-7.66 (m, 1H), 7.59-7.54 (m, 1H), 7.45 (dd, J=8.5, 1.1 Hz, 1H), 4.47 (t, J=5.4 Hz, 2H), 3.73 (t, J=5.4 Hz, 2H), 3.54 (s, 3H), 3.49-3.44 (m, 4H), 3.21 (s, 3H), 2.36-2.30 (m, 4H), 2.21 (s, 3H). ESI-MS m/z: 509.3 [M+H]$^+$ HPLC $t_{ret}$=3.15 min.

Example 33

N-(4-(1-(2-Methoxyethyl)-3-methyl-2-oxo-2,3-dihydro-1H-imidazo[4,5-c]quinolin-8-yl)-2-methyl phenyl)-4-methylpiperazine-1-carboxamide

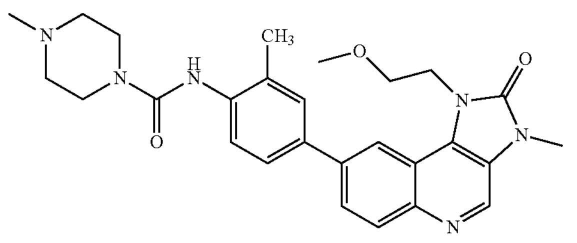

The preparation of this compound was carried out following the above described procedure for the synthesis of the compound of example 31, but with 34 mg (57) (0.11 mmol) as the aryl bromide starting material. Yield: 36 mg (67%) as a white solid. $^1$H NMR (400 MHz, DMSO) δ 8.85 (br s, 1H), 8.45 (s, 1H), 8.12 (s, 1H), 8.07 (d, J=8.9 Hz, 1H), 7.92 (d, J=8.9 Hz, 1H), 7.64 (s, J=9.2 Hz, 1H), 7.60 (d, J=8.1 Hz, 1H), 7.36 (d, J=8.1 Hz, 1H), 4.54 (t, J=5.2 Hz, 2H), 3.77 (t, J=5.2 Hz, 2H), 3.53 (s, 3H), 3.50-3.42 (m, 4H), 3.26 (s, 3H), 2.38-2.30 (m, 4H), 2.28 (s, 3H), 2.22 (s, 3H). $^{13}$C NMR (101 MHz, DMSO) δ 155.5, 153.5, 143.6, 138.0, 137.4, 135.6, 133.3, 133.0, 130.6, 128.8, 128.6, 126.1, 125.7, 124.4, 122.9, 118.0, 115.3, 70.1, 58.4, 54.5, 45.7, 43.8, 42.6, 27.5, 18.2. ESI-MS m/z: 489.6 [M+H]$^+$ HPLC $t_{ret}$=2.15 min.

Example 34

N-(4-(1-(2-Methoxyethyl)-3-methyl-2-oxo-2,3-dihydro-1H-imidazo[4,5-c]quinolin-8-yl)-3-methylphenyl)-4-methylpiperazine-1-carboxamide

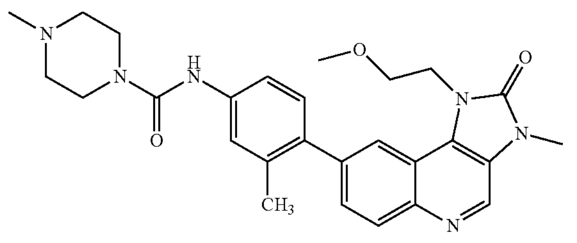

The preparation of this compound was carried out following the above described procedure for the synthesis of the compound of example 31, but with 34 mg (58) (0.11 mmol) as the aryl bromide starting material. Yield: 46 mg (86%) as a white solid. $^1$H NMR (400 MHz, DMSO) δ 8.88 (br s, 1H), 8.56 (s, 1H), 8.14 (s, 1H), 8.05 (d, J=8.7 Hz, 1H), 7.60 (d, J=8.7 Hz, 1H), 7.50-7.39 (m, 2H), 7.23 (d, J=8.1 Hz, 1H), 4.45 (t, J=5.2 Hz, 2H), 3.71 (t, J=5.2 Hz, 2H), 3.53 (s, 3H), 3.46 (M, 4H), 3.20 (s, 3H), 2.33 (M, 4H), 2.29 (s, 3H), 2.21 (s, 3H). $^{13}$C NMR (101 MHz, DMSO) δ 155.0, 153.4, 143.3, 140.1, 138.9, 134.8, 134.2, 133.0, 129.9, 129.8, 128.5, 128.4, 122.8, 121.3, 120.6, 117.3, 114.9, 69.9, 58.3, 54.5, 45.7, 43.7, 42.5, 27.5, 20.5. ESI-MS m/z: 489.5 [M+H]$^+$ HPLC $t_{ret}$=2.33 min.

Example 35

N-(3-Chloro-2-fluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

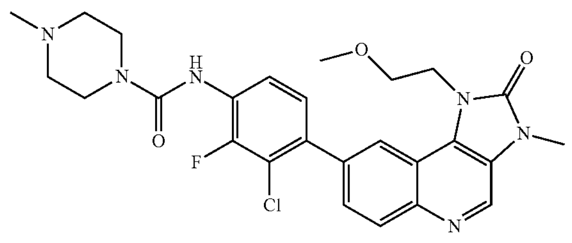

The preparation of this compound was carried out following the above described procedure for the synthesis of the compound of example 31, but with 39 mg (59) (0.11 mmol) as the aryl bromide starting material. Yield: 23 mg (40%) as a white solid. $^1$H NMR (400 MHz, DMSO) δ 8.94 (br s, 1H), 8.60 (s, 1H), 8.33 (s, 1H), 8.11 (d, J=8.7 Hz, 1H), 7.70 (d, J=8.7 Hz, 1H), 7.58-7.48 (m, 1H), 7.34 (d, J=8.3 Hz, 1H), 4.48 (t, J=5.4 Hz, 2H), 3.73 (t, J=5.4 Hz, 2H), 3.53 (s, 3H), 3.51-3.40 (m, 4H), 3.20 (s, 3H), 2.39-2.29 (m, 4H), 2.22 (s, 3H). ESI-MS m/z: 527.5 [M+H]$^+$ HPLC $t_{ret}$=3.03 min.

Example 36

N-(5-Chloro-2-fluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

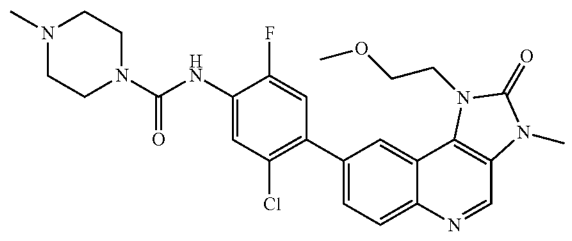

The preparation of this compound was carried out following the above described procedure for the synthesis of the compound of example 31, but with 39 mg (60) (0.11 mmol) as the aryl bromide starting material. Yield: 34 mg (59%) as a white solid. $^1$H NMR (400 MHz, DMSO) δ 8.93 (br s, 1H), 8.56 (s, 1H), 8.33 (s, 1H), 8.10 (d, J=8.8 Hz, 1H), 7.78 (d, J=7.1 Hz, 1H), 7.72 (d, J=8.8 Hz, 1H), 7.48 (d, J=11.1 Hz, 1H), 4.49 (t, J=5.1 Hz, 2H), 3.73 (t, J=5.1 Hz, 2H), 3.55 (s, 3H), 3.51-3.41 (m, 4H), 3.21 (s, 3H), 2.40-2.27 (m, 4H), 2.21 (s, 3H). ESI-MS m/z: 527.5 $[M+H]^+$ HPLC $t_{ret}$=3.09 min.

Example 37

N-(3-Fluoro-4-(1-(2-methoxyethyl)-3-methyl-2-oxo-2,3-dihydro-1H-imidazo[4,5-c]quinolin-8-yl)-2-methylphenyl)-4-methylpiperazine-1-carboxamide

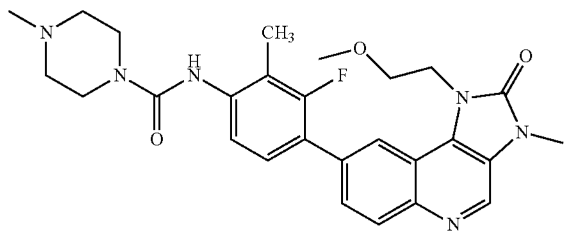

The preparation of this compound was carried out following the above described procedure for the synthesis of the compound of example 31, but with 36 mg (61) (0.11 mmol) as the aryl bromide starting material. Yield: 21 mg (38%) as a white solid. $^1$H NMR (400 MHz, DMSO) δ 8.91 (br s, 1H), 8.39 (s, 1H), 8.35 (s, 1H), 8.10 (d, J=8.8 Hz, 1H), 7.79 (d, J=8.8 Hz, 1H), 7.44 (t, J=8.5 Hz, 1H), 7.20 (d, J=8.3 Hz, 1H), 4.50 (t, J=5.4 Hz, 2H), 3.76 (t, J=5.4 Hz, 2H), 3.54 (s, 3H), 3.50-3.43 (m, 4H), 3.23 (s, 3H), 2.39-2.31 (m, 4H), 2.22 (s, 3H), 2.14 (s, 3H). ESI-MS m/z: 507.5 $[M+H]^+$ HPLC $t_{ret}$=2.64 min.

Example 38

N-(3-Chloro-4-(1-(2-methoxyethyl)-3-methyl-2-oxo-2,3-dihydro-1H-imidazo[4,5-c]quinolin-8-yl)-2-methylphenyl)-4-methylpiperazine-1-carboxamide

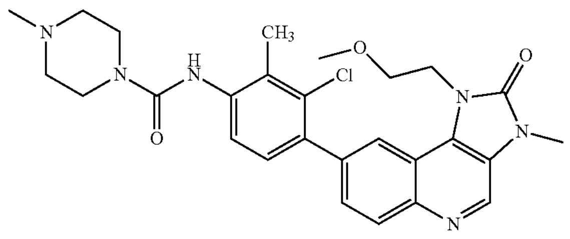

The preparation of this compound was carried out following the above described procedure for the synthesis of the compound of example 31, but with 38 mg (62) (0.11 mmol) as the aryl bromide starting material. Yield: 35 mg (61%) as a white solid. $^1$H NMR (400 MHz, DMSO) δ 8.92 (br s, 1H), 8.41 (s, 1H), 8.27 (s, 1H), 8.09 (d, J=8.8 Hz, 1H), 7.66 (d, J=8.8 Hz, 1H), 7.32 (d, J=8.2 Hz, 1H), 7.27 (d, J=8.2 Hz, 1H), 4.46 (t, J=5.1 Hz, 2H), 3.72 (t, J=5.1 Hz, 2H), 3.55 (s, 3H), 3.52-3.43 (m, 4H), 3.20 (s, 3H), 2.40-2.31 (m, 4H), 2.27 (s, 3H), 2.22 (s, 3H). $^{13}$C NMR (101 MHz, DMSO) δ 155.5, 153.5, 143.5, 139.2, 137.3, 136.3, 133.4, 132.4, 132.0, 129.7, 128.6, 128.3, 128.2, 124.9, 122.9, 121.5, 114.7, 69.8, 58.3, 54.5, 45.7, 43.7, 42.4, 27.5, 16.2. ESI-MS m/z: 523.7 $[M+H]^+$ HPLC $t_{ret}$=3.06 min.

Example 39

N-(5-Fluoro-4-(1-(2-methoxyethyl)-3-methyl-2-oxo-2,3-dihydro-1H-imidazo[4,5-c]quinolin-8-yl)-2-methylphenyl)-4-methylpiperazine-1-carboxamide

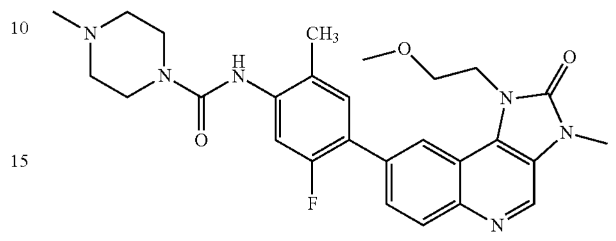

The preparation of this compound was carried out following the above described procedure for the synthesis of, but with 36 mg (63) (0.11 mmol) as the aryl bromide starting material. Yield: 32 mg (61%) as a white solid. $^1$H NMR (400 MHz, DMSO) δ 8.89 (br s, 1H), 8.40 (s, 1H), 8.13 (d, J=9.5 Hz, 1H), 8.09 (d, J=8.8 Hz, 1H), 7.80 (d, J=8.8 Hz, 1H), 7.49 (d, J=8.8 Hz, 1H), 7.34 (d, J=12.7 Hz, 1H), 4.49 (t, J=5.2 Hz, 2H), 3.75 (t, J=5.2 Hz, 2H), 3.54 (s, 3H), 3.50-3.42 (m, 4H), 3.24 (s, 3H), 2.38-2.30 (m, 4H), 2.24 (s, 3H), 2.21 (s, 3H). ESI-MS m/z: 507.5 $[M+H]^+$ HPLC $t_{ret}$=2.56 min.

Example 40

N-(5-Chloro-4-(1-(2-methoxyethyl)-3-methyl-2-oxo-2,3-dihydro-1H-imidazo[4,5-c]quinolin-8-yl)-2-methylphenyl)-4-methylpiperazine-1-carboxamide

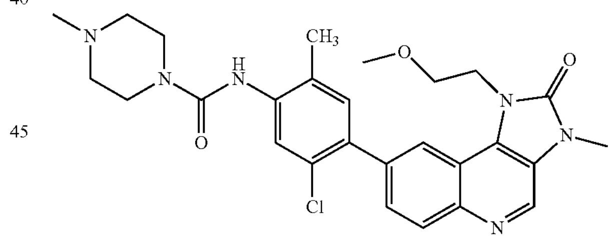

The preparation of this compound was carried out following the above described procedure for the synthesis of the compound of example 31, but with 38 mg (64) (0.11 mmol) as the aryl bromide starting material. Yield: 29 mg (50%) as a white solid. $^1$H NMR (400 MHz, DMSO) δ 8.92 (br s, 1H), 8.31 (s, 1H), 8.19 (s, 1H), 8.09 (d, J=8.8 Hz, 1H), 7.70 (d, J=8.8 Hz, 1H), 7.51 (s, 1H), 7.38 (s, 1H), 4.47 (t, J=5.3 Hz, 2H), 3.73 (t, J=5.3 Hz, 2H), 3.54 (s, 3H), 3.51-3.42 (m, 4H), 3.22 (s, 3H), 2.39-2.29 (m, 4H), 2.23 (s, 3H), 2.21 (s, 3H). $^{13}$C NMR (101 MHz, DMSO) δ 155.2, 153.4, 143.5, 139.0, 136.1, 134.7, 133.5, 133.0, 131.8, 129.8, 128.6, 128.1, 127.9, 125.8, 122.9, 121.5, 114.7, 69.8, 58.3, 54.4, 45.7, 43.8, 42.4, 27.5, 17.4. ESI-MS m/z: 523.6 $[M+H]^+$ HPLC $t_{ret}$=3.01 min.

Example 41

N-(2,5-Difluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

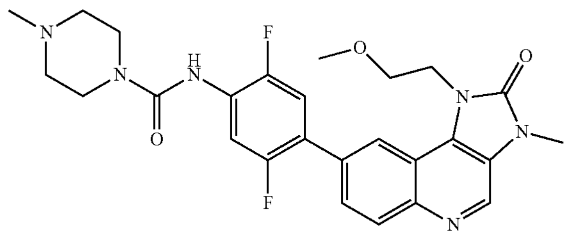

The preparation of this compound was carried out following the above described procedure for the synthesis of the compound of example 31, but with 37 mg (65) (0.11 mmol) as the aryl bromide starting material. Yield: 23 mg (41%) as a white solid. $^1$H NMR (400 MHz, DMSO) δ 8.91 (br s, 1H), 8.56 (s, 1H), 8.43 (s, 1H), 8.10 (d, J=8.8 Hz, 1H), 7.86-7.78 (m, 1H), 7.65-7.54 (m, 2H), 4.52 (t, J=5.1 Hz, 2H), 3.75 (t, J=5.1 Hz, 2H), 3.54 (s, 3H), 3.50-3.44 (m, 4H), 3.23 (s, 3H), 2.39-2.30 (m, 4H), 2.22 (s, 3H). ESI-MS m/z: 511.5 $[M+H]^+$ HPLC $t_{ret}$=2.81 min.

Example 42

N-(2,3-Difluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

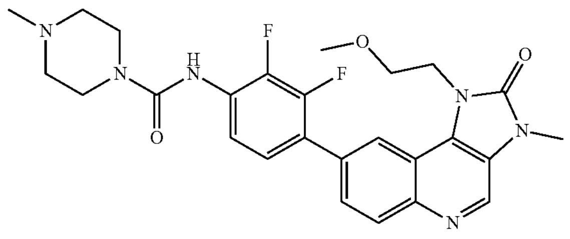

The preparation of this compound was carried out following the above described procedure for the synthesis of the compound of example 31, but with 37 mg (66) (0.11 mmol) as the aryl bromide starting material. Yield: 23 mg (41%) as a white solid. $^1$H NMR (400 MHz, DMSO) δ 8.93 (br s, 1H), 8.64 (s, 1H), 8.44 (s, 1H), 8.12 (d, J=8.8 Hz, 1H), 7.81 (d, J=8.8 Hz, 1H), 7.47-7.34 (m, 2H), 4.52 (t, J=5.2 Hz, 2H), 3.75 (t, J=5.2 Hz, 2H), 3.55 (s, 3H), 3.51-3.42 (m, 4H), 3.22 (s, 3H), 2.40-2.28 (m, 4H), 2.21 (s, 3H). ESI-MS m/z: 511.5 $[M+H]^+$ HPLC $t_{ret}$=2.70 min.

Example 43

N-(2,6-Difluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

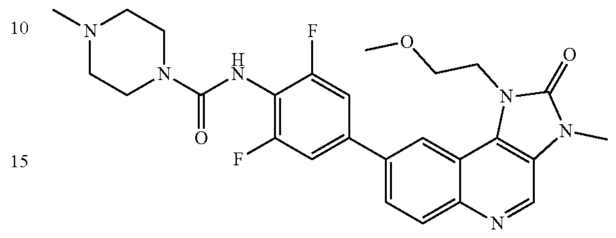

The preparation of this compound was carried out following the above described procedure for the synthesis of the compound of example 31, but with 37 mg (67) (0.11 mmol) as the aryl bromide starting material. Yield: 24 mg (42%) as a white solid. $^1$H NMR (400 MHz, DMSO) δ 8.90 (br s, 1H), 8.53 (s, 1H), 8.37 (s, 1H), 8.10 (d, J=8.9 Hz, 1H), 7.99 (d, J=8.9 Hz, 1H), 7.64 (d, J=8.6 Hz, 2H), 4.61 (t, J=5.3 Hz, 2H), 3.77 (t, J=5.3 Hz, 2H), 3.54 (s, 3H), 3.48 (s, 4H), 3.24 (s, 3H), 2.44-2.32 (m, 4H), 2.24 (s, 3H). ESI-MS m/z: 511.5 $[M+H]^+$ HPLC $t_{ret}$=2.23 min.

Example 44

N-(3,5-Difluoro-4-(1-(2-methoxyethyl)-3-methyl-2-oxo-2,3-dihydro-1H-imidazo[4,5-c]quinolin-8-yl)phenyl)-4-methylpiperazine-1-carboxamide

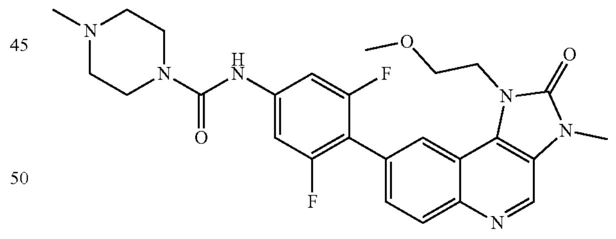

The preparation of this compound was carried out following the above described procedure for the synthesis of the compound of example 31, but with 37 mg (68) (0.11 mmol) as the aryl bromide starting material. Yield: 42 mg (75%) as a white solid. $^1$H NMR (400 MHz, DMSO) δ 9.00 (br s, 1H), 8.93 (s, 1H), 8.36-8.28 (m, 1H), 8.10 (d, J=8.8 Hz, 1H), 7.65 (dd, J=8.8, 1.0 Hz, 1H), 7.48-7.38 (m, 2H), 4.47 (t, J=5.6 Hz, 2H), 3.72 (t, J=5.6 Hz, 2H), 3.54 (s, 3H), 3.50-3.41 (m, 4H), 3.20 (s, 3H), 2.38-2.28 (m, 4H), 2.21 (s, 3H). ESI-MS m/z: 511.3 $[M+H]^+$ HPLC $t_{ret}$=3.56 min.

Example 45

N-(2-Fluoro-4-(1-(2-methoxyethyl)-3-methyl-2-oxo-2,3-dihydro-1H-imidazo[4,5-c]quinolin-8-yl)-5-methylphenyl)-4-methylpiperazine-1-carboxamide

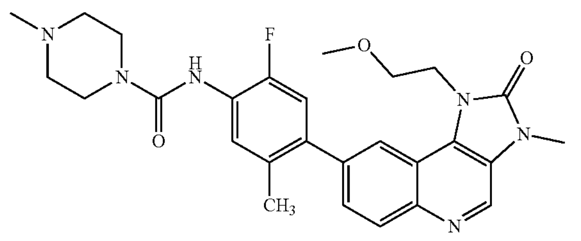

The preparation of this compound was carried out following the above described procedure for the synthesis of the compound of example 31, but with 36 mg (69) (0.11 mmol) as the aryl bromide starting material. Yield: 21 mg (38%) as a white solid. $^1$H NMR (400 MHz, DMSO) δ 8.91 (br s, 1H), 8.33 (s, 1H), 8.20 (s, 1H), 8.08 (d, J=8.7 Hz, 1H), 7.63 (d, J=8.7 Hz, 1H), 7.40 (d, J=8.0 Hz, 1H), 7.20 (d, J=11.3 Hz, 1H), 4.47 (t, J=5.1 Hz, 2H), 3.72 (t, J=5.1 Hz, 2H), 3.54 (s, 3H), 3.50-3.39 (m, 4H), 3.20 (s, 3H), 2.39-2.29 (m, 4H), 2.27 (s, 3H), 2.21 (s, 3H). ESI-MS m/z: 507.5 $[M+H]^+$ HPLC $t_{ret}$=2.44 min.

The following intermediates (70) to (108) were used for the preparation of the compounds of examples 46 to 57:

1-(4-Bromo-2,3-difluorophenyl)-3-(2-(dimethylamino)ethyl)urea (70)

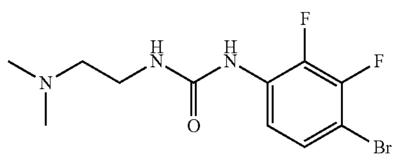 [SMILES: CN(C)CCNC(=O)Nc1ccc(Br)c(F)c1F]

To a solution of 242 mg phenyl chloroformate (1.54 mmol) in 8 ml THF was added dropwise a solution of 321 mg 4-bromo-2,3-difluoroaniline (1.54 mmol) in 4 ml THF at ambient temperature under vigorous stirring. Subsequently, 216 µl $Et_3N$ (1.54 mmol) were added to the reaction, resulting in the formation of a white precipitate. After about 30 min, TLC indicated complete conversion to the carbamate intermediate and 136 mg N,N-dimethylethylenediamine (1.54 mmol) were added in one portion. The reaction vial was placed in a heating block at 65° C. and stirring was continued until TLC indicated complete consumption of the phenyl carbamate. After cooling back to ambient temperature, the mixture was filtered over celite and the organic phase was washed with NaOH (2×), dried over $Na_2SO_4$ and evaporated. The residue was purified via flash chromatography (DCM/MeOH+2N $NH_3$ 3-10%) to obtain 293 mg (59%) of the title compound as white solid. $^1$H NMR (400 MHz, DMSO) δ 8.77 (s, 1H), 8.04-7.93 (m, 1H), 7.42-7.31 (m, 1H), 6.78-6.67 (m, 1H), 3.22-3.15 (m, 2H), 2.31 (t, J=5.8 Hz, 2H), 2.16 (s, 6H). $^{13}$C NMR (101 MHz, DMSO) δ 154.3, 146.98 (dd, J=242.8, 12.7 Hz), 140.31 (dd, J=246.3, 15.4 Hz), 130.20 (dd, J=7.8, 1.6 Hz), 127.14-126.99 (m), 115.89-115.73 (m), 99.01-98.79 (m), 58.3, 45.0, 37.0. ESI-MS m/z: 322.5 $[M+H]^+$ HPLC $t_{ret}$=4.06 min.

1-(4-Bromo-3-chloro-2-fluorophenyl)-3-(2-(dimethylamino)ethyl)urea (71)

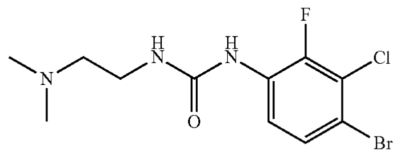 [SMILES: CN(C)CCNC(=O)Nc1ccc(Br)c(Cl)c1F]

To a solution of 235 mg phenyl chloroformate (1.5 mmol) in 2 ml THF was added a solution of 337 mg 4-bromo-3-chloro-2-fluoroaniline (1.5 mmol) in 2 ml THF at ambient temperature under vigorous stirring. Subsequently 211 µl $Et_3N$ (1.5 mmol) were added to the reaction, resulting in the formation of a white precipitate. After about 20 min, TLC indicated complete conversion to the carbamate intermediate. $Et_3N$ (1.5 mmol) and 132 mg N,N-dimethylethylenediamine (1.5 mmol) were added in one portion. The reaction vial was placed in a heating block at 65° C. and stirring was continued until TLC indicated complete consumption of the phenyl carbamate. After cooling back to ambient temperature, the mixture was diluted with DCM and the organic phase was successively washed with NaOH (3×). After drying and concentration under reduced pressure, crystallization of the yellow oil was induced by addition of small amounts of MeCN. The precipitate was homogenized by addition of minor amounts of MeCN combined with trituration. The solids were collected by filtration to yield 348 mg (69%) of the title compound as white solid. $^1$H NMR (400 MHz, DMSO) δ 8.72 (s, 1H), 8.21-8.05 (m, 1H), 7.46 (d, J=8.9 Hz, 1H), 6.83-6.68 (m, 1H), 3.22-3.13 (m, 2H), 2.31 (t, J=5.6 Hz, 2H), 2.16 (s, 6H). $^{13}$C NMR (101 MHz, DMSO) δ 154.4, 147.63 (d, J=246.3 Hz), 129.51 (d, J=10.6 Hz), 128.21 (d, J=3.7 Hz), 120.35 (d, J=17.5 Hz), 119.2, 112.2, 58.3, 45.0, 37.0. ESI-MS m/z: 338.5 $[M+H]^+$ HPLC $t_{ret}$=4.88 min.

1-(4-Bromo-3-chloro-2-fluorophenyl)-3-(2-(dimethylamino)ethyl)urea (72)

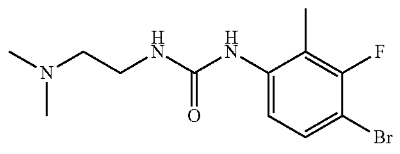 [SMILES: Cc1c(NC(=O)NCCN(C)C)ccc(Br)c1F]

This compound was prepared via the same procedure as described for (71) with 286 mg 4-bromo-3-fluoro-2-methylaniline (1.4 mmol) as starting material. Yield: 407 mg (91%) as white solid. $^1$H NMR (400 MHz, DMSO) δ 8.04 (s, 1H), 7.74 (dd, J=9.0, 0.9 Hz, 1H), 7.41-7.31 (m, 1H), 6.67 (t, J=5.1 Hz, 1H), 3.21-3.15 (m, 2H), 2.32 (t, J=6.1 Hz, 2H), 2.17 (s, 6H), 2.12 (d, J=2.3 Hz, 3H). $^{13}$C NMR (101 MHz, DMSO) δ 156.25 (d, J=239.4 Hz), 154.9, 139.78 (d, J=5.9 Hz), 129.47 (d, J=1.5 Hz), 117.04 (d, J=3.0 Hz), 115.33 (d, J=19.4 Hz), 99.32 (d, J=22.6 Hz), 58.5, 45.0, 37.0, 9.72 (d, J=5.3 Hz). ESI-MS m/z: 318.5 $[M+H]^+$ HPLC $t_{ret}$=4.09 min.

Example 46

1-(2,3-Difluoro-4-(1-(2-methoxyethyl)-3-methyl-2-oxo-2,3-dihydro-1H-imidazo[4,5-c]quinolin-8-yl)phenyl)-3-(2-(dimethylamino)ethyl)urea

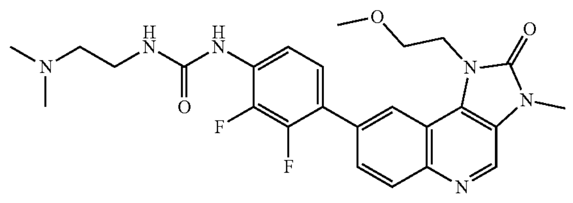

In a screw-top reaction vial were combined 38 mg (32) (0.1 mmol) and 32 mg (70) (0.1 mmol) under argon atmosphere. Subsequently, 2.4 ml degassed dioxane and 0.6 ml of an 0.5 M aqueous $K_3PO_4$ solution were added via syringe. The mixture was degassed by three vacuum/argon cycles before 1 mg $tBu_3P$ Pd G3 (1.5 mol %) was added as stock solution in dioxane and the degassing procedure was repeated. The reaction vial was sealed and stirring was continued at 70° C. heating-block temperature for ca. one hour. TLC indicated complete conversion at this point and the reaction mixture was diluted with EtOAc. The organic phase was washed with brine, dried over $Na_2SO_4$ and concentrated under reduced pressure. The residue purified via flash chromatography (DCM/MeOH+2N $NH_3$ 2-8%) to obtain 40 mg (80%) of the title compound as white solid. $^1H$ NMR (400 MHz, DMSO) δ 8.90 (s, 1H), 8.82 (br s, 1H), 8.45-8.37 (m, 1H), 8.16-8.06 (m, 2H), 7.79 (dt, J=8.9, 1.9 Hz, 1H), 7.46-7.36 (m, 1H), 6.76 (t, J=5.1 Hz, 1H), 4.51 (t, J=5.5 Hz, 2H), 3.75 (t, J=5.5 Hz, 2H), 3.54 (s, 3H), 3.27-3.16 (m, 5H), 2.35 (t, J=6.1 Hz, 2H), 2.19 (s, 6H). ESI-MS m/z: 499.6 $[M+H]^+$ HPLC $t_{ret}$=2.12 min.

Example 47

1-(3-Chloro-2-fluoro-4-(1-(2-methoxyethyl)-3-methyl-2-oxo-2,3-dihydro-1H-imidazo[4,5-c]quinolin-8-yl)phenyl)-3-(2-(dimethylamino)ethyl)urea

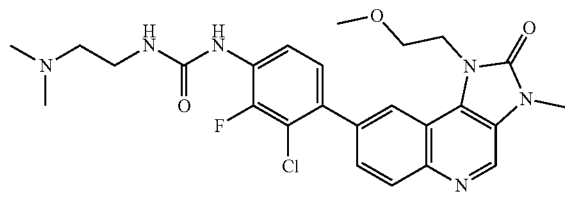

The same protocol was applied as described above for the preparation of Example 46 using 58 mg (32) (0.15 mmol) and 51 mg (71) (0.15 mmol) as starting materials. Flash chromatography with gradient elution (DCM/MeOH+2N $NH_3$ 2-8.5%) Yield: 62 mg (80%) as white solid. $^1H$ NMR (400 MHz, DMSO) δ 8.92 (s, 1H), 8.77 (s, 1H), 8.31 (d, J=1.7 Hz, 1H), 8.28-8.22 (m, 1H), 8.12-8.06 (m, 1H), 7.69 (dd, =8.8, 1.8 Hz, 1H), 7.31 (dd, J=8.7, 1.6 Hz, 1H), 6.77 (t, J=5.2 Hz, 1H), 4.47 (t, J=5.6 Hz, 2H), 3.73 (t, J=5.6 Hz, 2H), 3.54 (s, 3H), 3.25-3.19 (m, 5H), 2.35 (t, J=6.1 Hz, 2H), 2.19 (s, 6H). ESI-MS m/z: 515.6 $[M+H]^+$ HPLC $t_{ret}$=2.300 min.

Example 48

1-(2-(Dimethylamino)ethyl)-3-(3-fluoro-4-(1-(2-methoxyethyl)-3-methyl-2-oxo-2,3-dihydro-1H-imidazo[4,5-c]quinolin-8-yl)-2-methylphenyl)urea

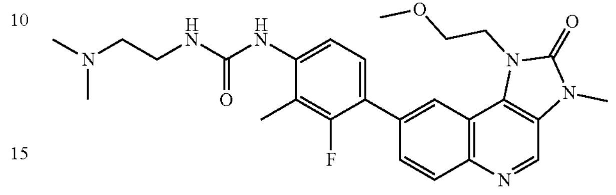

The same protocol was applied as described above for the preparation of Example 46 using 58 mg (32) (0.15 mmol) and 48 mg (72) (0.15 mmol) as starting materials. Flash chromatography with gradient elution (first normal phase: DCM/MeOH+2N $NH_3$ 3-10%; then reversed phase (LiChroprep RP-C18 40-63 μm): water+0.05M $Et_3N$/MeOH 15-100%). Yield: 59 mg (80%) as white solid. $^1H$ NMR (400 MHz, DMSO) δ 8.88 (s, 1H), 8.38-8.33 (m, 1H), 8.16-8.10 (m, 1H), 8.10-8.05 (m, 1H), 7.94-7.87 (m, 1H), 7.80-7.73 (m, 1H), 7.45-7.36 (m, 1H), 6.72 (t, J=5.1 Hz, 1H), 4.48 (t, J=5.6 Hz, 2H), 3.75 (t, J=5.7 Hz, 2H), 3.53 (s, 3H), 3.25-3.19 (m, 5H), 2.35 (t, J=6.1 Hz, 2H), 2.23-2.16 (m, 9H). 495.6 $[M+H]^+$ HPLC $t_{ret}$=1.870 min.

((4-Bromophenyl)carbamoyl)glycine (73)

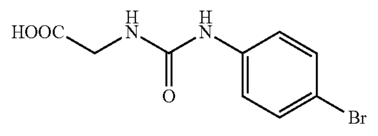 [SMILES: O=C(O)CNC(=O)Nc1ccc(Br)cc1]

To a solution of 2.19 g 4-bromophenylisocyanate (11.1 mmol) in 20 ml dry DMF were added 2.05 ml $Et_3N$ (14.6 mmol) and 1.70 g glycine ethylester hydrochloride (12.2 mmol) at ambient temperature. The mixture was stirred for 2 hours and was then diluted with 2N HCl under ice cooling. The precipitate was filtered off and washed with water. The wet intermediate was suspended in a mixture of EtOH/THF (15 ml each) and 15 ml of an 1N aqueous LiOH was added. The mixture was stirred at 60° C. oil bath temperature until TLC indicated complete conversion. The reaction mixture was diluted with MTBE and the organic phase was extracted two times with 1N NaOH (2×150 ml). The combined aqueous phases were backwashed with MTBE and then filtered through a bed of celite to remove insoluble impurities. The filtrate was cooled in an ice/water bath and acidified with conc. HCl to precipitate the product. The solids were filtered off, washed with water and dried in a convection oven at 60° C. to obtain 2.34 g (78%) of the title compound as white solid. $^1H$ NMR (400 MHz, DMSO) δ 12.55 (br s, 1H), 8.90 (br s, 1H), 7.48-7.30 (m, 4H), 6.40 (t, J=5.5 Hz, 1H), 3.79 (d, J=5.5 Hz, 2H). $^{13}C$ NMR (101 MHz, DMSO) δ 172.0, 155.0, 139.7, 131.4, 119.6, 112.5, 41.3. HPLC $t_{ret}$=5.69 min.

1-(2-(Azetidin-1-yl)-2-oxoethyl)-3-(4-bromophenyl) urea (74)

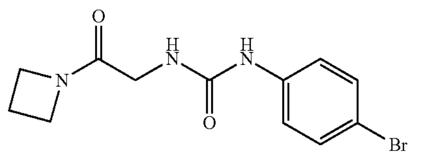 [SMILES: O=C(NCC(=O)N1CCC1)Nc1ccc(Br)cc1]

To a suspension of 483 mg (73) (1.77 mmol) and 199 mg azetidine hydrochloride (2.12 mmol) in 15 ml DMF was successively added 0.62 ml $Et_3N$ (4.42 mmol), 344 mg HOBt (20% wet, 2.03 mmol) and 390 mg EDC HCl (2.03 mmol) at ambient temperature. After overnight stirring, TLC indicated complete conversion and the reaction was quenched with water and transferred to a separatory funnel. An extractive workup with DCM and EtOAc seemed ineffective due to the low solubility of the product, but the majority of side products were extracted to the organic phase. The white precipitate remaining in the aqueous phase was isolated by filtration, washed with 2N HCl and water and dried in a convection oven at 60° C. This material proved to be of sufficient purity and was used without further purification in the next step. Yield: 389 mg (71%) as white solid. $^1H$ NMR (400 MHz, DMSO) δ 9.02 (br s, 1H), 7.42-7.32 (m, 4H), 6.35 (t, J=5.0 Hz, 1H), 4.15 (t, J=7.6 Hz, 2H), 3.89 (t, J=7.6 Hz, 2H), 3.70 (d, J=5.0 Hz, 2H), 2.30-2.16 (m, 2H). $^{13}C$ NMR (101 MHz, DMSO) δ 168.6, 154.8, 139.8, 131.4, 119.4, 112.3, 49.3, 47.8, 39.4, 15.3. ESI-MS m/z: 334.5 $[M+Na]^+$ HPLC $t_{ret}$=5.51 min.

1-(4-Bromophenyl)-3-(2-(3-fluoroazetidin-1-yl)-2-oxoethyl)urea (75)

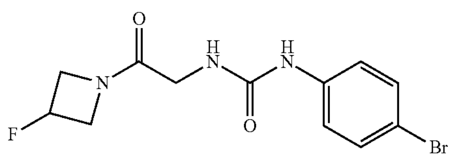 [SMILES: O=C(NCC(=O)N1CC(F)C1)Nc1ccc(Br)cc1]

To a suspension of 466 mg (73) (1.71 mmol) and 238 mg 3-fluoroazetidine hydrochloride (2.13 mmol) in 12 ml DMF was successively added 0.60 ml $Et_3N$ (4.27 mmol), 331 mg HOBt (20% wet, 1.96 mmol) and 376 mg EDC HCl (1.96 mmol) at ambient temperature. After overnight stirring, the mixture was diluted with EtOAc and transferred to a separatory funnel. The organic phase was washed with 2N HCl, 1M NaOH and brine prior to drying over $Na_2SO_4$ and evaporation. The crude product was triturated with cold acetonitrile, filtered off and dried in vacuo to give 257 mg (46%) of the title compound as a white solid with sufficient purity. $^1H$ NMR (400 MHz, DMSO) δ 8.95 (br s, 1H), 7.47-7.26 (m, 4H), 6.35 (t, J=5.1 Hz, 1H), 5.55-5.26 (m, 1H), 4.57-4.41 (m, 1H), 4.36-4.10 (m, 2H), 4.02-3.85 (m, 1H), 3.76 (d, J=5.1 Hz, 2H). $^{13}C$ NMR (101 MHz, DMSO) δ 169.3, 169.3, 154.8, 139.7, 131.4, 119.4, 112.4, 82.9 (d, J=200.7 Hz), 57.2 (d, J=25.6 Hz), 55.8 (d, J=25.5 Hz). ESI-MS m/z: 352.4 $[M+Na]^+$ HPLC $t_{ret}$=6.11 min.

1-(4-Bromophenyl)-3-(2-(3,3-difluoroazetidin-1-yl)-2-oxoethyl)urea (76)

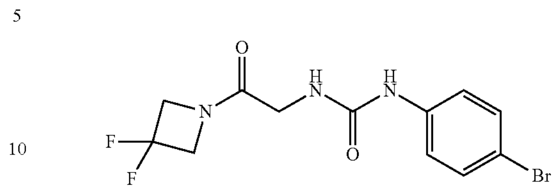

To a suspension of 447 mg (73) (1.64 mmol) and 265 mg 3,3-difluoroazetidine hydrochloride (2.05 mmol) in 10 ml DMF was successively added 0.58 ml $Et_3N$ (4.09 mmol), 318 mg HOBt (20% wet, 1.88 mmol) and 361 mg EDC HCl (1.88 mmol) at ambient temperature. After overnight stirring, the mixture was diluted with EtOAc and transferred to a separatory funnel. The organic phase was washed with 2N HCl, 1M NaOH and brine prior to drying over $Na_2SO_4$ and evaporation. The crude product was triturated with cold acetonitrile, filtered off and dried in vacuo to give 484 mg (85%) of the title compound as a white solid with sufficient purity. $^1H$ NMR (400 MHz, DMSO) δ 8.94 (s, 1H), 7.42-7.31 (m, 4H), 6.39 (t, J=5.1 Hz, 1H), 4.66 (t, J=12.4 Hz, 2H), 4.33 (t, J=12.4 Hz, 2H), 3.83 (d, J=5.1 Hz, 2H). $^{13}C$ NMR (101 MHz, DMSO) δ 169.8, 154.8, 139.7, 131.4, 119.5, 116.3 (t, J=272.5 Hz), 112.5, 60.9 (t, J=27.6 Hz), 59.8 (t, J=27.6 Hz), 40.2. ESI-MS m/z: 346.5 $[M-]^-$ HPLC $t_{ret}$=6.74 min.

1-(2-(Azetidin-1-yl)ethyl)-3-(4-bromophenyl)urea (77)

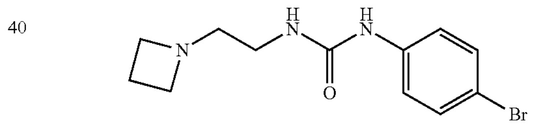

To an ice-cooled suspension of 283 mg (74) (0.91 mmol) and 123 mg $NaBH_4$ (3.26 mmol) in 15 ml THF were added 414 mg iodine (1.63 mmol) as solution in 5 ml THF in several portions and in a rate that maintained fast discoloration of the reaction mixture. After complete addition, stirring was continued until TLC indicated complete consumption of starting materials and formation of the desired product (confirmed via TLC-MS). The excess borane was quenched by the careful addition of MeOH (foaming) and the mixture was then diluted with EtOAc and transferred to a separatory funnel. The organic phase was washed with 1N NaOH and brine and was then dried over $Na_2SO_4$ and evaporated to dryness. The residue was purified via flash chromatography (DCM/MeOH+2N $NH_3$ 2-8%) and the title compound was obtained as 111 mg (41%) of a white solid after trituration with pentane. $^1H$ NMR (400 MHz, $CDCl_3$) 7.34 (d, J=8.4 Hz, 2H), 7.23 (d, J=8.4 Hz, 2H), 6.09 (t, J=4.9 Hz, 1H), 3.28 (t, J=6.9 Hz, 4H), 3.22-3.08 (m, 2H), 2.68-2.56 (m, 2H), 2.20-2.02 (m, 2H). $^{13}C$ NMR (101 MHz, $CDCl_3$) δ 157.1, 139.1, 132.0, 121.2, 115.1, 60.4, 55.3, 39.0, 17.8. ESI-MS m/z: 298.3 $[M+H]^+$ HPLC $t_{ret}$=3.39 min.

1-(4-Bromophenyl)-3-(2-(3-fluoroazetidin-1-yl)ethyl)urea (78)

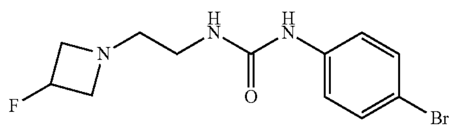 [SMILES: O=C(NCCN1CC(F)C1)Nc1ccc(Br)cc1]

To an ice-cooled suspension of 240 mg (75) (0.73 mmol) and 99 mg $NaBH_4$ (2.62 mmol) in 10 ml THF were added 332 mg iodine (1.31 mmol) as solution in 5 ml THF in several portions and in a rate that maintained fast discoloration of the reaction mixture. After complete addition, stirring was continued until TLC indicated complete consumption of starting materials and formation of the desired product (confirmed via TLC-MS). The excess borane was quenched by the careful addition of MeOH (foaming) and the mixture was then diluted with EtOAc and transferred to a separatory funnel. The organic phase was washed with 1N NaOH and brine and was then dried over $Na_2SO_4$ and evaporated to dryness. The residue was purified via flash chromatography (DCM/MeOH+2N $NH_3$ 2-8%) and the title compound was obtained as 90 mg (41%) of a white solid after trituration with pentane. $^1H$ NMR (400 MHz, DMSO) δ 8.71 (br s, 1H), 7.43-7.27 (m, 4H), 6.12 (t, J=4.8 Hz, 1H), 5.28-5.03 (m, 1H), 3.65-3.49 (m, 2H), 3.20-2.97 (m, 4H), 2.57-2.46 (m, 2H). $^{13}C$ NMR (101 MHz, DMSO) δ 154.8, 139.9, 131.2, 119.4, 112.1, 82.8 (d, J=201.8 Hz), 60.9 (d, J=20.2 Hz). 58.5, 37.3. ESI-MS m/z: 316.5 $[M+H]^+$ HPLC $t_{ret}$=3.47 min.

1-(4-Bromophenyl)-3-(2-(3,3-difluoroazetidin-1-yl)ethyl)urea (79)

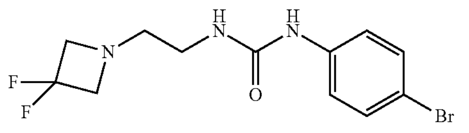 [SMILES: O=C(NCCN1CC(F)(F)C1)Nc1ccc(Br)cc1]

To an ice-cooled suspension of 253 mg (76) (0.73 mmol) and 99 mg $NaBH_4$ (2.62 mmol) in 15 ml THF were added 332 mg iodine (1.31 mmol) as solution in 5 ml THF in several portions and in a rate that maintained fast discoloration of the reaction mixture. After complete addition, stirring was continued until TLC indicated complete consumption of starting material. The excess borane was quenched by the careful addition of MeOH (foaming) and the mixture was heated to 60° C. oil-bath temperature. After about two hours TLC indicated major conversion to the desired product and the reaction was diluted with EtOAc and the organic phase was washed with 1N NaOH and brine, was then dried over $Na_2SO_4$ and evaporated to dryness. The residue was purified via flash chromatography (DCM/MeOH 2-8%) and the title compound was obtained as 150 mg (62%) as a white solid after trituration with pentane. $^1H$ NMR (400 MHz, DMSO) δ 8.72 (s, 1H), 7.42-7.30 (m, 4H), 6.16 (t, J=5.6 Hz, 1H), 3.59 (t, J=12.5 Hz, 4H), 3.13-3.04 (m, 2H), 2.61 (t, J=5.9 Hz, 2H). $^{13}C$ NMR (101 MHz, DMSO) δ 155.4, 140.4, 131.8, 119.9, 117.8 (t, J=275.1 Hz), 112.7, 64.4 (t, J=21.9 Hz), 58.3, 38.1. ESI-MS m/z: 334.4 $[M+H]^+$ HPLC $t_{ret}$=3.93 min.

((4-Bromophenyl)carbamoyl)-DL-alanine (80)

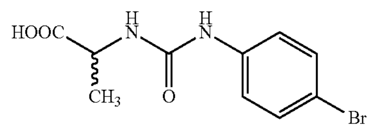 [SMILES: CC(NC(=O)Nc1ccc(Br)cc1)C(=O)O]

To a solution of 936 mg 4-bromophenylisocyanate (4.7 mmol) in 6 ml dry DMF were added 877 μl $Et_3N$ (6.2 mmol) and 726 mg DL-alaninemethylester hydrochloride (5.2 mmol) at ambient temperature. The mixture was stirred for 2 hours and was then diluted with 2N HCl under ice cooling. The precipitate was filtered off and washed with water. The wet intermediate was suspended in EtOH/THF (5 ml each) and 5 ml of an 1N aqueous LiOH were added and the mixture was stirred at 60° C. oil bath temperature until TLC indicated complete conversion. The reaction was cooled in an ice/water bath and water was added to induce precipitation of the product. The suspension was acidified with 2N HCl and the white precipitate was isolated by filtration. The filter cake was dried in a convection oven at 60° C. to yield 1120 mg (83%) of the title compound as white solid. $^1H$ NMR (400 MHz, DMSO) δ 12.65 (br s, 1H), 8.74 (s, 1H), 7.46-7.29 (m, 4H), 6.48 (d, J=5.7 Hz, 1H), 4.25-4.09 (m, 1H), 1.39-1.17 (m, 3H). $^{13}C$ NMR (101 MHz, DMSO) δ 174.7, 154.4, 139.6, 131.4, 119.5, 112.5, 48.0, 18.2. ESI-MS m/z: 285.2 $[M-]^-$ HPLC $t_{ret}$=6.44 min.

(RS)-2-(3-(4-Bromophenyl)ureido)-N,N-dimethylpropanamide (81)

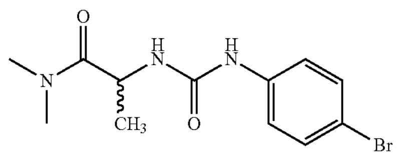 [SMILES: CC(NC(=O)Nc1ccc(Br)cc1)C(=O)N(C)C]

To a solution of 500 mg (80) (1.74 mmol) and 316 mg dimethylamine hydrochloride (2.44 mmol) in 8 ml DMF were successively added 612 μl $Et_3N$ (4.35 mmol), 338 mg HOBt (20% wet, 2.0 mmol) and 384 mg EDC HCl (2.0 mmol) at ambient temperature and the resulting suspension was stirred overnight. The reaction was then diluted with EtOAc and transferred to a separatory funnel. The organic phase was washed with water, 2N HCl (2×), 1N NaOH and brine, prior to drying over $Na_2SO_4$ and evaporation. The residue was purified via flash chromatography (DCM/MeOH 1-5%) to yield 445 mg (81%) of the title compound as white solid. $^1H$ NMR (400 MHz, DMSO) δ 8.84 (s, 1H), 7.43-7.28 (m, 4H), 6.49 (d, J=7.8 Hz, 1H), 4.74-4.59 (m, 1H), 3.04 (s, 3H), 2.85 (s, 3H), 1.19 (d, J=6.8 Hz, 3H). $^{13}C$ NMR (101 MHz, DMSO) δ 172.3, 154.1, 139.7, 131.3, 119.3, 112.3, 44.8, 36.4, 35.1, 18.6.

ESI-MS m/z: 336.4 $[M+Na]^+$ HPLC $t_{ret}$=6.28 min.

(RS)-1-(4-Bromophenyl)-3-(1-(dimethylamino)propan-2-yl)urea (82)

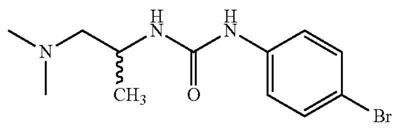 [SMILES: CC(CN(C)C)NC(=O)Nc1ccc(Br)cc1]

To an ice-cooled suspension of 250 mg (81) (0.80 mmol) and 108 mg $NaBH_4$ (2.86 mmol) in 10 ml THF were added 364 mg iodine (1.31 mmol) as solution in 5 ml THF in several portions and in a rate that maintained fast discoloration of the reaction mixture. After complete addition, stirring was continued until TLC indicated complete consumption of starting materials and formation of the desired product (confirmed via TLC-MS). The excess borane was quenched by the careful addition of MeOH (foaming) and the mixture was then diluted with EtOAc and transferred to a separatory funnel. The organic phase was washed with 1N NaOH and brine and was then dried over $Na_2SO_4$ and evaporated to dryness. The residue was purified via flash chromatography (DCM/MeOH+2N $NH_3$ 2-8%) and the title compound was obtained as 130 mg (54%) of a white solid after trituration with pentane. $^1H$ NMR (400 MHz, $CDCl_3$) δ 9.47 (br s, 1H), 7.33 (d, J=8.7 Hz, 2H), 7.21 (d, J=8.7 Hz, 2H), 5.20 (br s, 1H), 3.87-3.67 (m, 1H), 2.48 (dd, J=12.8, 9.4 Hz, 1H), 2.31 (s, 6H), 2.25 (dd, J=12.8, 2.8 Hz, 2H), 1.16 (d, J=6.6 Hz, 3H). $^{13}C$ NMR (101 MHz, $CDCl_3$) δ 156.9, 139.2, 132.0, 121.0, 114.9, 67.2, 45.8, 45.7, 20.3. ESI-MS m/z: 300.5 $[M+H]^+$ HPLC $t_{ret}$=3.63 min.

Example 49

1-(2-(Azetidin-1-yl)ethyl)-3-(4-(1-(2-methoxyethyl)-3-methyl-2-oxo-2,3-dihydro-1H-imidazo[4,5-c]quinolin-8-yl)phenyl)urea

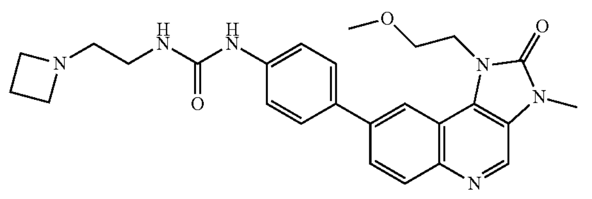 [SMILES: COCCn1c(=O)n(C)c2cnc3ccc(-c4ccc(NC(=O)NCCN5CCC5)cc4)cc3c21]

The same protocol was applied as described above for the preparation of Example 47 using 38 mg (32) (0.1 mmol) and 30 mg (77) (0.1 mmol) as starting materials. Flash chromatography with gradient elution (DCM/MeOH+2N $NH_3$ 4-10%). Yield: 31 mg (65%) as white solid. $^1H$ NMR (400 MHz, DMSO) δ 8.84 (s, 1H), 8.79 (br s, 1H), 8.40 (s, 1H), 8.06 (d, J=8.9 Hz, 1H), 7.91 (dd, J=8.9, 1.0 Hz, 1H), 7.72 (d, J=8.5 Hz, 2H), 7.54 (d, J=8.5 Hz, 2H), 6.15 (t, J=5.0 Hz, 1H), 4.55 (t, J=5.4 Hz, 2H), 3.77 (t, J=5.4 Hz, 2H), 3.53 (s, 3H), 3.24 (s, 3H), 3.15 (t, J=6.8 Hz, 4H), 3.09-3.01 (m, 2H), 2.44 (t, J=5.9 Hz, 2H), 1.98 (p, J=6.8 Hz, 2H). $^{13}C$ NMR (101 MHz, DMSO) δ 155.0, 153.4, 143.5, 140.5, 137.4, 132.7, 132.0, 130.6, 128.5, 127.2, 125.4, 122.8, 117.9, 117.2, 115.3, 70.0, 58.6, 58.3, 54.4, 42.5, 37.1, 27.4, 17.2. ESI-MS m/z: 475.7 $[M+H]^+$ HPLC $t_{ret}$=1.41 min.

Example 50

1-(2-(3-Fluoroazetidin-1-yl)ethyl)-3-(4-(1-(2-methoxyethyl)-3-methyl-2-oxo-2,3-dihydro-1H-imidazo[4,5-c]quinolin-8-yl)phenyl)urea

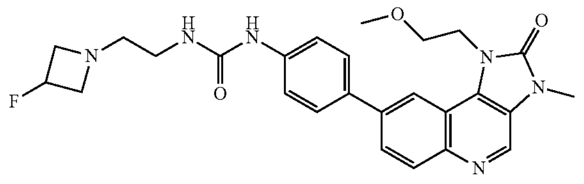 [SMILES: COCCn1c(=O)n(C)c2cnc3ccc(-c4ccc(NC(=O)NCCN5CC(F)C5)cc4)cc3c21]

The same protocol was applied as described above for the preparation of Example 46 using 38 mg (32) (0.1 mmol) and 32 mg (78) (0.1 mmol) as starting materials. Flash chromatography with gradient elution (DCM/MeOH+2N $NH_3$ 1-7%). Yield: 41 mg (83%) as white solid. $^1H$ NMR (400 MHz, DMSO/MeOD) δ 8.82 (s, 1H), 8.41 (d, J=1.7 Hz, 1H), 8.05 (d, J=8.9 Hz, 1H), 7.90 (dd, J=8.9, 1.7 Hz, 1H), 7.70 (d, J=8.7 Hz, 2H), 7.54 (d, J=8.7 Hz, 2H), 5.27-5.04 (m, 1H), 4.55 (t, J=5.6 Hz, 2H), 3.77 (t, J=5.6 Hz, 2H), 3.65-3.54 (m, 2H), 3.52 (s, 3H), 3.24 (s, 3H), 3.20-3.11 (m, 2H), 3.10 (t, J=6.1 Hz, 2H), 2.55 (t, J=6.1 Hz, 2H). $^{13}C$ NMR (101 MHz, DMSO/MeOD) δ 155.2, 153.7, 143.7, 140.6, 137.7, 132.9, 132.3, 130.7, 128.8, 127.5, 125.7, 123.1, 118.1, 117.5, 115.6, 83.0 (d, J=201.9 Hz), 70.3, 61.2 (d, J=20.2 Hz), 58.8, 58.5, 42.8, 37.4, 27.5. ESI-MS m/z: 493.8 $[M+H]^+$ HPLC $t_{ret}$=1.42 min.

Example 51

1-(2-(3,3-Difluoroazetidin-1-yl)ethyl)-3-(4-(1-(2-methoxyethyl)-3-methyl-2-oxo-2,3-dihydro-1H-imidazo[4,5-c]quinolin-8-yl)phenyl)urea

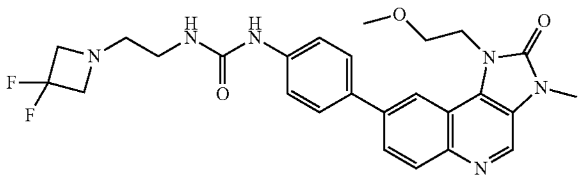 [SMILES: COCCn1c(=O)n(C)c2cnc3ccc(-c4ccc(NC(=O)NCCN5CC(F)(F)C5)cc4)cc3c21]

The same protocol was applied as described above for the preparation of Example 46 using 38 mg (32) (0.1 mmol) and 33 mg (79) (0.1 mmol) as starting materials. Flash chromatography with gradient elution (DCM/MeOH 2-10%). Yield: 38 mg (74%) as white solid. $^1H$ NMR (400 MHz, DMSO) δ 8.85 (s, 1H), 8.76 (s, 1H), 8.41 (d, J=1.4 Hz, 1H), 8.06 (d, J=8.9 Hz, 1H), 7.91 (dd, J=8.9, 1.4 Hz, 1H), 7.72 (d, J=8.6 Hz, 2H), 7.55 (d, J=8.6 Hz, 2H), 6.20 (t, J=5.4 Hz, 1H), 4.56 (t, J=5.4 Hz, 2H), 3.78 (t, J=5.4 Hz, 2H), 3.64 (t, J=12.5 Hz, 4H), 3.53 (s, 3H), 3.24 (s, 3H), 3.18-3.08 (m, 2H), 2.65 (t, J=5.6 Hz, 2H). $^{13}C$ NMR (101 MHz, DMSO) δ 155.0, 153.5, 143.4, 140.5, 137.4, 132.8, 132.0, 130.6, 128.5, 127.3, 125.5, 122.9, 118.0, 117.3, 117.4 (t, J=275.0 Hz), 115.3, 70.1, 63.9 (t, J=22.0 Hz), 58.4, 57.8, 42.6, 37.6, 27.5. ESI-MS m/z: 545.7 $[M+Cl]^-$ HPLC $t_{ret}$=1.51 min.

Example 52

(RS)-1-(1-(Dimethylamino)propan-2-yl)-3-(4-(1-(2-methoxyethyl)-3-methyl-2-oxo-2,3-dihydro-1H-imidazo[4,5-c]quinolin-8-yl)phenyl)urea

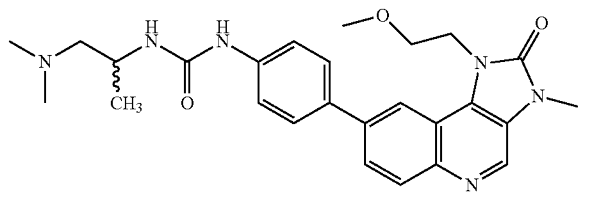

The same protocol was applied as described above for the preparation of Example 46 using 38 mg (32) (0.1 mmol) and 30 mg (82) (0.1 mmol) as starting materials. Flash chromatography with gradient elution (DCM/MeOH+2N $NH_3$ 2-8%). Yield: 35 mg (73%) as white solid. $^1H$ NMR (400 MHz, DMSO) δ 8.84 (s, 1H), 8.69 (br s, 1H), 8.41 (d, J=1.7 Hz, 1H), 8.06 (d, J=8.9 Hz, 1H), 7.91 (dd, J=8.9, 1.7 Hz, 1H), 7.72 (d, J=8.7 Hz, 2H), 7.55 (d, J=8.7 Hz, 2H), 6.03 (d, J=6.8 Hz, 1H), 4.55 (t, J=5.4 Hz, 2H), 3.77 (t, J=5.4 Hz, 2H), 3.81-3.72 (m, 1H), 3.53 (s, 3H), 3.24 (s, 3H), 2.30 (dd, J=12.1, 8.2 Hz, 1H), 2.18 (s, 6H), 2.14 (dd, J=12.1, 6.3 Hz, 1H), 1.11 (d, J=6.3 Hz, 3H). $^{13}C$ NMR (101 MHz, DMSO) δ 154.8, 153.5, 143.5, 140.6, 137.4, 132.8, 131.9, 130.6, 128.5, 127.3, 125.4, 122.9, 117.9, 117.2, 115.4, 70.1, 64.7, 58.4, 45.4, 43.2, 42.5, 27.4, 19.7. ESI-MS m/z: 477.7 $[M+H]^+$ HPLC $t_{ret}$=1.55 min.

Di-tert-butyl (RS)-2-(hydroxymethyl)piperazine-1,4-dicarboxylate (83)

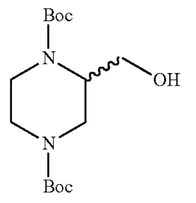 [SMILES: CC(C)(C)OC(=O)N1CCN(C(=O)OC(C)(C)C)C(CO)C1]

To a solution of 988 mg tert-butyl (RS)-3-(hydroxymethyl)piperazine-1-carboxylate (4.57 mmol) in 50 ml THF were added 1007 mg $Boc_2O$ (4.61 mmol) at ambient temperature. The mixture was stirred until gas evolution ceased and TLC (ninhydrin stain) indicated complete conversion after about 3 hours. The reaction was diluted with EtOAc and transferred to a separatory funnel. The organic phase was washed with 2N HCl and brine, prior to drying over $Na_2SO_4$ and evaporation of the solvents. The title compound was yielded as colorless oil, which solidifies to a white solid during drying under high vac overnight. $^1H$ NMR (400 MHz, $CDCl_3$) δ 4.28-3.74 (m, 4H), 3.70-3.44 (m, 2H), 3.12-2.18 (m, 4H), 1.45 (s, 9H), 1.44 (s, 9H).

Di-tert-butyl (RS)-2-(((4-bromophenyl)amino)methyl)piperazine-1,4-dicarboxylate (84)

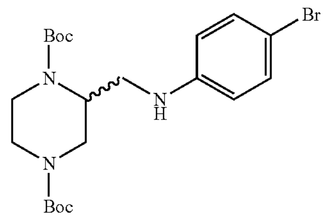 [SMILES: CC(C)(C)OC(=O)N1CCN(C(=O)OC(C)(C)C)C(CNc2ccc(Br)cc2)C1]

A schlenk flask containing a solution of 493 μl oxalyl chloride (5.8 mmol) in 30 ml dry DCM was cooled to −78° C. using acetone/liquid nitrogen. Under argon atmosphere were added 440 μl DMSO (6.2 mmol) as solution in 4 ml DCM dropwise with vigorous stirring. Stirring was continued for about 15 min before a solution of 1.40 g (83) (4.4 mmol) in 10 ml DCM was added slowly to the reaction mixture. After another 30 min of stirring, 1.87 ml $Et_3N$ (13.3 mmol) were added as solution in 4 ml DCM dropwise and stirring was continued for about two hours. The reaction was quenched by the addition of 5 ml water and the mixture was allowed to reach ambient temperature. After dilution with DCM, the organic phase was successively washed with water (3×), sat. $NaHCO_3$ and brine. The organic phase was dried over $Na_2SO_4$ and concentrated under reduced pressure, yielding the aldehyde intermediate as oily crystalline solid, which was directly used without further purification.

The crude aldehyde was taken up in 30 ml dry DCM and 300 μl acetic acid along with 761 mg 4-bromoaniline (4.4 mmol) were added subsequently at ambient temperature. After 30 min, 2.34 g sodium triacetoxy borohydride (11.1 mmol) were added and stirring was continued at ambient temperature. After about two hours, TLC indicated complete conversion and the reaction was quenched by the addition of water. The mixture was extracted twice with DCM and the combined extracts were backwashed with sat. $NaHCO_3$ and brine. After drying over $Na_2SO_4$ and evaporation of the solvents, an oily brownish residue was obtained.

This was subjected to flash purification (hexane/EtOAc+5% MeOH 5-25%) to yield 1.55 g (75%) of the title compound as slightly yellow sticky residue, which still contained some inpurities, but was carried on directly to the next step. ESI-MS m/z: 492.5 $[M+Na]^+$ HPLC $t_{ret}$=10.85 min.

Di-tert-butyl (RS)-2-(((4-bromophenyl)((4-nitrophenoxy)carbonyl)amino)methyl)piperazine-1,4-dicarboxylate (85)

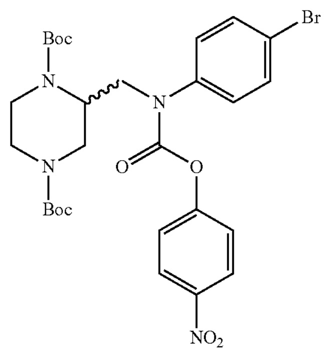 [SMILES: CC(C)(C)OC(=O)N1CCN(C(=O)OC(C)(C)C)C(CN(C(=O)Oc2ccc([N+](=O)[O-])cc2)c2ccc(Br)cc2)C1]

To a solution of 1.53 g crude (84) (3.25 mmol) in 10 ml DCM were added 289 μl pyridine (3.58 mmol) and the solution was cooled in an ice/water bath. Subsequently was added a solution of 721 mg p-nitrophenylchloroformate (3.58 mmol) as a solution in 2 ml DCM. The mixture was stirred until TLC indicated complete conversion and then the reaction was quenched by pouring it on 2N HCl followed by extraction with DCM (2×20 ml). The combined extracts were washed with sat. $NaHCO_3$ and brine, prior to drying and evaporation. The residue was purified via flash chromatography (hexane/EtOAc 10-40%) to yield 862 mg (42%) of the title compound as an off-white foam. ESI-MS m/z: 657.9 $[M+Na]^+$ HPLC $t_{ret}$=11.13 min.

tert-Butyl (RS)-2-(4-bromophenyl)-3-oxohexahydroimidazo[1,5-a]pyrazine-7(1H)-carboxylate (86)

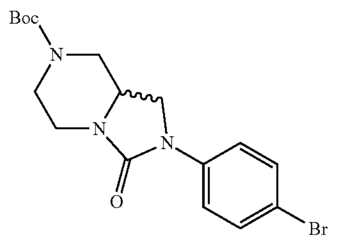 [SMILES: CC(C)(C)OC(=O)N1CCN2C(=O)N(c3ccc(Br)cc3)CC2C1]

To a solution of 500 mg (85) (0.79 mmol) in 9 ml dry DCM was added 1 ml TFA at ambient temperature. The mixture was stirred until TLC indicated the complete consumption of starting material (about 3 hours). The mixture was concentrated under reduced pressure and the residue was co-evaporated several times with DCM to remove excess of TFA and to obtain the bis-deprotected intermediate as dark sticky mass. The residue was taken up in 10 ml dry THF and 1 ml $Et_3N$ was added at ambient temperature. After 30 min of stirring, TLC indicated complete conversion and the mixture was diluted with EtOAc and transferred to a separatory funnel. The organic phase was washed with 1N NaOH (2×) and brine prior to drying over $Na_2SO_4$ and evaporation. The residue was taken up in 10 ml dry THF and 172 mg $Boc_2O$ (0.79 mmol) was added to the solution. The mixture was stirred overnight at ambient temperature, then evaporated to dryness and the residue was purified via flash chromatography (eluent A: hexane; eluent B: EtOAc/DCM/MeOH 47.5/47.5/5; gradient: 10 to 40% B). The title compound was obtained as 170 mg (55%) of a slightly brownish solid. $^1H$ NMR (400 MHz, $CDCl_3$) δ 7.56-7.29 (m, 4H), 4.34-4.02 (m, 2H), 3.96-3.82 (m, 2H), 3.77-3.67 (m, 1H), 3.39 (dd, J=9.2, 5.2 Hz, 1H), 2.94 (td, J=12.6, 3.3 Hz, 1H), 2.88-2.57 (m, 2H), 1.48 (s, 9H). $^{13}C$ NMR (101 MHz, $CDCl_3$) δ 155.9, 154.5, 139.4, 131.9, 118.9, 115.3, 80.8, 49.9, 46.3, 40.5, 28.5. ESI-MS m/z: 418.5 $[M+Na]^+$ HPLC $t_{ret}$=8.91 min.

(RS)-2-(4-Bromophenyl)-7-methylhexahydroimidazo[1,5-a]pyrazin-3(2H)-one (87)

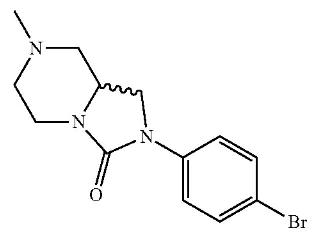 [SMILES: CN1CCN2C(=O)N(c3ccc(Br)cc3)CC2C1]

A suspension of 152 mg (86) (0.38 mmol) in 6 ml formic acid and 2 ml formalin was heated to 70° C. oil-bath temperature and stirring was continued until TLC confirmed major formation of the desired product. The reaction mixture was poured on ice/water and was basified with 30% wt aqueous NaOH under cooling followed by extraction with MTBE (3×25 ml). The combined organic phases were backwashed with brine, dried over $Na_2SO_4$ and evaporated. The crude product was purified via flash chromatography (DCM/MeOH+2N $NH_3$ 1-8%) to obtain 90 mg (76%) of the title compound as white solid. $^1H$ NMR (400 MHz, $CDCl_3$) δ 7.47-7.37 (m, 4H), 3.92 (ddd, J=13.2, 3.6, 1.2 Hz, 1H), 3.88-3.78 (m, 2H), 3.40-3.30 (m, 1H), 3.07 (ddd, J=13.2, 12.2, 3.6 Hz, 1H), 2.91-2.84 (m, 1H), 2.79-2.71 (m, 1H), 2.33 (s, 3H), 2.03 (td, J=11.7, 3.6 Hz, 1H), 1.96-1.85 (m, 1H). $^{13}C$ NMR (101 MHz, $CDCl_3$) δ 156.1, 139.6, 131.8, 118.8, 115.0, 59.5, 54.1, 50.1, 46.5, 46.4, 40.5. ESI-MS m/z: 364.5 $[M+MeOH+Na]^+$ HPLC $t_{ret}$=3.40 min.

Methyl (2S,4R)-4-hydroxypyrrolidine-2-carboxylate hydrochloride (88)

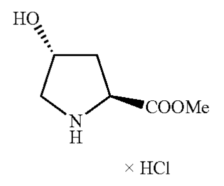

To an ice cooled slurry of 2.62 g (2S,4R)-4-hydroxypyrrolidine-2-carboxylic acid (20 mmol) in 40 ml MeOH were added dropwise 1.74 ml thionyl chloride (24 mmol). The cooling bath was removed and the mixture was stirred at ambient temperature overnight. The volatiles were removed under reduced pressure and the resultant white solid was triturated with acetone and isolated by filtration to yield 3.60 g (99%) of the title compound as white crystalline solid. $^1H$ NMR (200 MHz, DMSO) δ 10.06 (br s, 2H), 5.54 (br s, 1H), 4.51-4.31 (m, 2H), 3.73 (s, 3H), 3.37 (dd, J=12.0, 4.5 Hz, 1H), 3.15-2.95 (m, 1H), 2.28-1.95 (m, 2H). $^{13}$C NMR (50 MHz, DMSO) δ 169.0, 68.4, 57.5, 53.1, 53.0, 37.0.

1-(tert-Butyl) 2-methyl (2S,4R)-4-hydroxypyrrolidine-1,2-dicarboxylate (89)

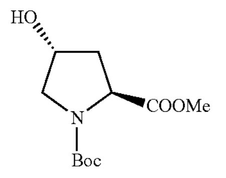 [SMILES: COC(=O)[C@@H]1C[C@@H](O)CN1C(=O)OC(C)(C)C]

To a solution of 2.50 g (88) (13.8 mmol) and 1.73 g $NaHCO_3$ (20.6 mmol) in a mixture of THF/water (20 ml each) were added 3.16 ml $Boc_2O$ (13.8 mmol) via syringe under ice-cooling. After gas evolution ceased, the cooling bath was removed and stirring was continued overnight at ambient temperature. The reaction was diluted with EtOAc and transferred to a separatory funnel. The phases were separated and the aqueous phase was further extracted with EtOAc (4×50 ml). The combined extracts were washed with 2N $NaHSO_4$ and brine, prior to drying over $Na_2SO_4$ and evaporation. The title compound was yielded as 3.25 g (96%) of a slightly yellowish oil. $^1$H NMR (200 MHz, $CDCl_3$) δ 4.56-4.28 (m, 2H), 3.72 (s, 3H), 3.68-3.36 (m, 2H), 2.38-2.18 (m, 1H), 2.17-1.97 (m, 2H), 1.49-1.30 (m, 9H). ESI-MS m/z: 267.8 $[M+Na]^+$ 1-(tert-Butyl) 2-methyl (2S,4R)-4-(tosyloxy)pyrrolidine-1,2-dicarboxylate (90)

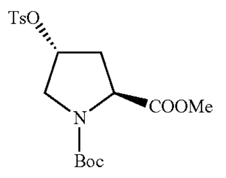 [SMILES: COC(=O)[C@@H]1C[C@@H](OS(=O)(=O)c2ccc(C)cc2)CN1C(=O)OC(C)(C)C]

In a 100 ml round-bottomed flask were dissolved 2.90 g (89) (11.8 mmol), 1.59 g DMAP (13.0 mmol) and 1.83 ml $Et_3N$ (13.0 mmol) in 50 ml DCM and 2.48 g TsCl (13 mmol) were added subsequently under ice cooling. After 30 min, the cooling bath was removed and the mixture was stirred at ambient temperature until TLC indicated complete conversion (ca. 4 hours). The mixture was diluted with DCM and poured on 2N HCl. The phases were separated and the organic phase was washed once more with 2N HCl. The organic phase was further washed with water and brine before it was dried over $Na_2SO_4$ and concentrated under reduced pressure. The title compound was yielded as 4.51 g (96%) as a yellow sticky syrup. $^1$H NMR (200 MHz, $CDCl_3$) δ 7.75 (d, J=8.1 Hz, 2H), 7.33 (d, J=8.1 Hz, 2H), 5.08-4.91 (m, 1H), 4.33 (q, J=7.8 Hz, 1H), 3.68 (s, 3H), 3.62-3.43 (m, 2H), 2.57-2.29 (m, 4H), 2.23-1.97 (m, 1H), 1.45-1.27 (m, 9H). $^{13}$C NMR (50 MHz, $CDCl_3$) δ 172.8, 172.6, 153.9, 153.2, 145.4, 133.6, 133.4, 130.2, 127.8, 80.8, 79.1, 78.5, 57.4, 57.1, 52.4, 52.3, 51.9, 37.2, 36.1, 28.3, 28.2, 21.7. (complex signal splitting due to amide rotamers) ESI-MS m/z: 421.8 $[M+Na]^+$ HPLC $t_{ret}$=8.08 min.

tert-Butyl (2S,4R)-2-(hydroxymethyl)-4-(tosyloxy)pyrrolidine-1-carboxylate (91)

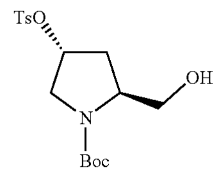 [SMILES: Cc1ccc(S(=O)(=O)O[C@@H]2C[C@@H](CO)N(C(=O)OC(C)(C)C)C2)cc1]

Under argon atmosphere were dissolved 1.26 g dry LiBr (14.5 mmol)) were dissolved in 30 ml dry THF. To the stirred solution were added 520 mg $NaBH_4$ and the resulting suspension was heated to reflux overnight with vigorous stirring. The heating bath was then replaced by an ice bath and 3.63 g (90) (9.09 mmol) were added as solution in 5 ml THF. After complete addition, the cooling bath was removed and stirring was continued at ambient temperature until TLC indicated complete conversion (about 3 hours). The mixture was cooled with an ice/water bath and the reaction was carefully quenched with MeOH and subsequently with 2N HCl until gas evolution ceased and an acidic pH persisted. The mixture was transferred to a separatory funnel and the aqueous phase was extracted with EA (4×75 ml). The combined organic phases were washed with water and brine prior to drying over $Na_2SO_4$ and evaporation of the solvents. The title compound was yielded as 3.29 g (98%) of a colorless sticky residue. $^1$H NMR (200 MHz, $CDCl_3$) δ 7.87-7.65 (m, 2H), 7.34 (d, J=7.8 Hz, 2H), 5.11-4.87 (m, 1H), 4.60 (br s) and 4.14-3.82 (m, 2H), 3.81-3.16 (m, 4H), 2.43 (s, 3H), 2.30-1.64 (m, 2H), 1.57-1.26 (m, 9H). ESI-MS m/z: 394.0 $[M+Na]^+$ HPLC $t_{ret}$=7.58 min.

tert-Butyl (2S,4R)-2-(((4-bromophenyl)amino)methyl)-4-(tosyloxy)pyrrolidine-1-carboxylate

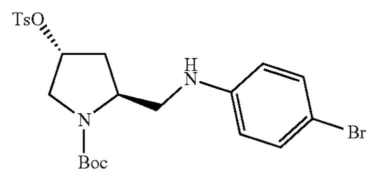 [SMILES: Cc1ccc(S(=O)(=O)O[C@@H]2C[C@@H](CNc3ccc(Br)cc3)N(C(=O)OC(C)(C)C)C2)cc1]

A schlenk flask containing a solution of 414 µl oxalyl chloride (4.8 mmol) in 25 ml dry DCM was cooled to −78° C. using acetone/liquid nitrogen. Under argon atmosphere were added 369 µl DMSO (5.2 mmol) as solution in 1 ml DCM dropwise with vigorous stirring. Stirring was continued for about 15 min before a solution of 1.38 g (91) (3.7 mmol) in 5 ml DCM was added slowly to the reaction mixture. After another 30 min of stirring, 1.57 ml $Et_3N$ (11.1 mmol) were dropwise and stirring was continued for about one hour. The reaction was quenched by the addition of 5 ml water and the mixture was allowed to reach ambient temperature. After dilution with DCM, the organic phase was successively washed with water (2×), sat. $NaHCO_3$ and brine. The organic phase was dried over $Na_2SO_4$ and concentrated under reduced pressure, yielding the aldehyde intermediate as amber oil, which was directly used without further purification.

The crude aldehyde was taken up in 20 ml dry DCM and 639 mg 4-bromoaniline (3.7 mmol) and 1.78 g sodium triacetoxy borohydride (9.3 mmol) were added subsequently at ambient temperature. After about two hours, TLC indicated complete conversion and the reaction was quenched by the addition of water. The mixture was extracted twice with DCM and the combined extracts were backwashed with sat. $NaHCO_3$ and brine. After drying over $Na_2SO_4$ and evaporation of the solvents, an oily brownish residue was obtained. This was subjected to flash purification (hexane/EtOAc+5% MeOH 5-25%) to yield 1.07 g (55%) of the title compound as slightly yellow oil, which darkens rapidly upon light exposure and should be kept in the freezer. $^1H$ NMR (400 MHz, $CDCl_3$) δ 7.75 (d, J=8.1 Hz, 2H), 7.33 (d, J=8.1 Hz, 2H), 7.19 (d, J=8.6 Hz, 2H), 6.45 (d, J=8.6 Hz, 2H), 4.98 (br s, 1H), 4.26-4.12 (m, 1H), 3.78-3.63 (m, 1H), 3.40-3.06 (m, 3H), 2.44 (s, 3H), 2.37-2.18 (m, 1H), 2.02-1.80 (m, 1H), 1.44 (s, 9H). ESI-MS m/z: 547.5 $[M+Na]^+$ HPLC $t_{ret}$=10.26 min.

tert-Butyl (2S,4R)-2-(((4-bromophenyl)((4-nitrophenoxy)carbonyl)amino)methyl)-4-(tosyloxy)pyrrolidine-1-carboxylate (93)

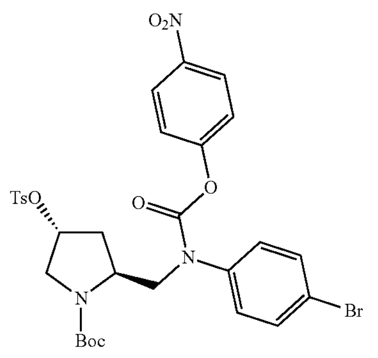 [SMILES: Cc1ccc(S(=O)(=O)O[C@@H]2C[C@@H](CN(C(=O)Oc3ccc([N+](=O)[O-])cc3)c3ccc(Br)cc3)N(C(=O)OC(C)(C)C)C2)cc1]

To a solution of 1.0 g (92) (1.90 mmol) in ca. 10 ml DCM were added 169 μl pyridine (2.09 mmol) and the solution was cooled in an ice/water bath. Subsequently was added a solution of 422 mg p-nitrophenylchloroformate (2.09 mmol) in 2 ml DCM and the mixture was stirred until TLC indicated complete conversion (about 30 min). The reaction was quenched by pouring on 2N HCl followed by extraction with DCM (2×20 ml). The combined extracts were washed with sat. $NaHCO_3$ and brine, prior to drying over $Na_2SO_4$ and evaporation. The residue was purified via flash chromatography (hexane/EtOAc 10-40%) to yield 1.07 g (81%) of the title compound as white foam. $^1H$ NMR (400 MHz, $CDCl_3$) δ 8.20 (d, J=8.2 Hz, 2H), 7.75 (d, J=8.2 Hz, 2H), 7.59-7.44 (m, 2H), 7.33 (d, J=8.2 Hz, 2H), 7.30-7.08 (m, 4H), 5.08-4.89 (m, 1H), 4.26-3.84 (m, 3H), 3.79-3.57 (m, 1H), 3.28 (dd, J=13.0, 3.8 Hz, 1H), 2.43 (s, 3H), 2.31-1.95 (m, 2H), 1.32 (s, 9H). ESI-MS m/z: 712.8 $[M+Na]^+$ HPLC $t_{ret}$=10.30 min.

(6R,7aS)-2-(4-Bromophenyl)-3-oxohexahydro-1H-pyrrolo[1,2-c]imidazol-6-yl 4-methylbenzenesulfonate (94)

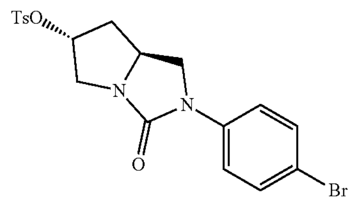 [SMILES: Cc1ccc(S(=O)(=O)O[C@@H]2C[C@H]3CN(c4ccc(Br)cc4)C(=O)N3C2)cc1]

To a solution of 1.02 g (93) (1.48 mmol) in 9 ml dry DCM was added 1 ml TFA at ambient temperature. The mixture was stirred until TLC indicated the complete consumption of starting material (about 3 hours). The mixture was concentrated under reduced pressure and the residue was coevaporated several times with DCM to remove excess of TFA and to finally obtain the deprotected intermediate as reddish foam. The residue was taken up in 10 ml dry DCM and 0.62 ml $Et_3N$ (4.43 mmol) were added at ambient temperature. After 30 min of stirring, TLC indicated complete conversion and the mixture was diluted with DCM and transferred to a separatory funnel. The organic phase was successively washed with 1N NaOH (2×), 2N HCL and brine prior to drying over $Na_2SO_4$ and evaporation. The title compound was obtained as 660 mg (99%) of a reddish solid and was sufficiently pure for the next step. $^1H$ NMR (400 MHz, $CDCl_3$) δ 7.78 (d, J=8.2 Hz, 2H), 7.52-7.39 (m, 4H), 7.37 (d, J=8.2 Hz, 2H), 5.19-5.03 (m, 1H), 4.08-3.93 (m, 3H), 3.66 (dd, J=9.3, 1.2 Hz, 1H), 3.17-3.09 (m, 1H), 2.46 (s, 3H), 2.33 (dd, J=14.0, 5.0 Hz, 1H), 1.61 (ddd, J=14.0, 10.7, 5.8 Hz, 1H). $^{13}C$ NMR (101 MHz, $CDCl_3$) δ 159.9, 145.5, 138.9, 133.5, 131.9, 130.3, 127.9, 119.3, 116.0, 81.2, 53.7, 53.0, 46.8, 38.7, 21.8. ESI-MS m/z: 473.6 $[M+Na]^+$ HPLC $t_{ret}$=8.64 min.

(6S,7aS)-2-(4-Bromophenyl)-6-(dimethylamino)hexahydro-3H-pyrrolo[1,2-c]imidazol-3-one (95)

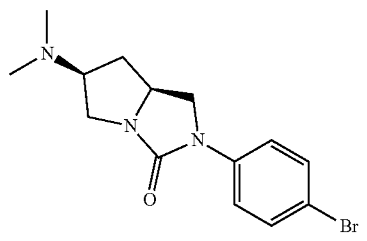 [SMILES: CN(C)[C@H]1C[C@H]2CN(c3ccc(Br)cc3)C(=O)N2C1]

A suspension of 181 mg (94) (0.40 mmol) in 3 ml of a 2N methanolic dimethylamine solution was heated under microwave irradiation (80W) to 100° C. over 15 min. At this point TLC indicated complete conversion and the majority of MeOH was removed under reduced pressure. The residue was taken up in EtOAc and washed with 1N NaOH (2×) and brine. The organic phase was dried over $Na_2SO_4$ and concentrated under reduced pressure. The residue was purified via flash chromatography (DCM/MeOH+2N $NH_3$ 1-7%) to obtain 110 mg (85%) of the title compound as off-white crystalline solid. $^1H$ NMR (400 MHz, $CDCl_3$) δ 7.46 (d, J=8.2 Hz, 2H), 7.40 (d, J=8.2 Hz, 2H), 3.95-3.82 (m, 2H), 3.71-3.65 (m, 1H), 3.58 (dd, J=11.2, 7.1 Hz, 1H), 3.29 (dd, J=11.2, 8.0 Hz, 1H), 3.05-2.94 (m, 1H), 2.22 (s, 6H), 2.16 (dt, J=11.2, 5.6 Hz, 1H), 1.52-1.41 (m, 1H). $^{13}C$ NMR (101 MHz, $CDCl_3$) δ 160.1, 139.4, 131.8, 119.2, 115.3, 67.7, 54.7, 49.7, 47.8, 44.1, 36.4. ESI-MS m/z: 324.6 $[M+H]^+$ HPLC $t_{ret}$=3.66 min.

(6S,7aS)-2-(4-Bromophenyl)-6-hydroxyhexahydro-3H-pyrrolo[1,2-c]imidazol-3-one (96)

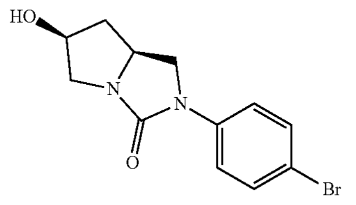 [SMILES: O=C1N(c2ccc(Br)cc2)C[C@@H]2C[C@H](O)CN12]

A suspension of 1.83 g tetraethylammonium acetate tetrahydrate (7 mmol) and 316 mg (94) (0.70 mmol) in 40 ml EtOAc was heated to 60° C. for one hour. TLC indicated complete conversion at this point and the mixture was cooled back to ambient temperature and transferred to an separatory funnel. The organic phase was washed with water and brine prior to drying over $Na_2SO_4$ and evaporation. The pale brownish residue was redissolved in THF/MeOH (3 ml each) and 3 ml of an 1M aqueous LiOH solution were added subsequently. After stirring for one hour at ambient temperature, TLC indicated complete conversion and the reaction was quenched by pouring on water. The aqueous phase was extracted with EtOAc (3×15 ml) and the combined extracts were backwashed with brine prior to drying over $Na_2SO_4$ and evaporation. The title compound was yielded as 198 mg (95%) of an off-white solid. $^1H$ NMR (400 MHz, DMSO) δ 7.55 (d, J=8.5 Hz, 2H), 7.49 (d, J=8.5 Hz, 2H), 4.86 (d, J=1.7 Hz, 1H), 4.29 (br s, 1H), 4.03-3.94 (m, 1H), 3.94-3.84 (m, 1H), 3.72 (dd, J=8.7, 3.6 Hz, 1H), 3.50 (d, J=11.6 Hz, 1H), 2.99 (dd, J=11.9, 4.2 Hz, 1H), 2.31-2.13 (m, 1H), 1.61-1.49 (m, 1H). $^{13}C$ NMR (101 MHz, DMSO) δ 160.5, 139.7, 131.3, 119.0, 113.5, 70.9, 55.0, 52.8, 49.5, 40.6. ESI-MS m/z: 351.4 $[M+MeOH+Na]^+$ HPLC $t_{ret}$=5.59 min.

(6S,7aS)-2-(4-Bromophenyl)-3-oxohexahydro-1H-pyrrolo[1,2-c]imidazol-6-yl 4-methylbenzenesulfonate (97)

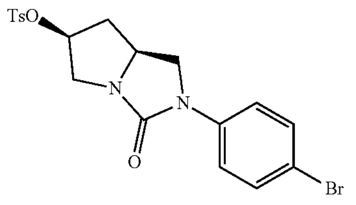 [SMILES: Cc1ccc(S(=O)(=O)O[C@H]2C[C@H]3CN(c4ccc(Br)cc4)C(=O)N3C2)cc1]

To a solution of 185 mg (96) (0.62 mmol) in 1.5 ml pyridine were added 178 mg tosylchloride (0.93 mmol) as solid in one portion. The reaction was stirred at ambient temperature for 48 hours and was then quenched by addition of 2N aqueous HCl. After extraction with EtOAc (2×20 ml), the combined extracts were backwashed with 2N HCl and brine, prior to drying over $Na_2SO_4$ and evaporation. The residue was subjected to flash purification (hexane/EtOAc+5% MeOH 10-60%) to obtain 171 mg (61%) of the title compound as white solid. $^1H$ NMR (400 MHz, $CDCl_3$) δ 7.71 (d, J=8.2 Hz, 2H), 7.50-7.33 (m, 4H), 7.26 (d, J=8.2 Hz, 2H), 5.22-5.09 (m, 1H), 4.04-3.87 (m, 3H), 3.69-3.56 (m, 1H), 3.09 (dd, J=13.6, 4.7 Hz, 1H), 2.52-2.42 (m, 1H), 2.41 (s, 3H), 2.07-1.93 (m, 1H). $^{13}C$ NMR (101 MHz, $CDCl_3$) δ 160.2, 145.2, 139.0, 133.6, 131.8, 130.0, 127.8, 119.7, 115.8, 81.1, 53.0, 52.8, 49.5, 39.2, 21.7. ESI-MS m/z: 473.7 $[M+Na]^+$ HPLC $t_{ret}$=8.33 min.

(6R,7aS)-2-(4-Bromophenyl)-6-(dimethylamino)hexahydro-3H-pyrrolo[1,2-c]imidazol-3-one (98)

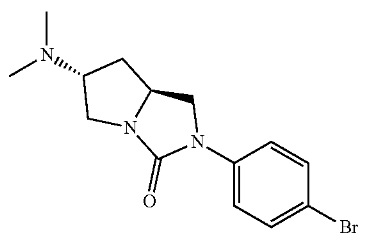 [SMILES: CN(C)[C@@H]1C[C@H]2CN(c3ccc(Br)cc3)C(=O)N2C1]

A suspension of 171 mg (97) (0.38 mmol) in 3 ml of a 2N methanolic dimethylamine solution was heated under microwave irradiation (80W) to 100° C. over 30 min. At this point TLC indicated complete conversion and the majority of MeOH was removed under reduced pressure. The residue was taken up in EtOAc and washed with 1N NaOH (2×) and brine. The organic phase was dried over $Na_2SO_4$ and concentrated under reduced pressure. The residue was purified via flash chromatography (DCM/MeOH+2N $NH_3$ 1-7%) to obtain 104 mg (84%) of the title compound as off-white crystalline solid. $^1H$ NMR (400 MHz, $CDCl_3$) δ 7.48-7.37 (m, 4H), 4.06-3.98 (m, 2H), 3.95 (t, J=8.7 Hz, 1H), 3.59 (dd, J=8.9, 2.8 Hz, 1H), 2.93 (dd, J=12.0, 7.2 Hz, 1H), 2.89-2.80 (m, 1H), 2.25 (s, 6H), 2.20-2.12 (m, 1H), 1.71 (ddd, J=13.5, 8.5, 7.1 Hz, 1H). $^{13}C$ NMR (101 MHz, $CDCl_3$) δ 160.1, 139.3, 131.9, 119.3, 115.6, 65.6, 53.7, 50.6, 49.5, 43.9, 36.4. ESI-MS m/z: 324.3 $[M+H]^+$ HPLC $t_{ret}$=3.73 min.

1-(tert-Butyl) 2-methyl (2R,4R)-4-hydroxypyrrolidine-1,2-dicarboxylate (99)

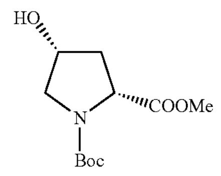 [SMILES: COC(=O)[C@H]1C[C@@H](O)CN1C(=O)OC(C)(C)C]

To an ice-cooled solution of 1.97 g (2R,4R)-4-hydroxypyrrolidine-2-carboxylic acid (15 mmol) in 30 ml MeOH were added dropwise 1.63 ml thionyl chloride (22.5 mmol) in a rate that held the exothermic reaction under control. After complete addition, the cooling bath was removed and the reaction was heated to reflux for three hours. After cooling back to ambient temperature, the mixture was concentrated under reduced pressure. Due to undefined inpurities in the starting material, the crude hydrochloride salt of the ester could only be obtained as brown to black colored, amorphous residue, which was carried on directly to the following Boc protection.

The crude material was taken up in THF/water (20 ml each) and subsequently 1.89 g $NaHCO_3$ (22.5 mmol) and 3.27 g $Boc_2O$ (15 mmol) were added. The dark mixture was stirred overnight at ambient temperature and was then diluted with EtOAc and transferred to a separatory funnel. The organic phase was successively washed with water, 2N HCl and brine, which removed majority of the dark inpurities. The organic phase was then stirred with $Na_2SO_4$, silica and activated carbon for 90 min at ambient temperature, before it was filtered over a bed of celite and evaporated under reduced pressure. The title compound was obtained as 3.36 g (91%) of a colorless oil. $^1H$ NMR (400 MHz, $CDCl_3$) δ 4.40-4.22 (m, 2H), 3.84-3.70 (m, 3H), 3.69-3.56 (m, 1H), 3.56-3.46 (m, 1H), 2.39-2.22 (m, 1H), 2.12-2.01 (m, 1H), 1.47-1.34 (m, 9H). $^{13}C$ NMR (101 MHz, $CDCl_3$) δ 175.7, 175.4, 154.6, 153.8, 80.5, 71.4, 70.3, 58.0, 57.8, 56.1, 55.5, 52.8, 52.5, 38.7, 37.9, 28.5, 28.4.

1-(tert-Butyl) 2-methyl (2R,4R)-4-(tosyloxy)pyrrolidine-1,2-dicarboxylate (100)

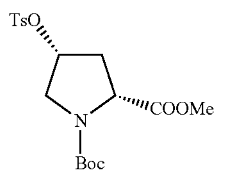 [SMILES: COC(=O)[C@H]1C[C@@H](OS(=O)(=O)c2ccc(C)cc2)CN1C(=O)OC(C)(C)C]

In a 100 ml round-bottomed flask were dissolved 3.13 g (99) (12.8 mmol), 1.71 g DMAP (14.0 mmol) and 1.97 ml $Et_3N$ (14.0 mmol) in 40 ml DCM and 2.68 g TsCl (14 mmol) were added subsequently under ice cooling. After 30 min, the cooling bath was removed and the mixture was stirred at ambient temperature overnight. The mixture was diluted with DCM and poured on 2N HCl. The phases were separated and the organic phase was washed once more with 2N HCl. The organic phase was further washed with water and brine before it was dried over $Na_2SO_4$ and concentrated under reduced pressure. The title compound was yielded as 4.78 g (94%) as a yellow sticky syrup. $^1H$ NMR (400 MHz, $CDCl_3$) δ 7.72 (d, J=8.0 Hz, 2H), 7.32 (d, J=8.0 Hz, 2H), 5.07-4.96 (m, 1H), 4.42-4.26 (m, 1H), 3.72-3.59 (m, 3H), 3.62 (s, J=12.4 Hz, 1H), 3.59-3.51 (m, 1H), 2.42 (s, 3H), 2.48-2.27 (m, 2H), 1.42-1.33 (m, 9H). $^{13}C$ NMR (101 MHz, $CDCl_3$) δ 172.0, 171.6, 153.8, 153.4, 145.2, 133.8, 130.0, 127.8, 80.6, 78.9, 77.7, 57.5, 57.1, 52.2, 52.1, 51.6, 37.0, 36.0, 28.3, 21.7. ESI-MS m/z: 422.4 $[M+Na]^+$ HPLC $t_{ret}$=7.72 min.

tert-Butyl (2R,4R)-2-(hydroxymethyl)-4-(tosyloxy)pyrrolidine-1-carboxylate (101)

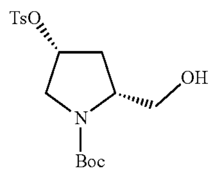 [SMILES: Cc1ccc(S(=O)(=O)O[C@@H]2C[C@H](CO)N(C(=O)OC(C)(C)C)C2)cc1]

To a solution of 1.65 g dry LiBr (19.0 mmol) in 30 ml dry THF were added 0.67 g $NaBH_4$ under argon atmosphere and the resulting suspension was heated to reflux overnight with vigorous stirring. The heating bath was then replaced by an ice bath and 4.75 g (100) (11.9 mmol) were added as solution in 10 ml THF. After complete addition, the cooling bath was removed and stirring was continued at ambient temperature until TLC indicated complete conversion (about 3 hours). The mixture was cooled with an ice/water bath and the reaction was carefully quenched with MeOH and subsequently with 2N HCl until gas evolution ceased and an acidic pH persisted. The mixture was transferred to a separatory funnel and the aqueous phase was extracted with EtOAc (4×75 ml). The combined organic phases were washed with water and brine prior to drying over $Na_2SO_4$ and evaporation of the solvents. The title compound was obtained as 4.11 g (93%) of a colorless sticky residue, which solidifies slowly upon standing. $^1H$ NMR (400 MHz, $CDCl_3$) δ 7.75 (d, J=8.2 Hz, 2H), 7.33 (d, J=8.2 Hz, 2H), 5.01-4.89 (m, 1H), 4.03-3.79 (m, 2H), 3.74 (dd, J=11.0, 7.5 Hz, 1H), 3.64-3.39 (m, 3H), 2.42 (s, 3H), 2.25-2.15 (m, 1H), 1.96-1.70 (m, 1H), 1.40 (s, 9H). ESI-MS m/z: 394.6 $[M+Na]^+$ HPLC $t_{ret}$=7.64 min.

tert-Butyl (2R,4R)-2-(((4-bromophenyl)amino)methyl)-4-(tosyloxy)pyrrolidine-1-carboxylate (102)

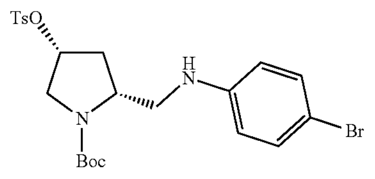 [SMILES: Cc1ccc(S(=O)(=O)O[C@@H]2C[C@H](CNc3ccc(Br)cc3)N(C(=O)OC(C)(C)C)C2)cc1]

A schlenk flask containing a solution of 600 µl oxalyl chloride (7.0 mmol) in 25 ml dry DCM was cooled to −78° C. using acetone/liquid nitrogen. Under argon atmosphere were added 535 µl DMSO (7.5 mmol) as solution in 1 ml DCM dropwise with vigorous stirring. Stirring was continued for about 15 min before a solution of 2.0 g (101) (3.7 mmol) in 5 ml DCM was added slowly to the reaction mixture. After another 30 min of stirring, 2.27 ml $Et_3N$ (16.2 mmol) were dropwise and stirring was continued for about one hour. The reaction was quenched by the addition of 5 ml water and the mixture was allowed to reach ambient temperature. After dilution with DCM, the organic phase was successively washed with water (2×), sat. $NaHCO_3$ and brine. The organic phase was dried over $Na_2SO_4$ and concentrated under reduced pressure, yielding the aldehyde intermediate as amber oil, which was directly used without further purification.

The crude aldehyde was taken up in 20 ml dry DCM and 639 mg 4-bromoaniline (3.7 mmol) and 2.28 g sodium triacetoxy borohydride (10.8 mmol) were added subsequently at ambient temperature. After about two hours, TLC indicated complete conversion and the reaction was quenched by the addition of water. The mixture was extracted twice with DCM and the combined extracts were backwashed with sat. $NaHCO_3$ and brine. After drying over $Na_2SO_4$ and evaporation of the solvents, an oily brownish residue was obtained. This was subjected to flash purification (hexane/EtOAc+5% MeOH 5-25%) to yield 1.43 g (50%) of the title compound as slightly yellow oil, which darkens rapidly upon light exposure and should be kept in the freezer. ESI-MS m/z: 547.7 $[M+Na]^+$ HPLC $t_{ret}$=10.46 min.

tert-Butyl (2R,4R)-2-(((4-bromophenyl)((4-nitrophenoxy)carbonyl)amino)methyl)-4-(tosyloxy)pyrrolidine-1-carboxylate (103)

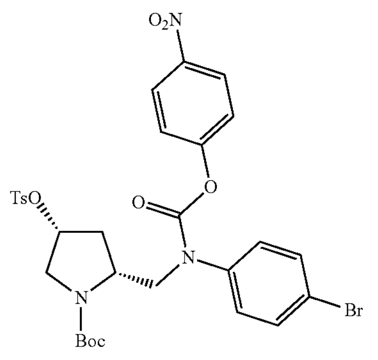 [SMILES: Cc1ccc(S(=O)(=O)O[C@@H]2C[C@H](CN(C(=O)Oc3ccc([N+](=O)[O-])cc3)c3ccc(Br)cc3)N(C(=O)OC(C)(C)C)C2)cc1]

To a solution of 1.43 g (102) (2.7 mmol) in ca. 10 ml DCM were added 241 μl pyridine (2.98 mmol) and the solution was cooled in an ice/water bath. Subsequently was added a solution of 601 mg p-nitrophenylchloroformate (2.89 mmol) in 2 ml DCM and the mixture was stirred until TLC indicated complete conversion (about 30 min). The reaction was quenched by pouring on 2N HCl followed by extraction with DCM (2×20 ml). The combined extracts were washed with sat. $NaHCO_3$ and brine, prior to drying over $Na_2SO_4$ and evaporation. The residue was purified via flash chromatography (hexane/EtOAc 10-40%) to yield 1.27 g (68%) of the title compound as sticky oily residue. $^1H$ NMR (400 MHz, $CDCl_3$) δ 8.19 (d, J=8.2 Hz, 2H), 7.79-7.62 (m, 2H), 7.61-7.46 (m, 2H), 7.46-6.93 (m, 6H), 5.10-4.93 (m, 1H), 4.45-3.89 (m, 3H), 3.78-3.37 (m, 2H), 2.42 (s, 3H), 2.32-2.02 (m, 2H), 1.45-1.29 (m, 9H). ESI-MS m/z: 713.1 $[M+Na]^+$ HPLC $t_{ret}$=10.44 min.

(6R,7aR)-2-(4-Bromophenyl)-3-oxohexahydro-1H-pyrrolo[1,2-c]imidazol-6-yl 4-methylbenzenesulfonate (104)

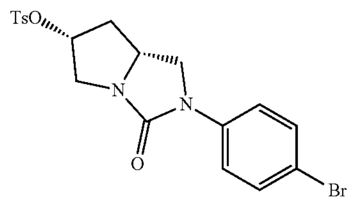 [SMILES: Cc1ccc(S(=O)(=O)O[C@@H]2C[C@@H]3CN(c4ccc(Br)cc4)C(=O)N3C2)cc1]

To a solution of 885 mg (103) (1.28 mmol) in 9 ml dry DCM was added 1 ml TFA at ambient temperature. The mixture was stirred until TLC indicated the complete consumption of starting material (about 3 hours). The mixture was concentrated under reduced pressure and the residue was coevaporated several times with DCM to remove excess of TFA and to finally obtain the deprotected intermediate as reddish foam. The residue was taken up in 10 ml dry DCM and 0.54 ml $Et_3N$ (3.85 mmol) were added at ambient temperature. After 30 min of stirring, TLC indicated complete conversion and the mixture was diluted with DCM and transferred to a separatory funnel. The organic phase was successively washed with 1N NaOH (2×), 2N HCL and brine prior to drying over $Na_2SO_4$ and evaporation. The residue was purified via flash chromatography (hexane/EtOAc+5% MeOH 20-60%) to obtain 466 mg (81%) of the title compound as off-white solid. $^1H$ NMR (400 MHz, $CDCl_3$) δ 7.71 (d, J=8.2 Hz, 2H), 7.44-7.35 (m, 4H), 7.26 (d, J=8.2 Hz, 2H), 5.19-5.11 (m, 1H), 4.01-3.89 (m, 3H), 3.63 (dd, J=7.9, 2.2 Hz, 1H), 3.10 (dd, J=13.6, 4.7 Hz, 1H), 2.51-2.42 (m, 1H), 2.41 (s, 3H), 2.05-1.96 (m, 1H). $^{13}C$ NMR (101 MHz, $CDCl_3$) δ 160.2, 145.2, 138.9, 133.5, 131.8, 130.0, 127.8, 119.6, 115.8, 81.1, 53.0, 52.8, 49.4, 39.2, 21.7. ESI-MS m/z: 473.5 $[M+Na]^+$ HPLC $t_{ret}$=8.38 min.

(6S,7aR)-2-(4-Bromophenyl)-6-(dimethylamino)hexahydro-3H-pyrrolo[1,2-c]imidazol-3-one (105)

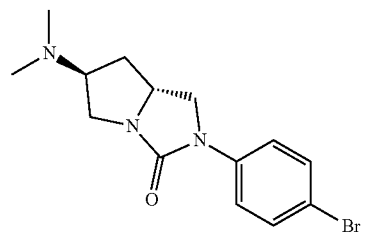 [SMILES: CN(C)[C@H]1C[C@@H]2CN(c3ccc(Br)cc3)C(=O)N2C1]

A suspension of 140 mg (104) (0.31 mmol) in 3 ml of a 2N methanolic dimethylamine solution was heated under microwave irradiation (80W) to 100° C. over 30 min. At this point TLC indicated complete conversion and the majority of MeOH was removed under reduced pressure. The residue was taken up in EtOAc and washed with 1N NaOH (2×) and brine. The organic phase was dried over $Na_2SO_4$ and concentrated under reduced pressure. The residue was purified via flash chromatography (DCM/MeOH+2N $NH_3$ 1-7%) to obtain 90 mg (90%) of the title compound as off-white crystalline solid. $^1H$ NMR (400 MHz, $CDCl_3$) δ 7.51-7.37 (m, 4H), 4.07-3.99 (m, 2H), 3.96 (t, J=8.7 Hz, 1H), 3.60 (dd, J=9.0, 2.8 Hz, 1H), 2.94 (dd, J=12.0, 7.2 Hz, 1H), 2.90-2.81 (m, 1H), 2.26 (s, 6H), 2.21-2.14 (m, 1H), 1.72 (ddd, J=13.5, 8.5, 7.1 Hz, 1H). $^{13}C$ NMR (101 MHz, $CDCl_3$) δ 160.1, 139.2, 131.9, 119.2, 115.6, 65.5, 53.7, 50.6, 49.5, 43.9, 36.4. ESI-MS m/z: 324.5 $[M+H]^+$ HPLC $t_{ret}$=3.75 min.

(6S,7aR)-2-(4-Bromophenyl)-6-hydroxyhexahydro-3H-pyrrolo[1,2-c]imidazol-3-one (106)

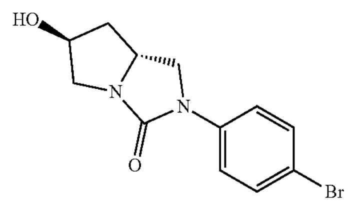 [SMILES: O=C1N(c2ccc(Br)cc2)C[C@H]2C[C@H](O)CN12]

A suspension of 1.78 g tetraethylammonium acetate tetrahydrate (6.8 mmol) and 307 mg (104) (0.68 mmol) in 40 ml EtOAc was heated to 60° C. for one hour. TLC indicated complete conversion at this point and the mixture was cooled back to ambient temperature and transferred to an separatory funnel. The organic phase was washed with water and brine prior to drying over $Na_2SO_4$ and evaporation. The pale brownish residue was redissolved in THF/MeOH (2 ml each) and 2 ml of an 1M aqueous LiOH solution were added subsequently. After stirring for one hour at ambient temperature, TLC indicated complete conversion and the reaction was quenched by pouring on water. The aqueous phase was extracted with EtOAc (3×15 ml) and the combined extracts were backwashed with brine prior to drying over $Na_2SO_4$ and evaporation. The title compound was yielded as 200 mg (99%) of an off-white solid. $^1H$ NMR (400 MHz, DMSO) δ 7.58-7.46 (m, 4H), 5.03 (d, J=3.6 Hz, 1H), 4.37 (dd, J=9.4, 5.3 Hz, 1H), 4.07-4.00 (m, 1H), 3.97 (t, J=8.9 Hz, 1H), 3.74 (dd, J=6.7, 4.0 Hz, 2H), 2.86 (d, J=12.1 Hz, 1H), 1.93 (dd, J=12.7, 5.2 Hz, 1H), 1.49 (ddd, J=12.8, 10.4, 5.3 Hz, 1H). $^{13}C$ NMR (101 MHz, DMSO) δ 159.7, 139.6, 131.3, 119.0, 113.7, 70.4, 55.3, 53.2, 46.9, 40.5. ESI-MS m/z: 351.5 $[M+MeOH+Na]^+$ HPLC $t_{ret}$=6.41 min.

(6S,7aR)-2-(4-Bromophenyl)-3-oxohexahydro-1H-pyrrolo[1,2-c]imidazol-6-yl 4-methylbenzenesulfonate (107)

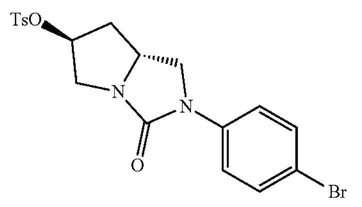 [SMILES: Cc1ccc(S(=O)(=O)O[C@H]2C[C@@H]3CN(c4ccc(Br)cc4)C(=O)N3C2)cc1]

To a solution of 186 mg (106) (0.63 mmol) in 1.5 ml pyridine were added 179 mg tosylchloride (0.94 mmol) as solid in one portion. The reaction was stirred at ambient temperature for 120 hours and was then quenched by addition of 2N aqueous HCl. After extraction with EtOAc (2×20 ml), the combined extracts were backwashed with 2N HCl and brine, prior to drying over $Na_2SO_4$ and evaporation. The residue was subjected to flash purification (hexane/EtOAc+5% MeOH 10-60%) to obtain 154 mg (55%) of the title compound as white solid. $^1H$ NMR (400 MHz, $CDCl_3$) δ 7.79 (d, J=8.3 Hz, 2H), 7.47-7.39 (m, 4H), 7.37 (d, J=8.3 Hz, 2H), 5.12 (t, J=5.7 Hz, 1H), 4.10-3.94 (m, 3H), 3.66 (dd, J=9.4, 1.6 Hz, 1H), 3.14 (dd, J=13.9, 1.2 Hz, 1H), 2.47 (s, 3H), 2.34 (dd, J=13.9, 5.0 Hz, 1H), 1.62 (ddd, J=14.0, 10.6, 5.8 Hz, 1H). $^{13}C$ NMR (101 MHz, $CDCl_3$) δ 159.9, 145.5, 138.9, 133.6, 132.0, 130.3, 127.9, 119.3, 116.0, 81.2, 53.7, 53.0, 46.8, 38.7, 21.8. HPLC $t_{ret}$=8.64 min.

(6R,7aR)-2-(4-Bromophenyl)-6-(dimethylamino)hexahydro-3-pyrrolo[1,2-c]imidazol-3-one (108)

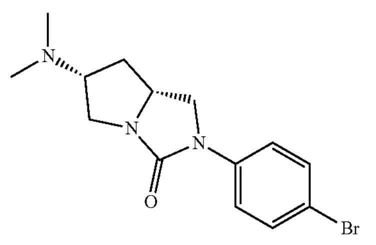 [SMILES: CN(C)[C@@H]1C[C@@H]2CN(c3ccc(Br)cc3)C(=O)N2C1]

A suspension of 154 mg (107) (0.34 mmol) in 3 ml of a 2N methanolic dimethylamine solution was heated under microwave irradiation (80W) to 100° C. over 15 min. At this point TLC indicated complete conversion and the majority of MeOH was removed under reduced pressure. The residue was taken up in EtOAc and washed with 1N NaOH (2×) and brine. The organic phase was dried over $Na_2SO_4$ and concentrated under reduced pressure. The residue was purified via flash chromatography (DCM/MeOH+2N $NH_3$ 1-7%) to obtain 92 mg (83%) of the title compound as off-white crystalline solid. $^1H$ NMR (400 MHz, $CDCl_3$) δ 7.54-7.37 (m, 4H), 3.98-3.81 (m, 2H), 3.69 (dd, J=8.6, 2.1 Hz, 1H), 3.60 (dd, J=11.4, 7.0 Hz, 1H), 3.30 (dd, J=11.4, 7.9 Hz, 1H), 3.03 (ddd, J=14.5, 9.9, 7.0 Hz, 1H), 2.24 (s, 6H), 2.22-2.14 (m, 1H), 1.55-1.41 (m, 1H). $^{13}C$ NMR (101 MHz, $CDCl_3$) δ 160.1, 139.4, 131.8, 119.2, 115.4, 67.7, 54.7, 49.6, 47.8, 44.0, 36.4. ESI-MS m/z: 378.4 $[M+MeOH+Na]^+$ HPLC $t_{ret}$=3.57 min.

Example 53

(RS)-1-(2-Methoxyethyl)-3-methyl-8-(4-(7-methyl-3-oxohexahydroimidazo[1,5-a]pyrazin-2(3H)-yl)phenyl)-1,3-dihydro-2H-imidazo[4,5-c]quinolin-2-one

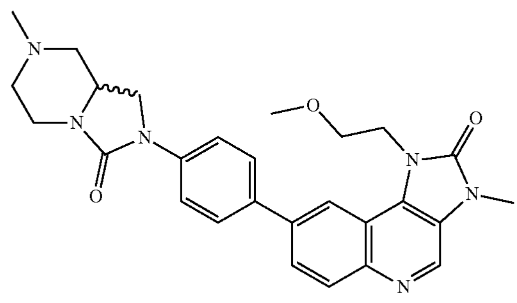 [SMILES: COCCn1c(=O)n(C)c2cnc3ccc(-c4ccc(N5CC6CN(C)CCN6C5=O)cc4)cc3c21]

The same protocol was applied as described above for the preparation of Example 46 using 38 mg (32) (0.1 mmol) and 31 mg (87) (0.1 mmol) as starting materials. Flash chromatography with gradient elution (DCM/MeOH+2N $NH_3$ 1-7%). Yield: 33 mg (68%) as white solid. $^1H$ NMR (400 MHz, $CDCl_3$) δ 8.66 (s, 1H), 8.46 (d, J=1.8 Hz, 1H), 8.15 (d, J=8.9 Hz, 1H), 7.85 (dd, J=8.9, 1.8 Hz, 1H), 7.69 (s, 4H), 4.58 (t, J=5.6 Hz, 2H), 4.01-3.88 (m, 3H), 3.86 (t, J=5.6 Hz, 2H), 3.59 (s, 3H), 3.47 (dd, J=8.6, 4.1 Hz, 1H), 3.35 (s, 3H), 3.11 (td, J=12.9, 3.5 Hz, 1H), 2.92 (dd, J=10.8, 2.8 Hz, 1H), 2.83-2.75 (m, 1H), 2.35 (s, 3H), 2.08 (td, J=11.7, 3.6 Hz, 1H), 1.98 (t, J=10.8 Hz, 1H). $^{13}C$ NMR (101 MHz, $CDCl_3$) δ 156.2, 154.3, 144.5, 140.4, 138.5, 134.3, 132.0, 131.1, 129.7, 127.8, 126.4, 123.1, 118.1, 117.8, 116.1, 70.9, 59.5, 59.3, 54.1, 50.2, 46.6, 46.4, 43.6, 40.5, 27.8. ESI-MS m/z: 487.7 $[M+H]^+$ HPLC $t_{ret}$=1.45 min.

Example 54

8-(4-((6S,7aS)-6-(Dimethylamino)-3-oxotetrahydro-1H-pyrrolo[1,2-c]imidazol-2(3H)-yl)phenyl)-1-(2-methoxyethyl)-3-methyl-1,3-dihydro-2H-imidazo[4,5-c]quinolin-2-one

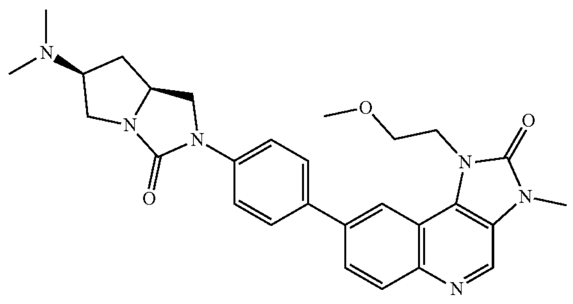

The same protocol was applied as described above for the preparation of Example 46 using 38 mg (32) (0.1 mmol) and 32 mg (95) (0.1 mmol) as starting materials. Flash chromatography with gradient elution (DCM/MeOH+2N $NH_3$ 1-7%). Yield: 40 mg (80%) as white solid. $^1H$ NMR (400 MHz, $CDCl_3$) δ 8.67 (s, 1H), 8.46 (d, J=1.6 Hz, 1H), 8.15 (d, J=8.9 Hz, 1H), 7.85 (dd, J=8.9, 1.6 Hz, 1H), 7.75-7.65 (m, 4H), 4.58 (t, J=5.6 Hz, 2H), 4.04 (t, J=8.8 Hz, 1H), 3.97-3.90 (m, 1H), 3.87 (t, J=5.6 Hz, 2H), 3.82 (dd, J=9.1, 2.4 Hz, 1H), 3.67 (dd, J=11.5, 6.9 Hz, 1H), 3.60 (s, 3H), 3.38-3.29 (m, 4H), 3.15-3.03 (m, 1H), 2.28 (s, 6H), 2.27-2.18 (m, 1H), 1.61-1.50 (m, 1H). $^{13}C$ NMR (101 MHz, $CDCl_3$) δ 160.2, 154.3, 144.6, 140.1, 138.5, 134.8, 132.1, 131.1, 129.7, 127.8, 126.5, 123.1, 118.2, 116.1, 70.9, 67.7, 59.3, 54.8, 49.5, 47.9, 43.9, 43.6, 36.3, 27.8. ESI-MS m/z: 501.7 $[M+H]^+$ HPLC $t_{ret}$=1.54 min.

Example 55

8-(4-((6R,7aS)-6-(Dimethylamino)-3-oxotetrahydro-1H-pyrrolo[1,2-c]imidazol-2(3H)-yl)phenyl)-1-(2-methoxyethyl)-3-methyl-1,3-dihydro-2H-imidazo[4,5-c]quinolin-2-one

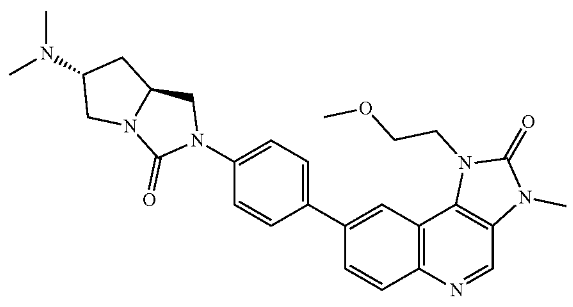

The same protocol was applied as described above for the preparation of Example 46 using 38 mg (32) (0.1 mmol) and 32 mg (98) (0.1 mmol) as starting materials. Flash chromatography with gradient elution (DCM/MeOH+2N $NH_3$ 1-7%). Yield: 41 mg (82%) as white solid. $^1H$ NMR (400 MHz, $CDCl_3$) δ 8.66 (s, 1H), 8.46 (d, J=1.4 Hz, 1H), 8.15 (d, J=8.9 Hz, 1H), 7.85 (dd, J=8.9, 1.4 Hz, 1H), 7.70 (s, 4H), 4.58 (t, J=5.6 Hz, 2H), 4.14-4.02 (m, 3H), 3.86 (t, J=5.6 Hz, 2H), 3.76-3.68 (m, 1H), 3.60 (s, 3H), 3.35 (s, 3H), 3.04-2.96 (m, 1H), 2.96-2.86 (m, 1H), 2.30 (s, 6H), 2.28-2.15 (m, 1H), 1.84-1.71 (m, 1H). $^{13}C$ NMR (101 MHz, $CDCl_3$) δ 160.3, 154.3, 144.6, 140.0, 138.5, 134.9, 132.2, 131.2, 129.8, 127.8, 126.4, 123.2, 118.3, 118.2, 116.1, 70.9, 65.7, 59.3, 53.9, 50.5, 49.6, 43.9, 43.6, 36.5, 27.8. ESI-MS m/z: 501.7 $[M+H]^+$ HPLC $t_{ret}$=1.53 min.

Example 56

8-(4-((6S,7aR)-6-(Dimethylamino)-3-oxotetrahydro-1H-pyrrolo[1,2-c]imidazol-2(3H)-yl)phenyl)-1-(2-methoxyethyl)-3-methyl-1,3-dihydro-2H-imidazo[4,5-c]quinolin-2-one

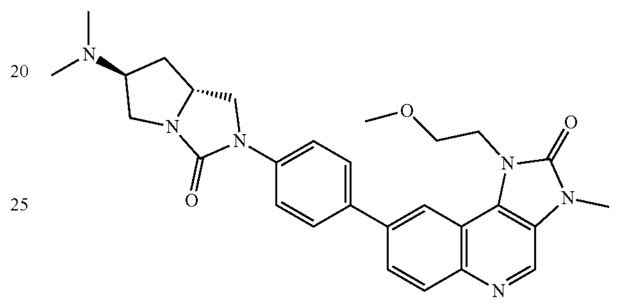

The same protocol was applied as described above for the preparation of Example 46 using 38 mg (32) (0.1 mmol) and 32 mg (105) (0.1 mmol) as starting materials. Flash chromatography with gradient elution (DCM/MeOH+2N $NH_3$ 1-7%). Yield: 40 mg (80%) as white solid. $^1H$ NMR (400 MHz, $CDCl_3$) δ 8.67 (s, 1H), 8.46 (d, J=1.5 Hz, 1H), 8.15 (d, J=8.9 Hz, 1H), 7.85 (dd, J=8.9, 1.5 Hz, 1H), 7.70 (s, 4H), 4.58 (t, J=5.6 Hz, 2H), 4.14-4.04 (m, 3H), 3.86 (t, J=5.6 Hz, 2H), 3.76-3.67 (m, 1H), 3.60 (s, 3H), 3.35 (s, 3H), 3.00 (dd, J=11.9, 7.3 Hz, 1H), 2.95-2.85 (m, 1H), 2.30 (s, 6H), 2.28-2.17 (m, 1H), 1.83-1.72 (m, 1H). $^{13}C$ NMR (101 MHz, $CDCl_3$) δ 160.3, 154.3, 144.6, 140.0, 138.5, 134.9, 132.2, 131.2, 129.8, 127.8, 126.4, 123.2, 118.3, 118.2, 116.1, 70.9, 65.6, 59.3, 53.9, 50.5, 49.6, 43.9, 43.6, 36.5, 27.8. ESI-MS m/z: 501.7 $[M+H]^+$ HPLC $t_{ret}$=1.53 min.

Example 57

8-(4-((6R,7aR)-6-(Dimethylamino)-3-oxotetrahydro-1H-pyrrolo[1,2-c]imidazol-2(3H)-yl)phenyl)-1-(2-methoxyethyl)-3-methyl-1,3-dihydro-2H-imidazo[4,5-c]quinolin-2-one

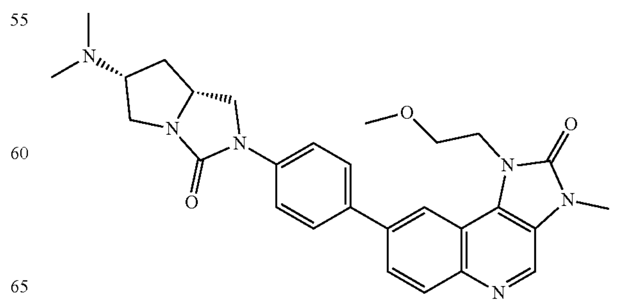

The same protocol was applied as described above for the preparation of Example 46 using 38 mg (32) (0.1 mmol) and 32 mg (108) (0.1 mmol) as starting materials. Flash chromatography with gradient elution (DCM/MeOH+2N $NH_3$ 1-7%). Yield: 39 mg (78%) as white solid. $^1H$ NMR (400 MHz, $CDCl_3$) δ 8.67 (s, 1H), 8.46 (d, J=1.6 Hz, 1H), 8.15 (d, J=8.9 Hz, 1H), 7.85 (dd, J=8.9, 1.6 Hz, 1H), 7.77-7.65 (m, 4H), 4.58 (t, J=5.6 Hz, 2H), 4.04 (t, J=8.8 Hz, 1H), 3.97-3.90 (m, 1H), 3.87 (t, J=5.6 Hz, 2H), 3.82 (dd, J=9.1, 2.3 Hz, 1H), 3.67 (dd, J=11.5, 6.9 Hz, 1H), 3.60 (s, 3H), 3.39-3.30 (m, 4H), 3.15-3.04 (m, 1H), 2.28 (s, 6H), 2.26-2.18 (m, 1H), 1.61-1.50 (m, 1H). $^{13}C$ NMR (101 MHz, $CDCl_3$) δ 160.2, 154.3, 144.6, 140.1, 138.5, 134.7, 132.1, 131.1, 129.7, 127.8, 126.4, 123.1, 118.2, 116.1, 70.9, 67.7, 59.3, 54.8, 49.5, 47.9, 43.9, 43.6, 36.3, 27.8. ESI-MS m/z: 501.7 $[M+H]^+$ HPLC $t_{ret}$=1.51 min.

Example 58

Biological evaluation of the compounds of the invention

Enzymatic ATM Assay:

The inhibitory activity on the isolated ATM kinase was determined by a commercial supplier (Reaction Biology Corp., PA, US) using an activity based FRET assay. Compounds were therefore first pre-incubated with human ATM before substrate (p53) and ATP were added to initiate the phosphorylation reaction. After a given time, the kinase reaction was stopped and the amount of phosphorylated substrate was quantified using standard FRET detection methods. Based on a 5-point dilution row starting at 10 μM with a 10-fold dilution factor, the half-maximal inhibitory concentration ($IC_{50}$ value) was calculated for each final compound. Detailed assay conditions and parameters can be requested from the commercial supplier.

Cellular Assay:

A selection of compounds was screened in a cellular assay system in two different cancer cell lines. Therefore, the cells were challenged with a generally non-cytotoxic concentration of Etoposid to induce DNA double strand breaks and the activation of the ATM pathway. The cells were further treated with different concentrations of the final compounds and viability of the cells was quantified using a standard XTT cell viability protocol. The principle of this assay lies in the fact that only alive and thus metabolically active cells are able to catalyze the reduction of XTT ((2,3-bis-(2-methoxy-4-nitro-5-sulfophenyl)-2H-tetrazolium-5-carboxanilide) by NADH from mitochondria, into formazan. The formazan product can be then detected using an absorbance-based microplate reader. The absorbance intensity measured in each well correlates to cell viability.

In brief, $kras^{G12D}$; $myc_{OE}$; $p53^{-/-}$ murine pancreatic cancer cells (KMP53) and Panc-1 human pancreatic ductal carcinoma cells were seeded in 96-well plates and left to attach overnight. The following day, cells were treated with serial dilutions of compound or DMSO in triplicates. The cells were first pre-treated for 4 hours with inhibitor and then 300 nM of Etoposide was added to each well. Cells were then grown under normal conditions (37° C., 95% air, 5% $CO_2$) for 46 h. Following the incubation period, XTT solution was added to the cells containing 1 mg/ml XTT and 25 μM phenazine methosulfate (PMS) diluted in full culture medium. Cells were incubated in normal conditions for two more hours. For the determination of cell viability, absorbance at 450 nm was measured for each well. Absorbance values were then normalized to DMSO control and expressed as percentages of viability. Using software GraphPad Prism, the values were fitted in a nonlinear response curve and the $IC_{50}$ values were calculated.

In the enzymatic ATM assay the compounds of the invention in general show an $IC_{50}$ of ≤0.1 μM, preferably ≤0.01 μM and in particular ≤0.001 μM. In the KMP53 cell assay the compounds of the invention in general show an $IC_{50}$ of ≤100 μM, preferably ≤10 μM and in particular ≤2 μM. The results for preferred compounds of the invention are given in tables 1 to 3 below.

TABLE 1

Results of the RBC FRET enzyme assay

| Compound | RBC FRET enzyme $IC_{50}$ [μM] |
|---|---|
| Ex. 8 | 0.002 |
| Ex. 1 | 0.0023 |
| Ex. 2 | 0.0029 |
| Ex. 3 | <0.001 |
| Ex. 4 | 0.0037 |
| Ex. 6 | <0.001 |
| Ex. 7 | <0.001 |
| Ex. 10 | <0.001 |
| Ex. 5 | 0.0033 |
| Ex. 9 | <0.001 |
| Ex. 13 | 0.0023 |
| Ex. 15 | <0.001 |
| Ex. 16 | <0.001 |
| Ex. 11 | <0.001 |
| Ex. 19 | <0.001 |
| Ex. 17 | <0.001 |
| Ex. 18 | 0.004 |
| Ex. 21 | <0.001 |
| Ex. 25 | 0.007 |
| Ex. 26 | 0.004 |
| Ex. 27 | <0.001 |
| Ex. 28 | <0.001 |
| Ex. 46 | 0.003 |
| Ex. 49 | <0.001 |
| Ex. 50 | <0.001 |
| Ex. 51 | <0.001 |
| Ex. 52 | <0.001 |

TABLE 2

Results of the KMP 53 cell assay

| Compound | KMP53 cell $IC_{50}$ [μM] |
|---|---|
| Ex. 1 | 6.90 |
| Ex. 2 | 8.10 |
| Ex. 3 | 7.50 |
| Ex. 4 | 2.10 |
| Ex. 5 | 3.40 |
| Ex. 6 | 3.42 |
| Ex. 7 | 2.50 |
| Ex. 8 | 0.41 |
| Ex. 9 | 1.58 |
| Ex. 10 | 1.45 |
| Ex. 11 | 4.00 |
| Ex. 19 | 9.93 |
| Ex. 20 | 3.80 |
| Ex. 27 | 4.79 |
| Ex. 28 | 2.00 |
| Ex. 46 | 8.94 |
| Ex. 48 | 7.95 |
| Ex. 50 | 8.04 |
| Ex. 52 | 5.47 |

TABLE 3

| Results of the Panc1 cell assay | |
|---|---|
| Compound | Panc1 cell $IC_{50}$ [μM] |
| AZD0156 | 0.305 |
| Ex. 19 | 0.009 |
| Ex. 17 | 0.004 |
| Ex. 27 | 0.001 |
| Ex. 28 | 0.001 |

AZD0156:

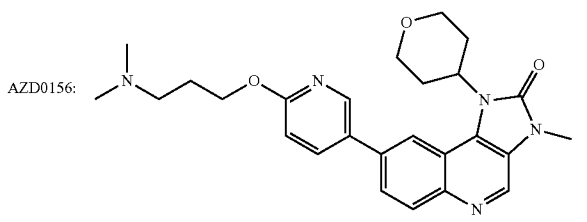

Therefore, what is claimed, is:

1. A compound selected from

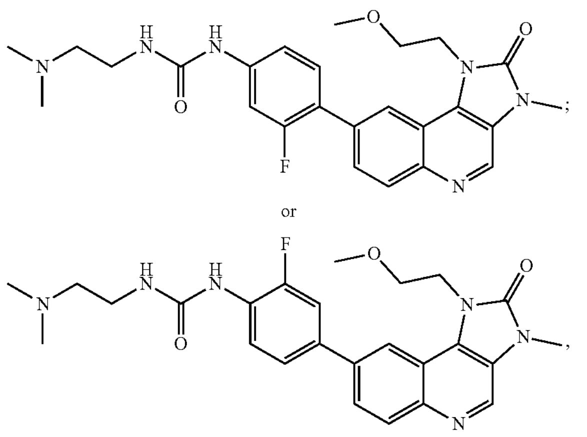

or or a pharmaceutically acceptable salt, prodrug, solvate or stereoisomer thereof.

2. A pharmaceutical composition comprising the compound of claim 1 or a pharmaceutically acceptable salt, prodrug, solvate or stereoisomer thereof, together with an inert carrier or one or more other therapeutic agents.

3. A method for treating a disease in which mediation of ATM kinase is beneficial in a human or a warm-blooded animal in need of such treatment, which comprises administering to said human or warm-blooded animal a therapeutically effective amount of the compound of claim 1 or the pharmaceutically acceptable salt, prodrug, solvate or stereoisomer thereof, or the composition of claim 2.

4. A method for treating cancer in a human or a warm-blooded animal in need of such treatment, which comprises administering to said human or warm-blooded animal a therapeutically effective amount of the compound of claim 1 or a pharmaceutically acceptable salt, prodrug, solvate or stereoisomer thereof, or the composition of claim 2.

5. The method of claim 4, wherein said cancer is selected from the group consisting of: colorectal cancer, glioblastoma, gastric cancer, ovarian cancer, diffuse large B-cell lymphoma, chronic lymphotic leukemia, acute myeloid leukemia, head and neck squamous cell carcinoma, breast cancer, hepatocellular carcinoma, small cell lung cancer, or non-small cell lung cancer.

6. The method of claim 4 in combination with radiotherapy.

7. The method of claim 6, wherein the radiotherapy is selected from external radiation therapy, intraoperative radiation therapy, internal radiation therapy, brachytherapy, or systemic therapy.

* * * * *